(12) United States Patent
Parish et al.

(10) Patent No.: US 12,295,966 B2
(45) Date of Patent: *May 13, 2025

(54) COMPOUNDS FOR TREATING AND PREVENTING EXTRACELLULAR HISTONE MEDIATED PATHOLOGIES

(71) Applicants: The Australian National University, Acton (AU); Griffith University, Nathan (AU)

(72) Inventors: Christopher Parish, Kingston (AU); Connor O'Meara, Newcastle (AU); Lucy Coupland, Chifley (AU); Benjamin Ju Chye Quah, Jeffabomberra (AU); Farzaneh Kordbacheh, Belconnen (AU); Anna Orlov, Narrabundah (AU); Anna Browne, Acton (AU); Ross Stephens, Stirling (AU); Gregory David Tredwell, Turner (AU); Lee Andrew Philip, Greenleigh (AU); Karen Knox, Ellen Grove (AU); Laurence Mark von Itzstein, Gilston (AU); Chih-Wei Chang, Upper Commera (AU); Anne Brüstle, Acton (AU); David Anak Simon Davis, Acton (AU)

(73) Assignees: The Australian National University, Acton (AU); Griffith University., Nathan (AU)

(*) Notice: Subject to any disclaimer, the term of this patent is extended or adjusted under 35 U.S.C. 154(b) by 10 days.

This patent is subject to a terminal disclaimer.

(21) Appl. No.: 18/106,138

(22) Filed: Feb. 6, 2023

(65) Prior Publication Data
US 2023/0255992 A1    Aug. 17, 2023

Related U.S. Application Data

(63) Continuation of application No. 16/770,987, filed as application No. PCT/AU2018/051337 on Dec. 14, 2018, now Pat. No. 11,628,179.

(30) Foreign Application Priority Data

Dec. 15, 2017   (AU) ................................ 2017905024

(51) Int. Cl.
    A61K 31/7028    (2006.01)
    A61K 31/7016    (2006.01)
    A61P 7/02       (2006.01)
    A61P 37/06      (2006.01)

(52) U.S. Cl.
    CPC ...... *A61K 31/7028* (2013.01); *A61K 31/7016* (2013.01); *A61P 7/02* (2018.01); *A61P 37/06* (2018.01)

(58) Field of Classification Search
    CPC .................................................. C07H 11/00
    See application file for complete search history.

(56) References Cited

FOREIGN PATENT DOCUMENTS

| EP | 0771815 A1 | 5/1997 |
| WO | 1994/022885 A1 | 10/1994 |
| WO | 2005/061523 A1 | 7/2005 |
| WO | 2005/085264 A1 | 9/2005 |
| WO | 2012/071611 A1 | 6/2012 |

OTHER PUBLICATIONS

Probst, K.C., et al., "Synthesis and Conformational Investigations of Sulfated Carbohydrates", Journal of Carbohydrate Chemistry, 2001, vol. 20, pp. 549-560.
Mackay, I. et al., The New England Journal of Medicine, "Autoimmune Diseases", vol. 345, No. 5, pp. 340-350 (Year: 2001).
"Prevent", WordNet Search 3.1, available at http://wordnetweb.princeton.edu/perl/webwn, last accessed Jan. 2021 (Year: 2021).
Allam, et al., "Histones from Dying Renal Cells Aggravate Kidney Injury via TLR2 and TLR4", Journal of the American Society of Nephrology, vol. 23, No. 8., pp. 1375-1388, (2012).
Allam, et al., "Histones trigger sterile inflammation by activating the NLRP3 inflammasome", European Journal of Immunology, vol. 43, pp. 3336-3342, (2013).
Bjelobaba, et al., "Animal models of multiple sclerosis: Focus on experimental autoimmune encephalomyelitis", Journal of Neuroscience Research, pp. 1-22, (2018).
Brill, et al., "Neutrophil extracellular traps promote deep vein thrombosis in mice", Journal of Thrombosis and Haemostasis, vol. 10, No. 1, pp. 136-144, Jan. 2012.
Fuchs, et al., "Extracellular DNA traps promote thrombosis", PNAS, vol. 107, No. 36, pp. 15880-15885, Sep. 7, 2010.

(Continued)

*Primary Examiner* — Bahar Craigo
(74) *Attorney, Agent, or Firm* — Greenberg Traurig, LLP; David J. Dykeman; Natalie Salem

(57) ABSTRACT

The present invention relates to compounds with high chemical stability and methods for inhibiting the pathological activity of extracellular histones in a subject. In particular, the invention relates to compounds with high chemical stability, uses thereof and methods for inhibiting or ameliorating extracellular histone mediated ailments (such as, for example, sepsis, systemic immune response syndrome (SIRS) and ischemia reperfusion injury (IRI)). More particularly, the invention relates to methods and uses of a polyanionic sulfated cellobioside modified with a small uncharged glycosidically linked substituent at its reducing terminus, wherein the presence of the substituent results in a molecule with high chemical stability without affecting the ability of the molecule to be effective in the therapy of extracellular histone mediated ailments. For example, the present invention relates to methods and uses of β-O-methyl cellobioside sulfate (mCBS) or a pharmaceutically acceptable salt thereof (e.g., mCBS.Na), in the therapy of a range of extracellular histone mediated ailments in subjects.

12 Claims, 31 Drawing Sheets

(56) References Cited

OTHER PUBLICATIONS

Ge, et al., "Neutrophil extracellular traps in ischemia-reperfusion injury-induced myocardial no-reflow: therapeutic potential of DNase-based reperfusion strategy", American Journal of Physiology—Heart Circulatory Physiology, vol. 2, No. 4, pp. H500-H509, Mar. 1, 2015.
Hakkim, et al., "Impairment of neutrophil extracellular trap degradation is associated with lupus nephritis", PNAS, vol. 107, No. 21, pp. 9813-9818, May 25, 2010.
Huang, et al., "Endogenous Histones Function as Alarmins in Sterile Inflammatory Liver Injury Through Toll-like Receptor 9 in Mice", Hepatology, pp. 999-1008, Sep. 2011.
Itagaki, et al., "Mitochondrial DNA Released by Trauma Induces Neutrophil Extracellular Traps", PLOS One, vol. 10, No. 3, pp. 1-10, Mar. 16, 2015.
Kessenbrock, et al., "Netting neutrophils in autoimmune small-vessel vasculitis", Nature Medicine, vol. 15, No. 6, pp. 623-625, Jun. 2009.
Knight, et al., "Peptidylarginine Deiminase Inhibition Reduces Vascular Damage and Modulates Innate Immune Responses in Murine Models of Atherosclerosis", Circulation Research, vol. 114, No. 6, pp. 947-956, Mar. 14, 2014.
Kordbacheh, et al., "Extracellular histones induce erythrocyte fragility and anemia", Blood, vol. 130, No. 26, pp. 2884-2888, Dec. 28, 2017.
Kutcher, et al., "Extracellular histone release in response to traumatic injury: implications for a compensatory role of activated Protein C", The Journal of Trauma and Acute Care Surgery, vol. 73, No. 6, pp. 1-14, Dec. 2012.
Laridan, et al., "Neutrophil extracellular traps in ischemic stroke thrombi: NETs in Stroke", Annals of Neurology, vol. 82, No. 2, pp. 223-231, Jul. 11, 2017.
Lin, et al., "Mast cells and neutrophils release IL-17 through extracellular trap formation in psoriasis", The Journal of Immunology, vol. 187, No. 1, pp. 490-500, Jul. 1, 2011.
Liu, et al., "Accuracy of circulating histones in predicting persistent organ failure and mortality in patients with acute pancreatitis", British Journal of Surgery, vol. 104, Issue 9, pp. 1215-1225, Aug. 2017.
Mangold, et al., Coronary Neutrophil Extracellular Trap Burden and Deoxyribonuclease Activity in ST-Elevation Acute Coronary Syndrome Are Predictors of ST-Segment Resolution and Infarct Size, Circulation Research, vol. 116, No. 7, pp. 1182-1192, (2015).
O'Meara, et al., "Neutralizing the pathological effects of extracellular histones with small polyanions", Nature Communications, vol. 11, No. 6405, pp. 1-17, Dec. 16, 2020.
Pisetsky, David S.., "Immune activation by histones: Plusses and minuses in inflammation", European Journal of Immunology, vol. 43, Issue 12, pp. 3163-3166, Dec. 2013.
Saffarzadeh, et al., "Neutrophil Extracellular Traps Directly Induce Epithelial and Endothelial Cell Death: A Predominant Role of Histones", PLOS One, vol. 7, Issue 2, e32366, Feb. 2012.
Savchenko, et al., "VWF-mediated leukocyte recruitment with chromatin decondensation by PAD4 increases myocardial ischemia/reperfusion injury in mice" Blood, vol. 123, No. 1, pp. 141-148, Jan. 2, 2014.
Savchenko, et al., "Neutrophil extracellular traps form predominantly during the organizing stage of human venous thromboembolism development", Journal of Thrombosis and Haemostasis, vol. 12, No. 6, pp. 860-870, Jun. 2014.
Schmiedeke, et al., "Histones Have High Affinity for the Glomerular Basement Membrane, Relevance for Immune Complex Formation in Lupus Nephritis", Journal of Experimental Medicine, vol. 169, No. 6, pp. 1879-1894, Jun. 1, 1989.
Semararo, et al., "Extracellular histones promote thrombin generation through platelet-dependent mechanisms: involvement of platelet TLR2 and TLR4", Blood, vol. 118, No. 7, pp. 1952-1961, Aug. 18, 2011.
Semararo, et al., "Histones induce phosphatidylserine exposure and a procoagulant phenotype in human red blood cells", Journal of Thrombosis and Haemostasis, vol. 12, No. 10, pp. 1697-1702, Oct. 2014.
Urban, et al., "Neutrophil Extracellular Traps Contain Calprotectin, a Cytosolic Protein Complex Involved in Host Defense against Candida albicans", PLoS Pathogens, vol. 5, Issue 10, e1000639, Oct. 2009.
Warnatsch, et al., "Neutrophil extracellular traps license macrophages and Th17 cells for cytokine production in atherosclerosis", Science, vol. 349, Issue 6245, pp. 316-320, Jul. 17, 2015.
Xu, et al., "Extracellular histones are major mediators of death in sepsis", Nature Medicine, vol. 15, No. 11, pp. 318-1321, Nov. 2009.
Xu, et al., "Extracellular Histones Are Mediators of Death through TLR2 and TLR4 in Mouse Fatal Liver Injury", The Journal of Immunology, vol. 187, No. 5, pp. 2626-2631, Sep. 1, 2011.
Xu, et al., "Sepsis and ARDS: The Dark Side of Histones", Mediators of Inflammation, vol. 2015, Article ID 205054, 9 pages, (2015).
Alhamdi, et al., "Circulating Histones Are Major Mediators of Cardiac Injury in Patients With Sepsis", Crit Care Med., vol. 43, No. 10, pp. 2094-2103, Oct. 2015.
Haroun-Bouhedja et al., Thrombosis Research, "Relationship between Sulfate Groups and Biological Activities of Fucans", 2000, vol. 100, pp. 453-459 (Year: 2000).
U.S. Appl. No. 16/770,987 US20210205343A1, filed Jun. 9, 2020 Jul. 8, 2021, Compounds for Treating and Preventing Extracellular Histone Mediated Pathologies.

months

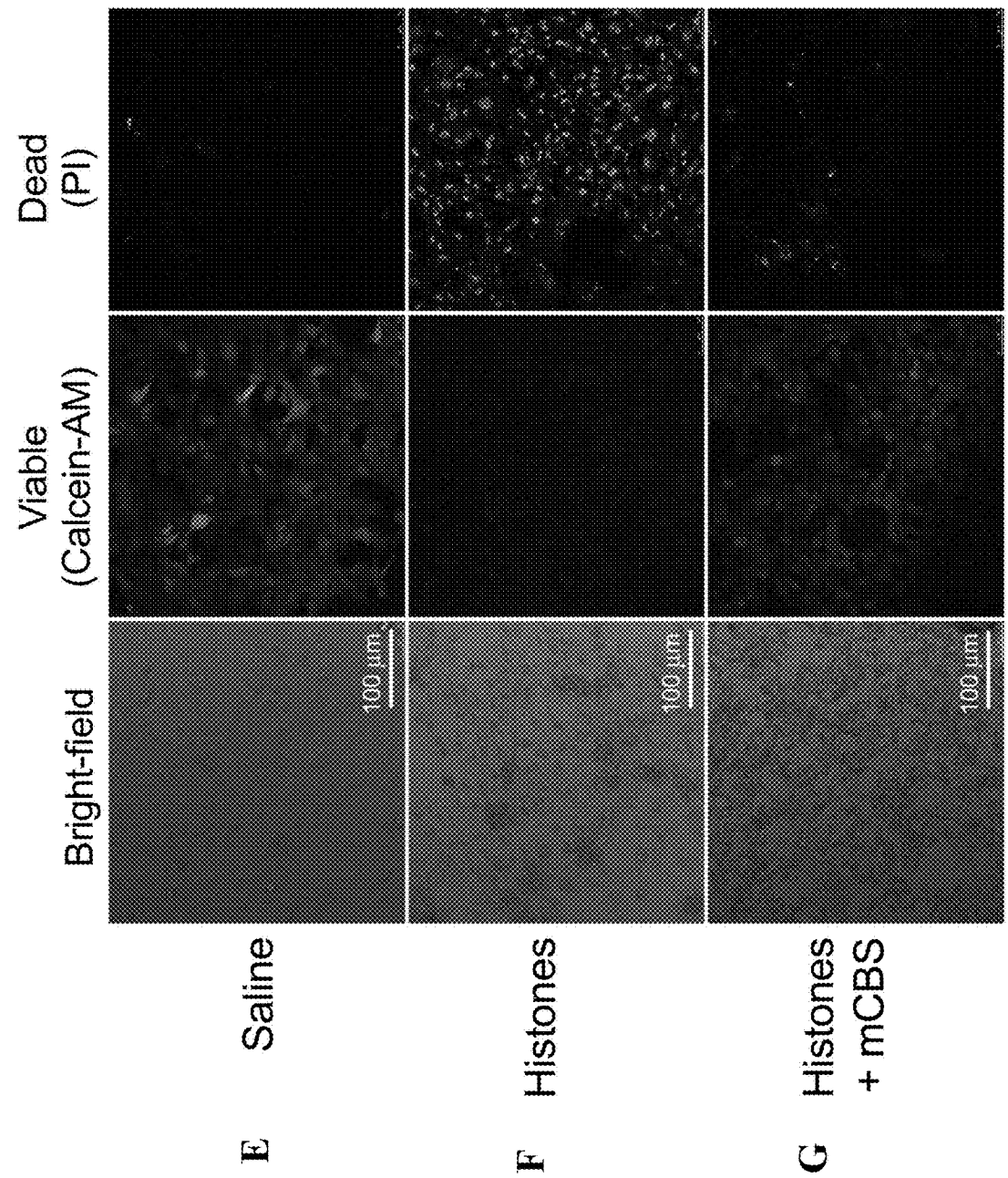
FIG. 5 (con't)

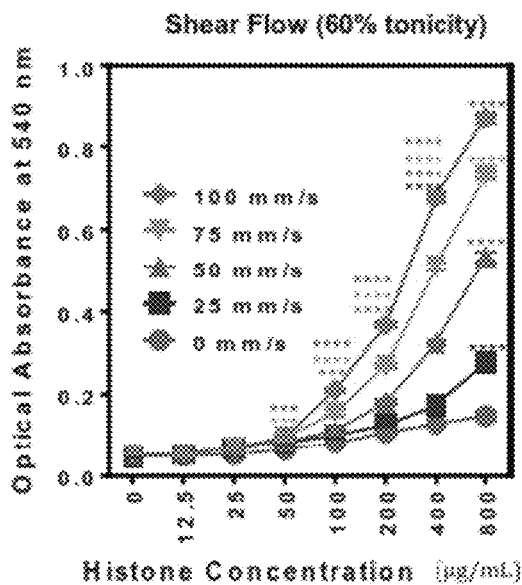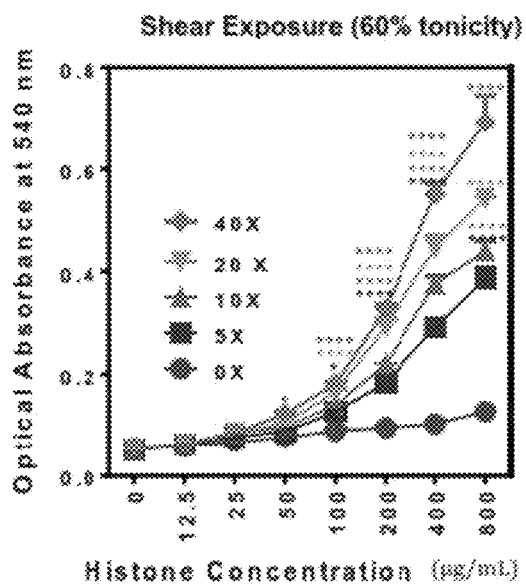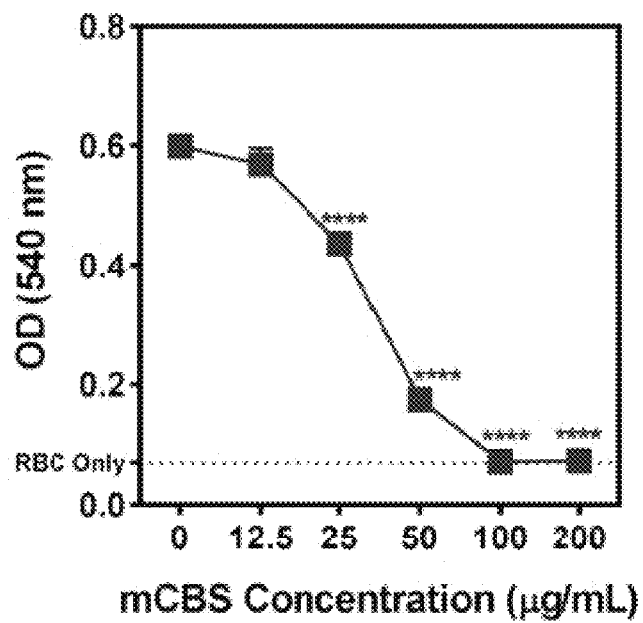

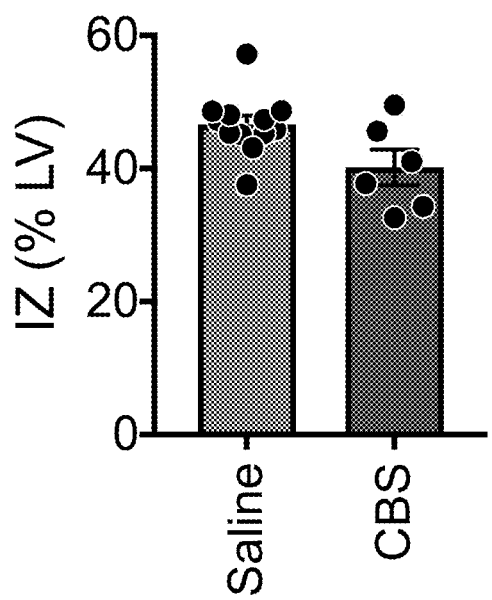
FIG. 24A Ischemic Zone
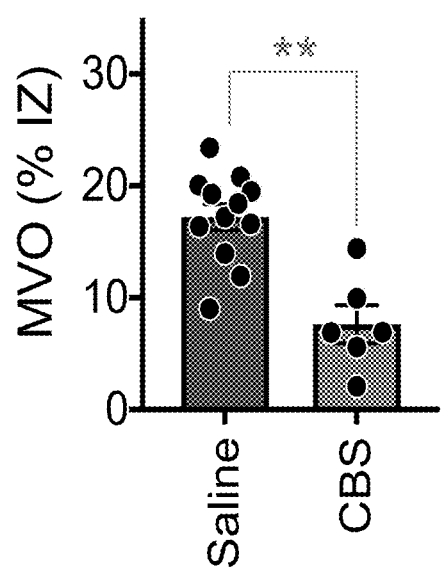
FIG. 24B Microvascular Obstruction
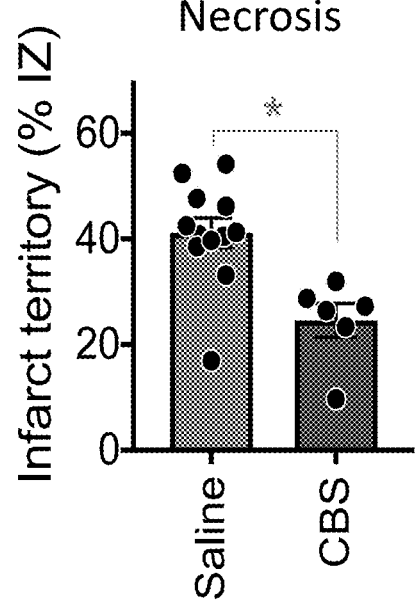
FIG. 24C Myocardial Necrosis

COMPOUNDS FOR TREATING AND PREVENTING EXTRACELLULAR HISTONE MEDIATED PATHOLOGIES

RELATED APPLICATIONS

This application is a continuation application of U.S. patent application Ser. No. 16/770,987, filed Jun. 9, 2020, now U.S. Pat. No. 11,628,179, which is a U.S. national phase application of PCT International Patent Application No. PCT/AU2018/051337, filed on Dec. 14, 2018, which claims the benefit of and priority to Australian Provisional Patent Application No. 2017905024, filed Dec. 15, 2017, the disclosure of each of which is incorporated herein by reference in its entirety.

TECHNICAL FIELD

The present invention relates to compounds and methods for inhibiting the pathological activity of extracellular histones in a subject. In particular, the invention relates to compounds, uses and methods for inhibiting or ameliorating extracellular histone mediated ailments (such as, for example, sepsis, systemic immune response syndrome (SIRS) and ischemia reperfusion injury (IRI)). More particularly, the invention relates to methods and uses of a polyanionic sulfated cellobioside modified with a small uncharged glycosidically linked substituent at its reducing terminus, wherein the presence of the substituent results in a molecule with high chemical stability without affecting the ability of the molecule to be effective in the therapy of extracellular histone mediated ailments. For example, the present invention relates to methods and uses of β-O-methyl cellobioside sulfate (mCBS) or a pharmaceutically acceptable salt thereof (e.g. mCBS.Na), in the therapy of a range of extracellular histone mediated ailments in subjects.

BACKGROUND

Histones are small basic proteins that function in the cell nucleus to regulate gene expression by complexing with DNA to form nucleosomes, which assemble into chromatin structure. Besides intranuclear functions, Xu et al, (Nat Med. 2009. 15:1318-21) reported a cytotoxic activity for histones released in to inflammatory processes with the extracellular histones acting as mediators of endothelial cell dysfunction, organ failure and death in sepsis.

Histones are now also recognised as endogenous danger signals or DAMPs when they translocate from the nucleus to the extranuclear space. They are frequently detected at the cell surface or in the cytoplasm of immune cells, cerebellar neurons, Schwann cells, and microglia in response to stress and have been shown to cause systemic inflammatory and toxic responses through activating Toll-like receptors and inflammasome pathways. Elevated levels of circulating histones as well as nucleosomes have been implicated in multiple pathophysiological processes and progression of diseases including autoimmune diseases, inflammatory diseases, and cancer, supporting a role for extracellular histones in many human diseases.

Several attempts have been made in recent times to find an effective new therapy for diseases mediated by extracellular histones. For example, considerable effort has been made to produce monoclonal antibodies against key mediators of inflammation, but these have proved clinically ineffective and have also been found to have dangerous side effects, particularly in sepsis patients.

Anti-histone treatments such as neutralizing antibodies, activated protein C, recombinant thrombomodulin, and heparin have been found to protect mice against lethal endotoxemia, sepsis, ischemia/reperfusion injury, trauma, pancreatitis, peritonitis, stroke, coagulation, and thrombosis but have limited clinical value due to lack of efficacy or unacceptable side-effects. For example, purified human coagulation factors, such as activated protein C (APC), including recombinant human APC (e.g., Xigris®), have had little clinical impact. There are several reasons for this. One reason includes the anti-coagulant activity of APC which leads to an increased risk of haemorrhage, thereby excluding the APC drug from therapy of SIRS which may develop in patients post-surgery or post-trauma. For the same reason, APC based therapeutics are excluded from use in sepsis that occurs in leukaemia patients who are at high risk of bleeding. Furthermore, as sepsis develops rapidly, the relatively slow mode of action of APC is a disadvantage. In fact, due to lack of efficacy, Xigris® was withdrawn from sale on 25 Oct. 2011.

Thus, despite these efforts, diseases mediated by extracellular histones remain largely untreated while being some of the most debilitating and deadly diseases that exist in humans. Hence, they represent a significant clinical concern.

One class of compound that has been applied to the treatment of conditions or diseases mediated by extracellular histones, such as sepsis, is disclosed in U.S. Pat. No. 9,226,939. That US patent is directed to an invention that relates to a method of inhibiting the cytotoxic activity of extracellular histones in a subject, which requires administration of an effective amount of a polyanion to the subject. A wide range of structurally very different polyanions were disclosed in that US patent publication.

It is against this background of the growing recognition of the role of extracellular histones in multiple diseases that the present invention has been developed.

SUMMARY OF INVENTION

Extracellular histones released in response to inflammatory challenge, are mediators contributing to endothelial dysfunction, organ failure and cell death (particularly during sepsis). The present invention is predicated on a finding that select highly stable polyanionic compounds may interact electrostatically with histones to neutralise the cytopathic, red cell damaging, platelet activating and pro-coagulant properties of these molecules. Complexing of such polyanionic molecules with extracellular histones in the circulation of a living animal provides a means to at least ameliorate the cytotoxic activity of extracellular histones.

In particular, the inventors have identified that certain sulfated disaccharides are effective at neutralizing these pathological effects of histones. For example, a polyanionic sulfated cellobioside modified with a small uncharged glycosidically linked substituent at its reducing terminus provides a chemically stable polyanion that is also able to provide highly effective treatment for extracellular histone mediated ailments (such as, for example, sepsis, SIRS and IRI and at least ameliorate those conditions in patients).

The inventors have also identified that compounds of the invention provide methods for the diagnosis, prognosis and management of extracellular histone mediated ailments.

The present invention is also founded on the inventors' finding that a polyanionic sulfated cellobioside modified with a small uncharged glycosidically linked substituent at its reducing terminus protects endothelial cells from extracellular histone cytotoxicity in a concentration dependant manner and reduces or even reverses histone induced damage such as red blood cell aggregation and lysis, and protects against cell injury and organ dysfunction e.g., in septic, SIRS and IRI subjects.

Use of a sulfated cellobioside modified with a small uncharged substituent at its reducing terminus, with resultant chemical stability, presents or provides a new general principal of application in the field of treating patients suffering from histone-mediated pathologies and/or preventing histone-mediated pathologies from occurring in at risk patients.

In a first aspect of the invention, there is provided a compound for use in the treatment or prevention of extracellular histone mediated ailments, wherein the compound comprises: a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside, improves the chemical stability of the polyanion, relative to the same polyanion that is sulfated at its reducing terminus.

Compounds of the invention when present in a therapeutically or pharmaceutically effective amount provide a means for ameliorating, treating or preventing extracellular histone mediated ailments.

In an embodiment of the invention, the modified polyanionic sulfated cellobioside, has the general structure:

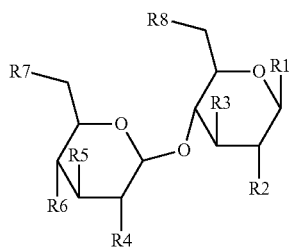

wherein: R1 is a small uncharged glycosidically linked substituent, for example, O— or S—($C_{1-6}$)alkyl; and R2 to R8 are each selected from: (i) a small uncharged O-linked substituent or (ii) a sulfate group.

Preferably, R1 is O— or S—($C_{1-6}$)alkyl. Preferably, R1 improves the chemical stability of the polyanion, compared to the same polyanion with a sulfate group at R1.

Preferably, R2 to R8 are each selected from: (a) an unmodified hydroxyl group; or (b) a sulfate group.

More preferably, R1 is a methoxy or ethoxy group and R2 to R8 are each a sulfate group selected from: O-sulfate or N-sulfate.

Desirably, the class of compound has a high net negative charge, i.e. it is a polyanion.

The anomeric configuration of the small uncharged glycoside substituent (R1) can be in either of the α or β position. Preferably, the small uncharged substituent is in the β configuration.

In a highly-preferred form of the invention, the compound is mCBS or a pharmaceutically acceptable salt thereof, which is a sulfated β-O-methyl cellobioside disaccharide. By way of illustration, the compound is the sodium salt of β-O-Methyl Cellobioside Sulfate, viz Sodium β-O-Methyl Cellobioside Sulfate (mCBS.Na).

mCBS is highly stable relative to CBS and well tolerated at high concentrations. It has minimal anticoagulant effects and is able to reduce histone-induced plasma coagulation perturbation. mCBS' anticoagulant activity is 110-fold lower than low molecular weight-heparin and 750-fold lower than unfractionated-heparin.

In a second aspect of the invention, there is provided a method for treating (either therapeutically or preventively) a medical condition, ailment or disease involving extracellular histones in a subject comprising: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

For example, in an embodiment of the second aspect of the invention, there is provided a method for treating or preventing or ameliorating sepsis, SIRS or a medical condition or disease associated with sepsis and/or SIRS in a subject, wherein the method comprises the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the modified sulfated cellobioside is mCBS or more particularly is a pharmaceutically acceptable salt thereof such as mCBS.Na.

According to this embodiment of the invention, the sepsis/SIRS treatment ameliorates the sepsis/SIRS or a septic/SIRS condition or a disease associated therewith allowing a physician to administer other drugs to treat secondary conditions.

In another embodiment of the second aspect of the invention, there is provided a method for treating or preventing or ameliorating IRI or a medical condition or disease associated with IRI in a subject, wherein the method comprises the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the modified sulfated cellobioside is mCBS or more particularly is a pharmaceutically acceptable salt thereof such as mCBS.Na.

In a third aspect of the invention, there is provided a method for ameliorating extracellular histone accumulation in a subject, said method comprising administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

For example, in an embodiment of the third aspect of the invention, the method is used to prevent a condition or ailment associated with an extracellular histone associated complication such as, for example, sepsis, SIRS or IRI.

In certain exemplary embodiments according to the second or third aspects of the invention, the identified methods can further comprise the step of: administering to the subject, together with or concomitantly with the modified sulfated cellobioside, a therapeutically or pharmaceutically effective amount of a second active agent, compound or composition selected from: one or more of anti-inflammatory agents, antibiotic agents, antiviral agents, antifungal agents and/or any other form of pharmaceutical composition that treats one or more condition that a subject is afflicted with or at risk of being afflicted with.

According to this embodiment, the second active agent, compound or composition provides an adjunct treatment to the treatment directed to the extracellular histone associated complication (such as, for example, sepsis, SIRS or IRI) and/or for medical conditions or diseases associated with such complications. Preferably, the second active agent, compound or composition comprises one or more of anti-inflammatory agents.

Preferably, the second active agent presents a means for medical intervention of a disease that a patient is afflicted with that is related to or distinct from the medical ailment treated by the compounds of this invention, said second active agent providing an adjunct treatment for the patient.

In a fourth aspect of the invention, there is provided a method for treating or preventing a medical condition or disease associated with extracellular histone cytotoxicity in a subject, wherein the method comprises the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

In one preferred example of the fourth aspect of the invention, the method is used to neutralise extracellular histones that (i) are cytotoxic towards the endothelium in a subject and/or (ii) contribute to endothelial dysfunction in a subject. In addition, or alternatively, the method is used to treat a septic or SIRS condition or an IRI or a disease associated with sepsis, SIRS or an IRI that is, caused by or mediated by a release of extracellular histones in a subject following infection, inflammation or hypoxia or any infection, inflammatory or hypoxia response in a subject.

In a fifth aspect of the invention, there is provided a therapeutic or pharmaceutical composition for use in treating an extracellular histone associated complication comprising: at least a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. Preferably, the compound is present in a therapeutically or pharmaceutically effective amount in the therapeutic or pharmaceutical composition. The composition can also include a therapeutically or pharmaceutically acceptable carrier, excipient and/or diluent. The compound in the therapeutic or pharmaceutic is either in a neutral free base form or salt form. Preferably, the polyanionic sulfated cellobioside compound is mCBS or more particularly is the sodium salt of β-O-Methyl Cellobioside Sulfate.

In certain exemplary embodiments, according to the fifth aspect of the invention, the identified composition can also comprise a second active agent, compound or composition selected from: one or more of anti-inflammatory agents, antibiotic agents, antiviral agents, antifungal agents and/or any other form of therapeutic or pharmaceutical compound that treats one or more conditions that the subject is afflicted with.

According to this embodiment, the second active agent, compound or composition desirably provides an adjunct therapy for sepsis, SIRS or an IRI or for a medical condition or disease associated with sepsis, SIRS or an IRI. Preferably, the second active agent, compound or composition comprises one or more of anti-inflammatory agents.

In a sixth aspect of the invention, there is provided a use of a therapeutically or pharmaceutically effective amount of a polyanionic sulfated cellobioside modified with a small uncharged glycosidically linked substituent at its reducing terminus or a pharmaceutically acceptable salt thereof, in the manufacture of a medicament for treating a medical condition, ailment or disease involving extracellular histones. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

For example, in an embodiment of the sixth aspect of the invention, there is provided a use of a therapeutically or pharmaceutically effective amount of a polyanionic sulfated cellobioside modified with a small uncharged glycosidically linked substituent at its reducing terminus or a pharmaceutically acceptable salt thereof, in the manufacture of a medicament for the treatment or prevention of sepsis, SIRS or an IRI or a medical condition or disease associated with sepsis, SIRS or an IRI in a subject. Preferably, the modified sulfated cellobioside is mCBS or more particularly is a pharmaceutically acceptable salt thereof such as mCBS.Na.

In one embodiment of such use, the medicament is for the treatment of sepsis, or SIRS or a medical condition or disease associated with sepsis or SIRS in a subject, wherein said treatment ameliorates or inhibits said sepsis or SIRS or said condition or disease associated with said sepsis or SIRS.

In another embodiment of such use, the medicament is for the treatment of an IRI or of a medical condition or disease associated with an IRI in a subject, wherein said treatment ameliorates or inhibits said IRI or said condition or disease associated with said injury.

In yet another embodiment of such use, the medicament is used to neutralise extracellular histones that (i) are cytotoxic towards the endothelium in a subject, or (ii) contribute to endothelial dysfunction in a subject, or (iii) initiate coagulation by activating platelets in a subject, or (iv) induce red cell fragility and resultant anaemia in a subject.

In yet another embodiment, the manufactured medicament may also include a therapeutic or pharmaceutically effective amount of a second active agent, compound or composition. According to this embodiment, the second active agent, compound or composition provides an adjunct therapy for treating a medical condition, ailment or disease involving extracellular histones. Desirably, the second active agent, compound or composition provides an adjunct therapy for the treatment of sepsis, SIRS or an IRI or for a medical condition or disease associated with sepsis, SIRS or an IRI. Preferably, the second active agent is selected from: one or more of anti-inflammatory agents, antibiotic agents, antiviral agents, antifungal agents and/or any other form of therapeutic or pharmaceutical compound that treats one or more conditions that the subject is afflicted with. More preferably, the second active agent, compound or composition comprises one or more of anti-inflammatory agents.

When the modified sulfated cellobioside compound is used in any of the methods of the invention the compound can be administered or formulated for administration to the subject in need thereof, in a single dose of formulation. In certain alternative embodiments, the modified sulfated cellobioside compound is administered, or formulated for administration to the subject in need thereof, as a multi-dose formulation.

Additional objectives, advantages and novel features will be set forth in the description which follows or will become apparent to those skilled in the art upon examination of the drawings and the ensuing detailed description of several non-limiting embodiments which follows.

BRIEF DESCRIPTION OF THE DRAWINGS

The disclosure will provide details in the following description of preferred embodiments with reference to the following figures wherein:

(FIG. 1A), 25±2° C./60% RH (FIG. 1B) and 40±2° C./75% RH (FIG. 1C) as measured by HPLC. The figures reflect the percent (%) change of mCBS and CBS relative to their starting amount (at T=0).

FIG. 10 is a graphical representation demonstrating that mCBS inhibits histone-induced RBC fragility, an effect that is exacerbated by higher shear flow rate and duration of shear exposure. Isolated human RBCs diluted in 60% saline solution (normal saline:water at a ratio of 6:4) were (panel A) incubated with increasing concentrations of histones for 60 min then exposed to increasingly rapid flow rates (mm/s) at 40× repetition and (panel B) varying repetitions of pipetting at 100 mm/s flow rate, or (panel C) treated with varying concentrations of mCBS, then exposed to 400 μg/mL histones for 60 mins and a shear flow rate of 100 mm/s and 40× pipetting repetitions, within a robotic system. The supernatant from each sample was then measured for haemoglobin content at A540 nm as an indication of the extent of RBC lysis. Error bars represent SEM. Asterisks represent significant difference from previous treatments, P values being <05 (*), <001 (*) and <0001 (**).

to stimulate faecal peritonitis and subsequent sepsis, then treated with saline (Control CLP) or 50 mg/kg of mCBS at 0, 5 and 10 hr post-op via i.p. injection and monitored for 20 hr. Once rats reached a state of severe morbidity they were humanely euthanased at which point a death was recorded. As seen in panel A mCBS treated rats showed 100% survival rate and as seen in panel B mCBS treatment significantly reduced circulating LDH levels compared to the Control CLP group of rats (Statistical analysis: two-tailed, Student's t-test, $p \leq 0.05$).

FIG. 23 CBS protects rats from severe sepsis-induced morbidity and organ damage. a, Survival of rats (n=8/group) subjected to caecal ligation and puncture (CLP) and receiving saline (Control) and CBS. P values obtained with Log rank (Mantel-Cox) test. b, Liver and kidney damage in CLP rats, as measured by ALT and creatinine blood levels, respectively.

FIG. 24 CBS reduces microvascular obstruction and myocardial necrosis in a cardiac ischemia reperfusion injury model. Effect of CBS (n=6/group) on cardiac IRI, with ischemic zone (IZ) in left ventricle (LV), microvascular obstruction (MVO) and myocardial necrosis (infarct territory) being measured.

Figure 25:
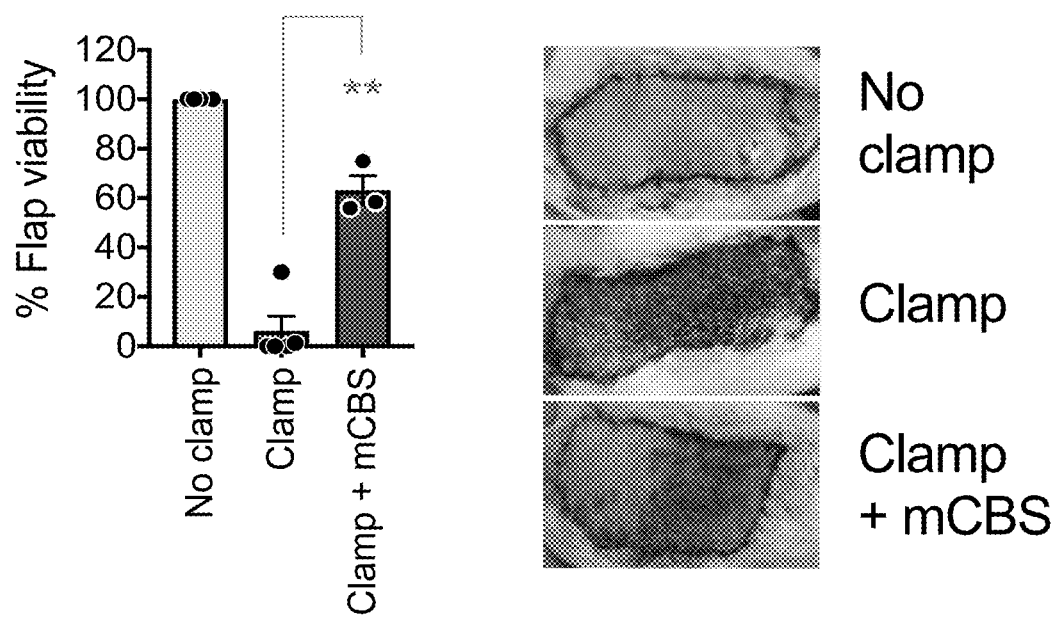

FIG. 25 demonstrates that mCBS improves tissue flap viability following ischemia reperfusion. A fasciocutaneous flap was excised from the abdomen of rats (n=3-5/group) leaving the vascular pedicle intact and the feeding vessel was clamped for 10 hr then released. mCBS (50 mg/kg) or saline was administered i.p. 5 min prior to clamp application and 5 min following its removal. The rats were monitored for a total experimental period of 72 h during which rats received additional compound or saline i.p. at 24 and 48 h post-op. Flap viability was determined at 72 hr via the extent of flap necrosis (blackened or reddened areas) with representative photos shown.

Figure 26:
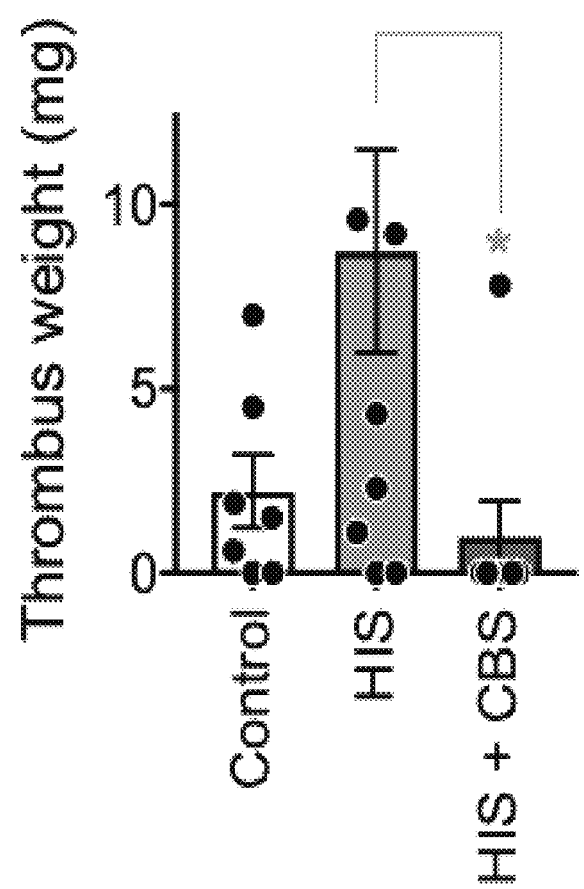

FIG. 26 shows that CBS prevents histone-induced deep vein thrombosis. The inferior vena cava (IVC) in mice (n=8/group) was ligated to ~10% patency following which all mice received an i.v. injection of histones via the tail vein (10 mg/kg) or an equivalent volume of saline followed 5 min later by an i.v. injection of CBS (50 mg/kg) or saline. Mice were monitored for 48 h after which they were re-anesthetized and any thrombi that had developed distal to the IVC stenosis were removed for analysis. Data mean±s.e.m. *$P \leq 0.05$. (ANOVA with Dunnett's multiple comparisons test).

Figure 27:
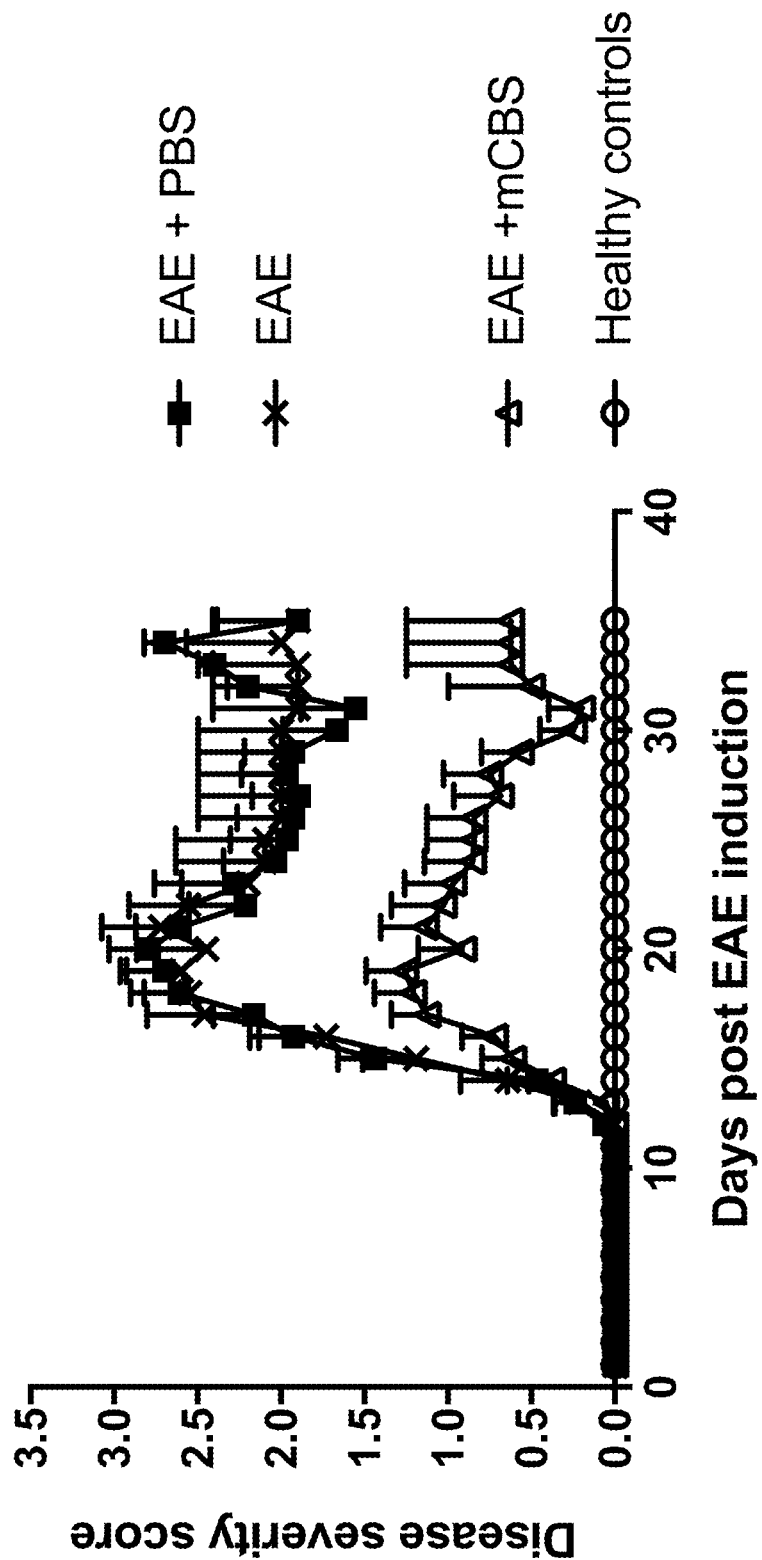

FIG. 27 shows mCBS activity in a multiple sclerosis model. C57Bl/6 mice were immunised with MOG35-55/CFA/PT to induce EAE. mCBS or PBS alone (vehicle) was given i.p. daily on day 0-9. Mice were monitored daily over a period of 17-35 days post immunisation for signs of disease. Mean clinical score of mCBS treated (n=36), and vehicle treated (n=33), EAE induced only (n=14), untreated controls (n=32). Data are from 6 independent pooled experiments. Shown are mean disease scores+/−SEM. Statistical significance was determined using the Sidak-Bonferroni method.

DETAILED DESCRIPTION OF THE PREFERRED EMBODIMENTS

The present invention is directed to the use of modified sulfated cellobioside compounds, that have high chemical stability, in the treatment or prevention of extracellular histone mediated ailments (such as, for example, sepsis, SIRS or IRI) in a subject. Such compounds can ameliorate or inhibit or prevent the cytotoxic effect of extracellular histones in a subject.

For convenience, the following sections generally outline the various meanings of terms used herein. Following this discussion, general exemplary embodiments illustrating the invention are disclosed, followed by specific examples providing more specific illustration of properties of various exemplary embodiments of the invention.

General

Those skilled in the art will appreciate that the invention described herein is susceptible to variations and modifications other than those specifically described without departing from the spirit and scope of the invention as herein described. The invention includes all such variations and modifications. The invention also includes all the steps, features, compositions and components, referred to or indicated in the specification, individually or collectively, and any and all combinations or any two or more of said steps or features. Functionally equivalent products, compositions of matter and methods are clearly within the scope of the invention as described herein.

All publications, references, documents, patents and patent applications cited in the herein, whether supra or infra, are hereby incorporated herein by reference in their entirety, which means that those publications, references, documents, patents and patent applications should be read and considered as part of this text. That any publication, reference, document, patent and patent application cited in this text is not repeated in this text is merely for reasons of conciseness. However, publications, references, documents, patents and patent applications mentioned herein are cited for describing and disclosing the protocols, reagents and products that which are reported in the publications and which might be used in connection with the invention. Nothing herein is to be construed as an admission that the invention is not entitled to antedate such disclosure by virtue of prior invention or for any other reason. All statements as to the date or representation as to the contents of these documents is based on the information available to the applicants and does not constitute any admission as to the correctness of the dates or contents of these documents.

Any manufacturer's instructions, descriptions, product specifications, and product sheets for any products mentioned herein or in any document incorporated by reference herein, are hereby incorporated herein by reference, and may be employed in the practice of the invention.

Definitions for selected terms used herein may be found within the summary of invention and the detailed description of the invention and apply throughout. Unless otherwise defined, all other scientific and technical terms used herein have the same meaning as commonly understood to one of ordinary skill in the art to which the invention belongs. If there is an apparent discrepancy between the usage of a term in the art and its definition provided herein, the definition provided within the specification shall prevail.

Definitions

Other than in the operating examples, or where otherwise indicated, all numbers expressing quantities of ingredients or reaction conditions used herein should be understood as modified in all instances by the term "about." For example, the term "about" when used in connection with percentages can mean ±10%.

Unless the context requires otherwise, or the specification specifically states to the contrary, integers, steps, or elements of the invention recited herein as singular integers, steps or elements clearly encompass both singular and plural forms of the recited integers, steps or elements. Throughout this specification, unless stated otherwise or the context requires otherwise, reference to a single step, composition or matter, group of steps or group of compositions of matter shall be taken to encompass one and a plurality (i.e., one or more) or those steps, compositions or matter, group of steps or group of compositions of matter. Accordingly, as used herein and in the appended claims, the singular forms "a, "an" and "the" include plural references unless the context clearly dictates otherwise. Thus, for example, reference to "a sulfated cellobioside modified with a small uncharged substituent at its reducing terminus or a pharmaceutically acceptable salt thereof" includes a plurality of such modified sulfated cellobioside compounds or a plurality of salts thereof, and so forth.

Throughout the specification and claims, unless the context requires otherwise, the word "comprise" or variations such as "comprises" or "comprising", will be understood to imply the inclusion of a stated step or element or integer or group of steps or elements or integers but not the exclusion of any other step or element or integer or group of steps or elements or integers.

As used herein, the term "including", as well as variations such as "includes" and "included", will also be understood to be not limiting.

In this application, the use of "or" means "and/or" unless stated otherwise.

The invention described herein may include one or more range of values (for example, size, displacement and field strength etc.). A range of values will be understood to include all values within the range, including the values defining the range, and values adjacent to the range that lead to the same or substantially the same outcome as the values immediately adjacent to that value which defines the boundary to the range. For example, a person skilled in the relevant field will understand that a 10% variation in upper or lower limits of a range can be totally appropriate and is encompassed by the invention. More particularly, the variation in upper or lower limits of a range will be 5% or as is commonly recognised in the art, whichever is greater.

As used herein, the terms "condition", "ailment" or "disease" (used interchangeably) means an extracellular histone associated complication mediated by release of extracellular histones.

As used herein, the phrase "extracellular histone associated complication" means, without particular limitation, histone mediated: (a) systemic inflammatory responses to infection such as, for example, sepsis (including bacteria, virus, fungal, parasite, prion induced sepsis), or to non-infectious inducers including surgery, trauma, haemorrhage, burns, acute pancreatitis and acute kidney injury. (b) hypoxia at the localised tissue level e.g. following blockage of an artery due to atherosclerosis, spontaneous rupture of a vessel, traumatic damage to a vessel and including cardiac and transplantation associated IRI; or at the whole body level following cessation of breathing e.g. due to drowning, gas exposure or cardiorespiratory arrest and includes ailments such as, for example, acute respiratory distress syndrome, chronic obstructive pulmonary disease and drug-mediated tissue injury; (c) haemostasis or vascular obstruction such as, for example, cardiovascular disease or chronic cardiovascular disease, such as atherosclerosis, coagulation and thrombosis (e.g., deep vein thrombosis), (d) autoimmune disease states and inflammation disease states such as, for example, multiple sclerosis, hyper-inflammatory disease states, systemic lupus erythematosus, spondyloarthropathy, ankylosing spondylitis, psoriatic arthritis, reactive arthritis, enteropathic arthritis, ulcerative colitis, Crohn's disease, irritable bowel disease, rheumatoid arthritis, juvenile rheumatoid arthritis, anti-neutrophil cytoplasmic antibody (ANCA) associated vasculitis (AAV) such as granulomatosis with polyangiitis, eosinophilic granulomatosis with polyangiitis and microscopic polyangiitis), characterized by destruction and inflammation of small vessels, familial Mediterranean fever, amyotrophic lateral sclerosis, Sjogren's syndrome, early arthritis, viral arthritis, psoriasis, age-related organ fibrosis, idiopathic pulmonary fibrosis, juvenile diabetes (Type I), diabetes mellitus (Type 2), antiphospholipid syndrome, and various central nervous system diseases such as Huntington's disease.

As used herein, the term "sepsis" includes within its meaning all stages of a sepsis disease or condition as characterised by standard medical reference texts and/or known to one of skill in the art. For example, sepsis includes severe sepsis, acute and chronic sepsis and septic shock. The term "sepsis" as used herein also includes episodes associated with infection. The term 'SIRS' (systemic immune response syndrome) used herein includes episodes not associated with infection such as, for example, trauma, burns, pancreatitis, organ transplantation, surgery, tumour lysis following therapeutic regimes for cancer, perinatal complications and immunosuppressive prophylaxis for allogeneic grafts.

As used herein, the terms "medical condition associated with sepsis or SIRS" or "disease associated with sepsis or SIRS" include within their meaning all signs and symptoms directly or indirectly associated with, derived from, caused by or accompanying any or all stages of sepsis or SIRS diseases or conditions as characterised by standard medical reference texts and/or known to one of skill in the art. For example, the medical conditions or diseases associated with sepsis or SIRS include one or more of the following signs or symptoms associated with, derived from, caused by or accompanying any or all stages of sepsis or SIRS diseases or conditions in a subject which may be manifested in the subject with or without infection: arterial hypotension, metabolic acidosis, decreased systemic vascular resistance, increased heart rate (tachycardia), increased breathing rate (tachypnoea), general or systemic inflammation, elevated or decreased white blood cell count (leucocytosis or leucopenia), increased extracellular histones in blood, organ dysfunction such as acute organ dysfunction, dysfunction of the circulatory system, multiple organ dysfunction syndrome, disseminated intravascular coagulation (DIC), deposition of fibrin in the microvasculature of one or more organs, fever, confusion, pneumonia, cough with pneumonia, kidney infection, painful urination with a kidney infection, and/or septic shock.

As used herein, the terms "decrease", "reduced", "reduction", "decrease" or "inhibit" are all used generally to mean a decrease by a statistically significant amount. However, for avoidance of doubt, "reduced", "reduction" or "decrease" or "inhibit" means a decrease by at least 10% as compared to a reference level, e.g., in the absence of an agent, for example a decrease by at least about 20%, or at least about 30%, or at least about 40%, or at least about 50%, or at least about 60%, or at least about 70%, or at least about 80%.

As used herein, the terms "improve", "increased", "increase" or "enhance" or "activate" are all used to generally mean an increase by a statically significant amount; for the avoidance of any doubt, the terms "improve", "increased", "increase" or "enhance" or "activate" means an increase of at least 10% as compared to a reference level, e.g., in in the absence of an agent, for example an increase of at least about 20%, or at least about 30%, or at least about 40%, or at least about 50%), or at least about 60%, or at least about 70%, or at least about 80%, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "administer", "administered" and "administering" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration. In certain embodiments, the compound is a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside, improves the chemical stability of the polyanion, relative to the same polyanion that is sulfated at its reducing terminus. When the above compound is present in a composition such as a therapeutic or a therapeutic composition it will be prepared for parenteral administration, or another other method allowing delivery to a target site. Some exemplary modes of administration include, but are not limited to, injection, infusion, instillation, inhalation, or ingestion.

As used herein, the term "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

As used herein, the terms "treat," "treatment," "treating" and the like, in the context of the present invention insofar as it relates to any of the conditions or diseases recited herein means to relieve, alleviate, ameliorate, inhibit, slow down, reverse, or stop the progression, aggravation, deterioration, progression, anticipated progression or severity of at least one symptom or complication associated with such condition or disease. In an embodiment, the symptoms of a condition or disease are alleviated by at least 5%, at least 10%, at least 20%, at least 30%, at least 40%, or at least 50%.

As used herein, the phrases "effective amount" "therapeutically effective amount" or "effective dose" (used interchangeably herein) include within their meaning a sufficient but non-toxic amount of a compound or composition of the invention to provide a desired effect. The exact amount of a compound or composition required will vary from subject to subject depending on factors such as the desired effect, the species being treated, the age and general condition of the subject, the severity of the condition being treated, the agent being administered, the mode of administration, and so forth. Thus, it is not possible to specify an exact "effective amount". However, for any given case, an appropriate effective amount (dose) may be determined by one of ordinary skill in the art using only routine experimentation. Generally, a therapeutically effective amount can vary with the subject's history, age, condition, sex, as well as the severity and type of the medical condition in the subject, and administration of other pharmaceutically active agents.

As used herein, reference to use of a compound or composition in therapeutic or pharmaceutical applications will be understood to be equally applicable to human and non-human, such as veterinary, applications. Hence, it will be understood that, except where otherwise indicated, reference to a "patient", "subject" or "individual" (used interchangeably herein) means a human or non-human, such as an individual of any species of social, economic or research importance including but not limited to, mammalian, avian, lagomorph, ovine, bovine, equine, porcine, feline, canine, primate and rodent species. More preferably, the patient, subject or individual is an animal belonging to a mammalian species. The mammalian species is desirably a human or non-human primate or a companion animal such as a domesticated dog, cat, horse, monkey, mouse, rat, rabbit, sheep, goat, cow or pig. In one particularly preferred example, the patient, subject or individual is a human.

Definitions for selected terms used herein may be found within the detailed description of the invention and apply throughout. Unless otherwise defined, all other scientific and technical terms used herein have the same meaning as commonly understood to one of ordinary skill in the art to which the invention belongs.

Illustrative Embodiments of the Invention

The ensuing detailed description of this invention is included solely for the purposes of illustrating the invention and should not be understood in any way as a restriction on the broad description of the invention, as set out above.

1. Compounds of the Invention

In a first aspect of the invention, there is provided a compound for use in the treatment of an extracellular histone mediated complication wherein the compound comprises: a polyanionic sulfated cellobioside modified with a small uncharged glycosidically linked substituent at its reducing terminus or a pharmaceutically acceptable salt thereof. The substituent rendering the molecule high chemical stability, relative to the same polyanion but which is sulfated at its reducing terminus. Preferably, this class of compound should have a high net negative charge.

Compounds of the invention can ameliorate extracellular histone mediated complications (such as sepsis or ischemia reperfusion injuries) both preventatively i.e. as a prophylactic pre-treatment to a medical procedure or therapeutically during treatment after the conditions or disease has occurred.

In an embodiment of the invention, the modified polyanionic sulfated cellobioside, has the general structure:

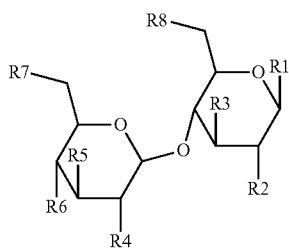

wherein: R1 is a small uncharged glycosidically linked substituent, for example, O— or S—$(C_{1-6})$alkyl; and R2 to R8 are each selected from: (i) a small uncharged O-linked substituent or (ii) a sulfate group.

Preferably, R1 is O or S—($C_{1-6}$)alkyl. Preferably, R1 improves the chemical stability of the polyanion, compared to the same polyanion with a sulfate group at R1.

Preferably, R2 to R8 are each selected from: (a) an unmodified hydroxyl group; or (b) a sulfate group.

More preferably, R1 is a methoxy or ethoxy group and R2 to R8 are each a sulfate group selected from: O-sulfate or N-sulfate.

Desirably, the class of compound has a high net negative charge, i.e. it is a polyanion.

The anomeric configuration of the small uncharged glycoside substituent (R1) can be in either of the α or β position. Preferably, the small uncharged substituent is in the β configuration.

In a highly-preferred form of the invention, the compound is β-O-Methyl Cellobioside Sulfate or a pharmaceutically acceptable salt thereof, which is a sulfated β-O-methyl cellobioside disaccharide. By way of illustration, the compound is the sodium salt of β-O-Methyl Cellobioside Sulfate.

mCBS is highly stable relative to CBS and well tolerated at high doses. It has minimal anticoagulant effects and is able to reduce histone-induced plasma coagulation perturbation. mCBS' anticoagulant activity is 110-fold lower than low molecular weight-heparin and 750-fold lower than unfractionated-heparin.

The small uncharged glycosidically linked substituent that is present at the reducing terminus of the polyanionic sulfated cellobioside, improves the chemical stability of the polyanion relative to the same polyanion that is sulfated at its reducing terminus.

Chemical stability as used herein represents the tendency of the compound of the invention to resist change (in particular decomposition in its natural environment or when exposed to air, heat, light, pressure, or other natural conditions, or due to internal reaction.

A compound of the invention is "stable" if it is does not significantly decompose, relative to the same polyanion that is sulfated at its reducing terminus, after at least one-month storage under conditions of anticipated use or normal environmental conditions.

A compound of the invention will have decomposed significantly if it has lost 3 or more sulfate groups after at least one-month storage, under conditions of anticipated use or normal environmental conditions. Preferably, a compound of the invention will have decomposed significantly if it has lost 2 sulfate groups after at least one-month storage, under conditions of anticipated use or normal environmental conditions. Most preferably, a compound of the invention will have decomposed significantly if it has lost 1 sulfate group after at least one-month storage, under conditions of anticipated use or normal environmental conditions.

Preferably, the compound of the invention is chemically stable for at least 2, 3, 4, 5, 6, 7, 8, 9, 10, 11, 12, 13, 14, 15, 16, 17, 18, 19, 20, 21, 22, 23 or 24 months when stored in a phosphate formulation buffered to pH 7.5 and stored at 2-8° C. More preferably, stability is measured over a period of 6 months to 2 years with the compound being stored in a phosphate formulation buffered to pH 7.5 and stored at about 2-8° C.

As used herein, the phrase "pharmaceutically acceptable salt(s)" includes those salts which, within the scope of sound medical judgement, are suitable for use in contact with tissues of humans and lower animals without the undue toxicity, irritation, allergic response and the like, and are commensurate with a reasonable benefit/risk ratio.

Pharmaceutically acceptable salts are well known in the art. They include, for example, acid addition salts (formed with the free amino groups of the protein) derived from inorganic acids (e.g., hydrochloric or phosphoric acids, or from organic acids (e.g., citric, acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

In a preferred form of the invention the modified sulfated cellobioside of the invention, is present as a pharmaceutically acceptable salt. By way of illustration, the compound is the sodium salt of β-O-Methyl Cellobioside Sulfate, viz Sodium β-O-Methyl Cellobioside Sulfate (mCBS.Na).

Modified sulfated cellobioside compounds or pharmaceutically acceptable salts thereof used in the methods or compositions of the present invention may be prepared by methods known to those skilled in the art. For example, methods for preparing sulfated compounds modified with an uncharged substituent at its reducing termini are generally described in Katrin C Probst and Hans Peter Wessel, 2001, *J. Carbohydrate Chemistry*, 20 (7 & 8): 549-560, which is incorporated herein by reference in its entirety.

2. Treatment Methods

As compounds of the invention and therapeutic or pharmaceutical compositions including said compounds can ameliorate or prevent the pathological activity of extracellular histone proteins, the present invention provides as a second aspect of the invention, a method of treatment or prevention for extracellular histone associated complications, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Further, in a third aspect of the invention, there is provided a method for ameliorating extracellular histone accumulation in a subject, said method comprising administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

The present invention as described by the second and third aspects of the invention contemplates treating or preventing a variety of different extracellular histone ailments that are caused by the release of histones and the resulting extracellular toxicity therefrom. According to these aspects of the invention, the respective methods can be used for the treatment or prevention of extracellular histone associated complications in a subject having: (a) systemic inflammatory responses to infection such as, for example, sepsis (including bacteria, virus, fungal, parasite, prion induced sepsis), or to non-infectious inducers including surgery, trauma, haemorrhage, burns, acute pancreatitis and acute kidney injury. (b) hypoxia at the localised tissue level e.g. following blockage of an artery due to atherosclerosis, spontaneous rupture of a vessel, traumatic damage to a vessel and including cardiac and transplantation associated IRI; or at the whole body level following cessation of breathing e.g. due to drowning, gas exposure or cardiorespiratory arrest and includes ailments such as, for example, acute respiratory distress syndrome, chronic obstructive pulmonary disease and drug-mediated tissue injury; (c) haemostasis or vascular obstruction such as, for example, cardiovascular disease or chronic cardiovascular disease, such as atherosclerosis, coagulation and thrombosis (e.g., deep vein thrombosis), (d) autoimmune disease states and inflammation disease states such as, for example, multiple sclerosis, hyper-inflammatory disease states, systemic lupus erythematosus, spondyloarthropathy, ankylosing spondylitis, psoriatic arthritis, reactive arthritis, enteropathic arthritis, ulcerative colitis, Crohn's disease, irritable bowel disease, rheumatoid arthritis, juvenile rheumatoid arthritis, anti-neutrophil cytoplasmic antibody (ANCA) associated vasculitis (AAV) such as granulomatosis with polyangiitis, eosinophilic granulomatosis with polyangiitis and microscopic polyangiitis), characterized by destruction and inflammation of small vessels, familial Mediterranean fever, amyotrophic lateral sclerosis, Sjogren's syndrome, early arthritis, viral arthritis, psoriasis, age-related organ fibrosis, idiopathic pulmonary fibrosis, juvenile diabetes (Type I), diabetes mellitus (Type 2), antiphospholipid syndrome, and various central nervous system diseases such as Huntington's disease.

In an embodiment of the second or third aspects of the invention, the respective methods may further comprise administering to the subject, at the same time or concomitantly with the compound of the invention, a second therapeutic agent (such as anti-inflammatory agents, antibiotic agents, antiviral agents, antifungal agents or other forms of medical intervention) that is distinct from the compound of the invention that provides an adjunct treatment for a medical condition that the subject is or may suffer from.

Preferably, as an example of these aspects of the invention, the respective methods provide a means for treating or preventing sepsis or SIRS or a medical condition or disease associated with sepsis or SIRS in a subject. As another example of these aspects of the invention the respective methods provide a means for treating or preventing IRI or a medical condition or disease associated with IRI in a subject.

Preferably, the method ameliorates the condition or a disease state sufficiently to allow a physician to administer other drugs to treat secondary conditions. Thus, the invention also includes administering a therapeutically effective amount of a polyanionic sulfated cellobioside modified with a small uncharged glycosidically linked substituent at its reducing terminus or a pharmaceutically acceptable salt thereof to a subject, for the purposes of ameliorating extracellular histone associated complications in the patient.

In certain exemplary embodiments according to the second or third aspects of the invention, the identified methods can further comprise the step of: administering to the subject, together with or concomitantly with the modified sulfated cellobioside, a therapeutically or pharmaceutically effective amount of a second active agent, compound or composition selected from: one or more of anti-inflammatory agents, antibiotic agents, antiviral agents, antifungal agents and/or any other form of pharmaceutical composition that treats one or more condition that a subject is afflicted with or at risk of being afflicted with.

According to this embodiment, the second active agent, compound or composition provides an adjunct treatment to the treatment directed to the extracellular histone associated complication (such as, for example, sepsis, SIRS or IRI) and/or for medical conditions or diseases associated with such complications. Preferably, the second active agent, compound or composition comprises one or more of anti-inflammatory agents.

Preferably, the second active agent presents a means for medical intervention of a disease that a patient is afflicted with that is related to or distinct from the medical ailment treated by the compounds of this invention, said second active agent providing an adjunct treatment for the patient.

Therapeutics and/or pharmaceutical compositions of the invention disclosed herein may be administered either therapeutically or preventively. In a therapeutic application, compounds and compositions are administered to a patient already suffering from extracellular histone associated complications or an ailment associated with extracellular histone associated complications, in an amount sufficient to cure or at least partially arrest its symptoms. The compound or composition should be provided in a quantity of the active compound sufficient to effectively treat the patient either in a single dose or as part of a treatment regime e.g., a multi-dose treatment regime. In a preventative application, compounds and compositions of the invention are administered to a subject at risk of developing an ailment associated with extracellular histone associated complications, in an amount sufficient to at least partially arrest the ailment's symptoms and/or complications.

In a fourth aspect of the invention, there is provided a method for treating or preventing a medical condition, ailment or disease associated with extracellular histone mediated pathology in a subject, wherein the method comprises the step of: administering to the subject a therapeutically or pharmaceutically effective amount of a polyanionic sulfated cellobioside modified with a small uncharged glycosidically linked substituent at its reducing terminus or a pharmaceutically acceptable salt thereof.

Preferably, the sulfated cellobioside is β-O-Methyl Cellobioside Sulfate (mCBS) or a pharmaceutically acceptable salt thereof.

In one preferred example, the method is used to treat extracellular histones that (i) are cytotoxic towards the endothelium in a subject, or (ii) contribute to endothelial dysfunction in a subject, or (iii) initiate coagulation by activating platelets in a subject, or (iv) induce red cell fragility and resultant anaemia in a subject.

In a highly preferred exemplary form of the invention, according to any aspect, embodiment or example describes herein, the compound of the invention is used to treat or prevent one or more of the following discussed ailments or conditions.

A. Sepsis

Sepsis (including septic shock) is a systemic reaction to infection characterized by arterial hypotension, metabolic acidosis, decreased systemic vascular resistance, tachypnoea and organ dysfunction. Sepsis (including septic shock) is also a systemic inflammatory response to infection associated with and mediated by the activation of a number of host defence mechanisms including the cytokine network, leukocytes, and the complement and coagulation fibrinolysis systems. Disseminated intravascular coagulation (DIC) with widespread deposition of fibrin in the microvasculature of various organs may be an early manifestation of sepsis. DIC is an important mediator in the development of the multiple organ failure syndrome and contributes to the poor prognosis of patients with septic shock.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Symptoms of sepsis are often related to an underlying infectious process and if left untreated can manifest as severe sepsis (sepsis with acute organ dysfunction) or septic shock (sepsis with refractory arterial hypotension). When two or more of the systemic inflammatory response syndrome criteria (e.g., general inflammation, fever, elevated white blood cell count (leukocytosis), and raised heart rate (tachycardia) and breathing rate (tachypnoea)) are met without evidence of infection, patients may be diagnosed simply with "SIRS", which is a septic inflammatory state affecting the whole body.

Many patients with sepsis exhibit a rapid decline over a 24-48 hour period. Rapid treatment is essential for effective sepsis treatment. Unfortunately, diagnosis of type of infection requires microbiological analysis to identify the pathogen which may take several days. Therefore, therapy to eliminate a pathogen (e.g. antibiotic therapy) must be initiated without knowledge of the type and species of the pathogen, and with no means of knowing the extent of the infection. The present invention provides such a method.

Patients suffering from sepsis have increased levels of extracellular histones present in their blood and these proteins have been implicated as important mediators of sepsis pathology.

In an embodiment of the second, third or fourth aspects of the invention, there is provided a method of treating (either prophylactically or therapeutically) extracellular histone associated sepsis in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

As demonstrated herein, compounds of the invention in particular mCBS block the toxic effects of extracellular histones and thereby are useful as a treatment for sepsis.

Thus, compounds of the invention and therapeutic or pharmaceutical compositions including said compounds provide a means for ameliorating the cytotoxic activity of extracellular histone proteins in sepsis, including both pre-treatment (in the case of a medical procedure) and treatment after sepsis has occurred.

B. Non-Infectious SIRS

Non-infectious Systemic inflammatory response syndrome (SIRS) is an inflammatory state affecting the whole body. It is the body's response to non-infectious insult. Although the definition of SIRS refers to it as an "inflammatory" response, it actually has pro- and anti-inflammatory components.

SIRS is a serious condition related to systemic inflammation, organ dysfunction, and organ failure. It is a subset of cytokine storm, in which there is abnormal regulation of various cytokines. SIRS is also closely related to sepsis, in which patients satisfy criteria for SIRS and have a suspected or proven infection. Causes of non-infection SIRS include, for example: trauma, from surgery, traumatic haemorrhage, burns and acute pancreatitis, by way of illustration.

In an embodiment of the second, third or fourth aspects of the invention, there is provided a method of treating (either prophylactically or therapeutically) extracellular histone associated non-infectious SIRS in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

As demonstrated herein, compounds of the invention in particular mCBS block the toxic effects of extracellular histones and thereby are useful as a treatment for non-infectious SIRS.

Thus, compounds of the invention and therapeutic or pharmaceutical compositions including said compounds provide a means for ameliorating the cytotoxic activity of extracellular histone proteins in non-infectious SIRS, including both pre-treatment (in the case of a medical procedure) and treatment after non-infectious SIRS has occurred.

B.1 Trauma

Physical trauma is a serious and body-altering physical injury, such as the crushing or amputation of a limb.

Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to SIRS, but also significantly increase the risk of subsequent infection and sepsis.

Histones are released following trauma or severe cellular stress in the absence of infection. For example, serum histone levels are significantly elevated after severe non-thoracic blunt trauma. High serum histone levels positively correlate with severe complications, incidence, and dismal prognosis. In vitro, exogenous histones lead to production and secretion of a variety of cytokines (e.g., TNF-α, IL-6, and IL-10), stimulate myeloperoxidase release, and increase calcium influx in immune and endothelial cells, which partly mediates histone-induced cytotoxicity. In vivo, histone administration also accelerates cytokine release, endothelial damage, coagulation activation, and lung injury in animal trauma models.

Patients suffering from trauma can have increased levels of extracellular histones present in their blood and these proteins have been implicated as important mediators of trauma pathology.

In an embodiment of the second, third or fourth aspects of the invention, there is provided a method of treating (either prophylactically or therapeutically) extracellular histone associated trauma in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in trauma patients.

Thus, compounds of the invention and therapeutic or pharmaceutical compositions including said compounds provide a means for ameliorating the cytotoxic activity of extracellular histone proteins in trauma, including both pre-treatment (in the case of a medical procedure) and treatment after trauma injury has occurred.

B.2. Surgery

Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

In an embodiment of the second, third or fourth aspects of the invention, there is provided a method of treating (either prophylactically or therapeutically) extracellular histone associated surgical trauma in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

As a rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anaesthesia, antiseptic conditions, typical surgical instruments, and suturing or stapling. All forms of surgery are considered invasive procedures; so-called non-invasive surgery usually refers to an excision that does not penetrate the structure being addressed (e.g., laser ablation of the cornea) or to a radio-surgical procedure (e.g., irradiation of a tumour).

As compounds of the invention and therapeutic or pharmaceutical compositions including said compounds, can ameliorate the cytotoxic activity of extracellular histone proteins, the present invention provides a treatment for use in surgical trauma, including both pre-treatment (in the case of a medical procedure) and treatment after surgical injury has occurred.

B.3. Traumatic Haemorrhage

Traumatic haemorrhage accounts for much of the wide-ranging international impact of injury, causing a large proportion of deaths and creating great morbidity in the injured. Despite differences in pre-hospital care, the acute management of traumatic haemorrhage is similar around the world and follows well accepted published guidelines. A critically injured patient's care occurs as four, often overlapping segments: the resuscitative, operative, and critical care phases. The diagnosis and control of bleeding should be a high priority during all the phases of trauma care and is especially important in the patient who is in haemorrhagic shock. Early attempts at haemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of haemorrhage, and appropriate transfusion of blood and blood products are provided. In the operative phase, surgical control of the haemorrhage and any other injury, and additional transfusion is provided. Finally, the critical care phase provides for post-operative support and tissue perfusion).

As compounds of the invention and therapeutic or pharmaceutical compositions including said compounds, can ameliorate the cytotoxic activity of extracellular histone proteins, the present invention provides to treatment for use in traumatic haemorrhage, including both pre-treatment (in the case of a medical procedure) and treatment after traumatic haemorrhage has occurred.

B.4. Burns

A burn can be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

Various burns lead to an increase in the levels of extracellular histones which in turn are associated with toxicity. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

Patients suffering from burns can have increased levels of extracellular histones present in their blood and these proteins have been implicated as important mediators of burns pathology.

In an embodiment of the second or third aspect of the invention, there is provided a method of ameliorating histone induced cytotoxicity caused by burns to a subject, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in burns patients.

Thus, compounds of the invention and therapeutic or pharmaceutical compositions including said compounds provide a means for ameliorating the cytotoxic activity of extracellular histone proteins in a burn in a subject.

B.5. Acute Pancreatitis

Acute pancreatitis is characterized as rapidly-onset inflammation of the pancreas by sterile inflammation and acinar cell death, including necrosis and apoptosis. In this respect, extracellular histone-mediated HMGB1 release in activated immune cells is responsible for 1-arginine-induced acute pancreatitis in HMGB1 pancreatic conditional knockout mice. Loss of HMGB1 in the pancreas increases histone release into the circulation after extensive nuclear injury and cell death. Circulating histones recruit macrophages, resulting in macrophage activation and further HMGB1 release.

Depending on its severity, acute pancreatitis can have severe complications and high mortality despite treatment. While mild cases are often successfully treated with conservative measures or laparoscopy, severe cases require invasive surgery (often more than one intervention) to contain the disease process.

Patients suffering from acute pancreatitis can have increased levels of extracellular histones present in their blood and these proteins have been implicated as important mediators of acute pancreatitis pathology.

In an embodiment of the second, third or fourth aspects of the invention, there is provided a method of treating (either prophylactically or therapeutically) extracellular histone associated acute pancreatitis in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in acute pancreatitis patients.

Thus, compounds of the invention and therapeutic or pharmaceutical compositions including said compounds provide a means for ameliorating the cytotoxic activity of extracellular histone proteins in acute pancreatitis, including both pre-treatment (in the case of a medical procedure) and treatment after acute pancreatitis has occurred.

C. Ischemia-Reperfusion Injury

Ischemia reperfusion injuries (including transplantation associated Ischemia reperfusion injuries) and drug-mediated tissue injury result in sterile inflammation, a process occurring in the absence of microorganisms.

Ischemia is a restriction in blood supply to tissues, causing a shortage of oxygen that is needed for cellular metabolism. In prolonged ischemia (60 min or more), hypoxanthine is formed as a breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signalling.

Reperfusion injury refers to damage due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane can in turn cause the release of more free radicals. Such reactive species act indirectly in redox signalling to turn on apoptosis. Leukocytes also build up in small capillaries, obstructing them and leading to more ischemia.

Reperfusion injury also plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

Serum histone levels are significantly elevated in animal Ischemia reperfusion models with liver, kidney, lung, and brain injury, suggesting an important role of histones in the regulation of sterile inflammation. Indeed, circulating histones are major mediators of animal death in several liver injury models including concanavalin A-triggered liver injury, acetaminophen-induced hepatotoxicity, liver I/R, and acute liver failure.

Once released, histones selectively bind to Toll-like receptors (TLRs) including TLR2, TLR4, and TLR927 to produce pro-inflammatory cytokines (e.g., TNF-α and IL-6), which in turn accelerates inflammatory responses and tissue injury.

Extracellular histones mediate not only liver, but also acute kidney injury or ischemic stroke through direct toxicity or pro-inflammatory effects. Similarly, TLR2 and TLR4-mediated signalling pathways (e.g., MyD88, NF-κB, and mitogen activated protein kinase (MAPK)) are responsible for extracellular histone-mediated acute kidney injury.

Histone infusion increases brain infarct size and exacerbates stroke outcome. Serum H3 and H4 levels are remarkably increased in bronchoalveolar lavage fluid from acute lung injury (ALI) animal models or patients.

Collectively, extracellular histones function as DAMPs and mediate sterile inflammation and organ damage. Inhibition of histone release and activity presents a therapeutic strategy for tissue injury.

Patients suffering from ischemia reperfusion injuries (including transplantation associated ischemia reperfusion injuries) and drug-mediated tissue injury have increased levels of extracellular histones present in their blood and these proteins have been implicated as important mediators of ischemia/reperfusion and drug-mediated tissue injury pathology.

In an embodiment of the second, third or fourth aspects of the invention, there is provided a method of treating (either prophylactically or therapeutically) extracellular histone associated IRI and/or drug-mediated tissue injury in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in ischemia/reperfusion and drug-mediated tissue injury patients.

Thus, compounds of the invention and therapeutic or pharmaceutical compositions including said compounds provide a means for ameliorating the cytotoxic activity of extracellular histone proteins in ischemia/reperfusion and drug-mediated tissue injury, including both pre-treatment (in the case of a medical procedure) and treatment after ischemia/reperfusion and drug-mediated tissue injury has occurred.

D. Coagulation and Thrombosis

Coagulation is the biological process by which blood forms clots. A precise regulation mechanism prevents aberrant coagulation that results in an increased risk of bleeding (haemorrhage) or obstructive clotting (thrombosis). Histone administration in mice for example increases microvascular thrombosis with loss of the vascular barrier, which contributes to multiple organ dysfunction and failure.

Histones including H1, H2A, H2B, H3, and H4 induce platelet aggregation and subsequent platelet-dependent thrombin formation in vivo and in vitro. Of them, H4 has the strongest impact on platelet activity. Histones also induce a procoagulant phenotype in human platelets, which enhance thrombin generation and accelerate the blood clotting process. TLR2 and TLR4 are responsible for histone-mediated platelet activation through activation of signaling pathways (e.g., ERK, Akt, p38, and NF-κB), induction of calcium influx, and fibrinogen recruitment.

Histone-DNA complexes augment thrombin generation, whereas the administration of APC abolishes this process. Heparin and albumin neutralize histone toxicity as well as histone-related platelet activation in vitro and in vivo. In addition, histone infusion increases plasma levels of von Willebrand factor in mice, which contributes to platelet activation and subsequent development of deep venous thrombosis. Besides platelets, histones impair the protein C-thrombomodulin system. Exogenous histones dose dependently increase plasma thrombin generation in the presence of thrombomodulin. Interestingly, recombinant thrombomodulin (rTM), which has been approved for the treatment of disseminated intravascular coagulation patients in Japan, directly binds histone and protects mice against lethal thrombosis in mice. The protective effects of rTM against histone toxicity are mediated through both APC-dependent and -independent ways.

Patients suffering from coagulation and or thrombosis caused by extracellular histones have increased levels of extracellular histones present in their blood and these proteins have been implicated as important mediators of coagulation and or thrombosis pathology.

In an embodiment of the second or third aspect of the invention, there is provided a method of treating coagulation and thrombosis in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in coagulation and or thrombosis patients.

Thus, compounds of the invention and therapeutic or pharmaceutical compositions including said compounds provide a means for ameliorating the cytotoxic activity of extracellular histone proteins in coagulation and or thrombosis caused by extracellular histone proteins, including both pre-treatment (in the case of a medical procedure) and treatment after coagulation or thrombosis has occurred.

E. Autoimmune/Inflammatory Disease

The present invention contemplates the treatment of a variety of autoimmune and/or inflammatory disease states such as multiple sclerosis, spondyloarthropathy, ankylosing spondylitis, psoriatic arthritis, reactive arthritis, enteropathic arthritis, ulcerative colitis, Crohn's disease, irritable bowel disease, rheumatoid arthritis, juvenile rheumatoid arthritis, familial Mediterranean fever, amyotrophic lateral sclerosis, Sjogren's syndrome, early arthritis, viral arthritis, or psoriasis. The diagnosis and treatment of these diseases are well documented in the literature.

Histone have been implicated in several autoimmune and autoinflammatory diseases such as rheumatoid arthritis, systemic lupus, small-vessel vasculitis, and blood transfusion-related diseases. Besides acting as direct autoantigens in autoimmune disorders, extracellular histones can prevent DNA degradation through formation of histone-DNA complex, which enhances the autoimmune response. In addition, protein arginine deaminases (e.g., PDA4) mediate deimination and citrullination of histones, which in turn increase the immunogenicity of histones.

Patients suffering from autoimmune and/or inflammatory disease have increased levels of extracellular histones present in their blood and these proteins have been implicated as important mediators of autoimmune and/or inflammatory disease pathology.

In an embodiment of the second or third aspect of the invention, there is provided a method of treating autoimmune and/or inflammatory disease in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in autoimmune and/or inflammatory disease patients.

Thus, compounds of the invention and therapeutic or pharmaceutical compositions including said compounds provide a means for ameliorating the cytotoxic activity of extracellular histone proteins in autoimmune and/or inflammatory disease, including both pre-treatment (in the case of a medical procedure) and treatment after autoimmune and/or inflammatory disease has occurred.

F. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary oedema.

ARDS is caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI) including transfusion-related acute lung injury (TRALI).

ARDS can occur within 24 to 48 hours of an injury or attack of acute illness. In such a case the patient usually presents with shortness of breath, tachypnoea, and symptoms related to the underlying cause, i.e., shock. Long term illnesses can also trigger it, such as malaria. The ARDS may then occur sometime after the onset of a particularly acute case of the infection.

Patients suffering from ARDS can have increased levels of extracellular histones present in their blood and these proteins have been implicated as important mediators of ARDS pathology.

In an embodiment of the second, third or fourth aspects of the invention, there is provided a method of treating (either prophylactically or therapeutically) extracellular histone associated acute respiratory distress syndrome in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in ARDS patients.

Thus, compounds of the invention and therapeutic or pharmaceutical compositions including said compounds provide a means for ameliorating the cytotoxic activity of extracellular histone proteins in ARDS, including both pre-treatment (in the case of a medical procedure) and treatment after ARDS has occurred.

G. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments.

Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

Patients suffering from histone associated cardiovascular disease have increased levels of extracellular histones present in their blood and these proteins have been implicated as important mediators of histone associated cardiovascular disease pathology.

In an embodiment of the second, third or fourth aspects of the invention, there is provided a method of treating (either prophylactically or therapeutically) extracellular histone associated cardiovascular disease in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in histone associated cardiovascular disease patients.

Thus, compounds of the invention and therapeutic or pharmaceutical compositions including said compounds provide a means for ameliorating the cytotoxic activity of extracellular histone proteins in histone associated cardiovascular disease, including both pre-treatment (in the case of a medical procedure) and treatment after histone associated cardiovascular disease has occurred.

H. Retinal Detachment

Retinal detachment is a disorder of the eye in which the neural layer of the retina peels away from the retinal pigment epithelium, usually caused by a retinal break or tear. The intravitreal concentration of histones is higher in the eyes of patients with retinal detachment than in normal eyes.

Extracellular histones are toxic and induce IL-8 production in vivo and in vitro through a TLR4/MAPK (ERK1/2 and p38)-dependent pathway. Vitreous body hyaluronic acid decreases histone-mediated toxicity by inhibiting diffusion of histones. Thus, histones released from dying retinas can act as DAMPs to induce pro-inflammatory cytokine release and mediate cell toxicity.

Patients suffering from retinal detachment have increased levels of extracellular histones present in their blood and these proteins have been implicated as important mediators of retinal detachment pathology.

In an embodiment of the second or third aspect of the invention, there is provided a method of treating retinal detachment in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in retinal detachment patients.

Thus, compounds of the invention and therapeutic or pharmaceutical compositions including said compounds provide a means for ameliorating the cytotoxic activity of extracellular histone proteins in retinal detachment, including both pre-treatment (in the case of a medical procedure) and treatment after retinal detachment has occurred.

Thus, compounds of the invention and therapeutic or pharmaceutical compositions including said compounds provide a means for ameliorating the cytotoxic activity of extracellular histone proteins in burns subjects.

I. Fibrosis

Patients suffering from fibrosis have increased levels of extracellular histones present in their blood and these proteins have been implicated as important mediators of fibrosis pathology.

In an embodiment of the second or third aspect of the invention, there is provided a method of ameliorating histone induced cytotoxicity caused fibrosis in a subject, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in fibrosis patients.

Thus, compounds of the invention and therapeutic or pharmaceutical compositions including said compounds provide a means for ameliorating the cytotoxic activity of extracellular histone proteins in fibrosis in a subject, including both pre-treatment (in the case of a medical procedure) and treatment after fibrosis has occurred.

J. Diabetes

Patients suffering from diabetes can have increased levels of extracellular histones present in their blood and these proteins have been implicated as important mediators of diabetes pathology.

The invention provides methods for treating histone associated complications in diabetes (e.g. inflammation and delayed wound healing). The methods comprise administering a therapeutically effective amount of at least one compound of the invention to a subject diagnosed with Type 1, Type 1.5 or Type 2 diabetes.

In an embodiment of the second or third aspect of the invention, there is provided a method of ameliorating diabetes in a subject, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in diabetes patients.

In certain embodiments, the symptom of diabetes having histone involvement is inflammation. Reduction in inflammation can be monitored by physical examination, as well as the reduction in the presence of inflammatory markers.

In certain embodiments, a method for treatment of diabetes is provided, that comprises the administration of a therapeutically effective amount of an agent used to treat diabetes and at least one compound of the invention. The agent used to treat diabetes can be insulin or another agents selected from the following Biguanides, Metformin (Glucophage), Metformin liquid (Riomet), Metformin extended release (Glucophage XR, Fortamet, Glumetza), Sulfonylureas, Glimepiride (Amaryl), Glyburide (Diabeta, Micronase), Glipizide (Glucotrol, Glucotrol XL), Micronized glyburide (Glynase), Meglitinides, Repaglinide (Prandin), D-Phenylalanine Derivatives, Nateglinide (Starlix), Thiazolidinediones, Pioglitazone (TZDs), Pioglitazone, (Actos), DPP-4 Inhibitor, Sitagliptin (Januvia), Saxagliptin (Onglyza), Linagliptin (Tradjenta), Alpha-glucosidase, Acarbose (Precose), Miglitol (Glyset), Bile Acid Sequestrants, Colesevelam (Welchol), Pioglitazone & metformin (Actoplus Met), Glyburide & metformin (Glucovance), Glipizide & metformin (Metaglip), Sitagliptin & metformin (Janumet), Saxagliptin & metformin (kombiglyze), Repaglinide & metformin (Prandimet) and Pioglitazone & glimepiride (Duetact).

Thus, compounds of the invention and therapeutic or pharmaceutical compositions including said compounds provide a means for ameliorating the cytotoxic activity of extracellular histone proteins in diabetes in a subject. As such the present invention provides a treatment for diabetes in a subject, including both pre-treatment (in the case of a medical procedure) and treatment after diabetes has occurred.

K. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

Patients suffering from the side effects of various forms of cancer therapy, including chemotherapy, radiation, and cytokine therapy can have increased levels of extracellular histones present in their blood and these proteins have been implicated as important mediators of these side effects.

In an embodiment of the second or third aspect of the invention, there is provided a method of ameliorating the side effects of various forms of cancer therapy, including chemotherapy, radiation, and cytokine therapy in a subject by inhibiting the cytotoxic activity of extracellular histones, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment for the side effects of various forms of cancer therapy, including chemotherapy, radiation, and cytokine therapy.

In a highly preferred form of the invention the compound used in treating the side effects of various forms of cancer therapy, including chemotherapy, radiation, and cytokine therapy in the patients undergoing such therapy is the compound β-O-Methyl Cellobioside Sulphate or a pharmaceutically acceptable salt thereof. For example, the compound used in the method is Sodium β-O-Methyl Cellobioside Sulphate.

Thus, compounds of the invention and therapeutic or pharmaceutical compositions including said compounds provide a means for ameliorating the cytotoxic activity of extracellular histone proteins in the side effects of various forms of cancer therapy, including chemotherapy, radiation, and cytokine therapy, including both pre-treatment (in the case of a medical procedure) and treatment after these therapies have occurred.

L. Wound Healing

Also provided are methods for use in wound healing. As used herein "wound healing" refers to the intricate process where the skin (or another organ-tissue) repairs itself after injury. The classic model of wound healing is divided into three or four sequential, yet overlapping, phases: (1) haemostasis, when clot stops bleeding, (2) inflammation, (3) proliferation and (4) remodelling. Upon injury to the skin, a set of complex biochemical events takes place in a closely orchestrated cascade to repair the damage. During the inflammation phase, bacteria and cell debris are phagocytosed and removed from the wound by white blood cells. Platelet-derived growth factors (stored in the alpha granules of the platelets) are released into the wound that cause the migration and division of cells during the proliferative phase. The proliferation phase is characterized by angiogenesis, collagen deposition, granulation tissue formation, epithelialization, and wound contraction. New blood vessels are formed and fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue.

Patients suffering from wound healing difficulties can have increased levels of extracellular histones present in their blood and these proteins have been implicated as important mediators of wound healing pathology.

In an embodiment of the second or third aspect of the invention, there is provided a method of ameliorating histone induced cytotoxicity caused during wound healing in a subject, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in patients suffering from wound healing difficulties.

Thus, compounds of the invention and therapeutic or pharmaceutical compositions including said compounds provide a means for ameliorating the cytotoxic activity of extracellular histone proteins in treating wounds in a subject.

M. Histones in Central Nervous System Disease

Patients suffering from central nervous system disease can have increased levels of extracellular histones present in their blood and these proteins have been implicated as important mediators of central nervous system disease pathology. For example, Huntington's disease is an autosomal dominant neurodegenerative disorder caused by a polyglutamine repeat expansion, resulting in an expanded polyglutamine track in the huntingtin protein. Recent evidence indicates that histone modification-mediated transcriptional dysregulation is an important pathogenic mechanism in Huntington's disease.

The pharmacological manipulations of histone deacetylase activity have been beneficial in various experimental models of central nervous system disease such as Huntington's disease, epilepsy, and Alzheimer's disease. Neuronal death, inflammatory responses, and reactive gliosis are the markers of the major neurological diseases. More recent evidence indicates that extracellular histone H1 is a neurotoxic proinflammatory factor and causes reactive gliosis in central nervous system. These findings suggest that both histone modifications and extracellular histones contribute to central nervous system disease.

In an embodiment of the second or third aspect of the invention, there is provided a method of ameliorating histone induced central nervous system disease in a subject, said method comprising the step of: administering to the subject a therapeutically or pharmaceutically effective amount of a polyanionic sulfated cellobioside modified with a small uncharged glycosidically linked substituent at its reducing terminus or a pharmaceutically acceptable salt thereof. Preferably the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

Compounds such as mCBS can block the toxic effects of extracellular histones and thereby are useful as a treatment in central nervous system disease.

Thus, compounds of the invention and therapeutic or pharmaceutical compositions including said compounds provide a means for ameliorating the cytotoxic activity of extracellular histone proteins in central nervous system disease in a subject, including both pre-treatment (in the case of a medical procedure) and treatment after central nervous system disease has occurred.

3. Therapeutic and Pharmaceutical Forms

In a fifth aspect of the invention, there is provided a therapeutic or pharmaceutical composition for use in treating an extracellular histone associated complication comprising: at least a polyanionic sulfated cellobioside modified with a small uncharged glycosidically linked substituent at its reducing terminus or a therapeutically or pharmaceutically acceptable salt thereof. Preferably, the composition includes a therapeutically or pharmaceutically acceptable carrier, excipient and/or diluent. The compound in the therapeutic or pharmaceutic may be in a neutral free base form or salt form. Preferably, the compound is the sodium salt of β-O-Methyl Cellobioside Sulfate.

As used here, the terms "pharmaceutically acceptable" or "therapeutically effective" refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Methods for preparing administrable compositions are apparent to those skilled in the art, and are described in more detail in, for example, Remington's Pharmaceutical Science, 15th ed., Mack Publishing Company, Easton, Pa., hereby incorporated by reference in its entirety.

As used here, the term "pharmaceutically-acceptable carrier" or "a pharmaceutically acceptable excipient" or "pharmaceutically acceptable diluent" "therapeutically-acceptable carrier" or "a therapeutically acceptable excipient" or "therapeutically acceptable diluent" means a material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier, diluent and excipient must be "acceptable" in the sense of being compatible with the other ingredients of the formulation and not injurious to the patient. It is a material that is not biologically or otherwise undesirable i.e., the material can be applied to an individual along with the active agent without causing unacceptable biological effects or interacting in a deleterious manner with any one or more of the components of the composition in which it is contained. Some examples of materials that can serve as pharmaceutically-acceptable carriers, diluents and excipients include, but are not limited to: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, binding agents, fillers, lubricants, colouring agents, disintegrants, release agents, coating agents, sweetening agents, flavouring agents, perfuming agents, preservative, water, salt solutions, alcohols, antioxidants, polyethylene glycols, gelatin, lactose, amylose, magnesium stearate, talc, silicic acid, viscous paraffin, hydroxymethylcellulose, polyvinylpyrrolidone and the like can also be present in the formulation. The terms such as "excipient", "carrier", "diluent" and "pharmaceutically acceptable carrier" or the like are used interchangeably herein.

Examples of therapeutically or pharmaceutically acceptable carriers, excipients or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions described herein can additionally contain other adjunct components conventionally found in pharmaceutical compositions, at their art-established usage levels. Thus, for example, the compositions can contain additional, compatible, pharmaceutically-active materials such as, for example, antipruritics, astringents, local anaesthetics or anti-inflammatory agents. However, such materials, when added, should not unduly interfere with the biological activities of the components of the compositions described herein.

As described in detail below, the therapeutically or pharmaceutical acceptable compositions described herein can be specially formulated for administration in solid or liquid form, including those adapted for the following: (1) oral administration, for example, drenches (aqueous or nonaqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) injection directly into the organ needing treatment such as by intraparenchymal (into the brain), intrathecal, intraventricular or intrahepatic administration; (4) topical application, for example, as a cream, lotion, gel, ointment, or a controlled-release patch or spray applied to the skin; (5) in an aerosol form suitable for administration by inhalation, such as by intranasal inhalation or oral inhalation, (6) intravaginally or intrarectally, for example, as a pessary, cream, suppository or foam; (7) sublingually; (8) ocularly as an eye drop; (9) transdermally; (10) transmucosally; or (11) nasally.

In one embodiment, the composition of the invention is administered by injection such as by parenteral injection (such as by subcutaneous, intramuscular or intravenous injection) or locally to tissues and organs such as by intraparenchymal (into the brain), intrathecal, intraventricular or intrahepatic administration.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

Sterile injectable solutions can be prepared by incorporating the pharmaceutical composition of the invention in the required amount in an appropriate solvent with one or a combination of ingredients enumerated above, as required, followed by filtered sterilisation. By way of illustration, a single dose may be dissolved in 1 ml of isotonic NaCl solution and either added to 1000 ml of fluid or injected at the proposed site of infusion, (see for example, "Remington's Pharmaceutical Sciences" 15th Edition, pages 1035-1038 and 1570-1580).

In the case of injectable solutions, the carrier can be a solvent or dispersion medium containing, for example, water, Ringer's solution, isotonic saline, phosphate buffered saline, ethanol, polyol (for example, glycerol, propylene glycol (eg 1,2 propylene glycol), and liquid polyetheylene glycol, and the like), suitable mixtures thereof, and vegetable oils.

The proper fluidity can be maintained, for example, using a coating such as lecithin, by the maintenance of the required particle size in the case of dispersion and using surfactants. Prevention of the action of microorganisms can be achieved by including various anti-bacterial and or anti-fungal agents. Suitable agents are well known to those skilled in the art and include, for example, parabens, chlorobutanol, phenol, benzyl alcohol, ascorbic acid, thiomerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

In a second embodiment, the composition of the invention is administered orally, for example, with an inert diluent or an assimilable edible carrier. For oral therapeutic administration, the pharmaceutical composition may be incorporated with excipients and used in the form of ingestible tablets, buccal tablets, troches, capsules, elixirs, suspensions, syrups, wafers, and the like.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition, these oral formulations may contain suitable flavouring and colourings agents.

When used in capsule form the capsules may be coated with compounds such as glyceryl monostearate or glyceryl distearate which delay disintegration. Tablets, troches, pills, capsules and the like can also contain the following: a binder such as gum tragacanth, acacia, corn starch or gelatin; excipients such as dicalcium phosphate; an additional disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring.

When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both.

Liquid forms for oral administration (such as a syrup or elixir) can contain, in addition to the above agents, a liquid carrier, a sweetening agent (e.g. sucrose), a preservative (eg methyl and propylparabens), a dye and flavouring such as cherry or orange flavour. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like. The emulsions for oral administration may further comprise one or more emulsifying agents. Suitable emulsifying agents include dispersing agents as exemplified above or natural gums such as guar gum, gum acacia or gum tragacanth.

In a third exemplary embodiment, the composition of the invention is administered directly to the airways of a subject in the form of an aerosol or by nebulization. For use as aerosols, solution or suspension of the pharmaceutical acceptable compositions of the invention can be packaged in a pressurized aerosol container together with suitable propellants, for example, hydrocarbon propellants like propane, butane, or isobutane with conventional adjuvants. Such compositions can also be administered in a non-pressurized form such as in a nebulizer or atomizer.

Aerosols for the delivery to the respiratory tract are known in the art: see, for example, Adjei, A. and Garren, J. Pharm. Res., 1: 565-569 (1990); Zanen, P. and Lamm, J-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)).

In a fourth exemplary embodiment, the composition may be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which are incorporated herein by reference.

In addition, the therapeutic or pharmaceutical acceptable composition of the invention according to any aspect, embodiment or example described hereof, can be incorporated into sustained-release preparations and formulations. Such therapeutic or pharmaceutical compositions may further include a suitable buffer to minimise acid hydrolysis. Suitable buffer agent agents are well known to those skilled in the art and include, but are not limited to, phosphates, citrates, carbonates and mixtures thereof.

Compounds of the invention may also be administered in the form of a "prodrug". A prodrug is an inactive form of a compound which is transformed in vivo to the active form. Suitable prodrugs include esters, phosphonate esters etc, of the active form of the compound.

Additionally, compositions of the invention can be implanted into a patient or injected using a drug delivery system. Coated delivery devices can also be useful. See, for example, Urquhart, et al. (1984), Ann. Rev. Pharmacol. Toxicol. 24: 199-236; Lewis, ed. "Controlled Release of Pesticides and Pharmaceuticals" (Plenum Press, New York, 1981); U.S. Pat. Nos. 3,773,919; 6,747,014; and U.S. Pat. No. 3,270,960.

In certain embodiments, the compositions are delivered using a device, or bandage, used for example in the process of treatment of a wound.

The therapeutically effective amount of a pharmaceutical compositions disclosed herein for any particular subject will depend upon a variety of factors including: the toxicity and therapeutic efficacy of the pharmaceutical composition; the severity of the ailment; the age, body weight, general health, sex and diet of the patient; the time of administration; the route of administration; the rate of sequestration of the compositions; the duration of the treatment; drugs used in combination or coincidental with the treatment, together with other related factors well known in medicine.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

Data obtained from the cell culture assays and animal models described herein can be used in formulating a range of therapeutically effective dosages for use in humans. The dosage of such compounds lies preferably within a range of circulating concentrations that include the $ED_{50}$ with little or no toxicity. The dosage can vary within this range depending upon the dosage form employed and the route of administration utilized.

The amount of compound of the invention described herein which can be combined with a carrier material to produce a dosage form will generally be that amount of the compound which produces a therapeutic effect. Generally, out of one hundred percent, this amount will range from about 0.1% to 99% of compound, preferably from about 5% to about 70%, most preferably from 10% to about 30%.

The dosage can be determined by a physician and adjusted, as necessary, to suit observed effects of the treatment. By way of illustration only the compositions may be administered so that the pharmaceutical acceptable compositions is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg etc. It is to be further understood that the ranges intermediate to the given above are also within the scope of the methods and compositions described herein, for example, in the range 1 mg/kg to 10 mg/kg, dose ranges such as 2 mg/kg to 8 mg/kg, 3 mg/kg to 7 mg/kg, 4 mg/kg to 6 mg/kg etc.

Where the compound of the invention is mCBS or mCBS.Na the dosage may be from 10 to 800 µg/ml. Preferably, it is in the range of 50 to 500 µg/ml. More preferably the dosage is 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790 or 800 g/ml when administered to a human subject.

In certain examples of the invention an effective amount of the modified sulfated cellobioside compound is given as a single dose of administration. In certain examples, the dose is given repeatedly. That is treatment regimens will vary depending on the severity and type of disease, the overall health and age of the patient, and various other conditions to be considered by the treating physician. With respect to duration and frequency of treatment, it is typical for skilled clinicians to monitor subjects to determine when a treatment is providing therapeutic benefit, and to determine whether to increase or decrease dosage, increase or decrease administration frequency, discontinue treatment, resume treatment or make other alteration to treatment regimen.

Therapeutics or pharmaceutical acceptable compositions of the invention according to any aspect, embodiment or example described hereof, may be provided in a single bolus administration or in multiple doses or treatments and may also be applied by "continuous" therapy where a small amount of the therapeutic composition is provided continually over an extended time period.

Where multiple dosing is used in the treatment (including continuous therapy) the therapeutics or pharmaceutical composition will be administered by a dosing schedule that can vary from once a week to daily depending on several clinical factors, such as the subject's sensitivity to the modified sulfated cellobioside compound used in the therapeutic or pharmaceutical composition. The desired dose to be administered in such a regime can be delivered as a single dose at one time or divided into sub-doses, e.g., 2-4 sub-doses and administered over a time period, e.g., at appropriate intervals through the day or other appropriate schedule. Such sub-doses can be administered as unit dosage forms.

In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The desired dose can be administered using continuous infusion or delivery through a controlled release formulation. In that case, the pharmaceutical composition contained in each sub-dose must be correspondingly smaller to achieve the total daily dosage.

The dosage unit can also be compounded for delivery over several days, e.g., using a conventional sustained release formulation which provides sustained release of the pharmaceutical composition over a several day period. Sustained release formulations are well known in the art and are particularly useful for delivery of agents at a site, such as could be used with the agents described herein. In this embodiment, the dosage unit contains a corresponding multiple of the daily dose.

4. Combination Regimes

In certain exemplary embodiments, according to the fifth aspect of the invention, the identified composition may also comprise a second active agent, compound or composition selected from: one or more of anti-inflammatory agents, antibiotic agents, antiviral agents, antifungal agents and/or any other form of therapeutic or pharmaceutical compound that treats one or more conditions that the subject is afflicted with. According to this embodiment, the second active agent, compound or composition desirably provides an adjunct therapy for sepsis, SIRS and IRI or for a medical condition or disease associated with sepsis, SIRS and IRI. Preferably, the second active agent, compound or composition comprises one or more of anti-inflammatory agents.

Therapeutic advantages may be realised through combination regimens. In certain embodiments of the invention, the described methods may further comprise the step of: administering to a subject, at the same time or concomitantly with the inventive treatment, a second active agent that is an adjunct treatment for the sepsis, SIRS and IRI or the medical condition or disease associated with sepsis, SIRS and IRI that the patient is having or suffering from or is at risk of having or suffering from when delivered preventatively.

The second active agent may include, without limitation, anti-inflammatory agents, antibiotic agents, antiviral agents, antifungal agents or other forms of medical intervention that is distinct from the compound of the invention.

By way of illustration, when the method or treatment is directed to treating or ameliorating a septic or non-septic disease state involving extracellular histone mediated pathology in a subject the method may also comprise administering to a subject at the same time or concomitantly, a second anti-inflammatory agents, antibiotic agents, antiviral agents, antifungal agents or other forms of medical intervention that is distinct from the compound of the invention, which provides an adjunct treatment for a medical condition involving extracellular histone mediated pathology.

In one example, the second active agent provides an adjunct treatment or prevention for sepsis, SIRS or IRI or the medical condition or disease associated with the sepsis, SIRS or IRI such as a sepsis, SIRS or IRI or a medical condition or disease associated with the sepsis, SIRS or IRI involving extracellular histone mediated pathology in a subject.

In another example, the second active agent provides an adjunct treatment or prevention for a medical condition involving extracellular histone cytotoxicity.

By way of illustration, when the method of treatment is directed to treating or ameliorating a septic or non-septic disease state associated with sepsis, SIRS or IRI involving extracellular histone mediated pathology in a subject, the method may also comprise administering to a subject at the same time or concomitantly, a second anti-inflammatory agents, antibiotic agents, antiviral agents, antifungal agents or other forms of medical intervention that is distinct from the compound of the invention, which provides an adjunct treatment for a medical condition involving extracellular histone mediated pathology.

In some examples, the additional agent administered is an anti-inflammatory agent such as a steroid, corticosteroids, COX-2 inhibitor, non-steroidal anti-inflammatory agent (NSAIDs), aspirin or any combination thereof. More particularly, the additional agent administered may be an anti-inflammatory agent, selected from the group consisting of Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone, Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen;

Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium, and combinations thereof.

In some examples, the additional agent administered is an antibiotic agent such as kanamycin, actinomycin D, doxorubicin, bleomycin, mithramycin, aminoglycosides, ansamycins, carbacephems, carbapenems, cephalosporins, glycopeptides, lincosamides, macrolides, monobactams, penicillins, polypeptides, quinolones sulfonamides and/or tetracyclines.

In some examples, the additional agent administered is an antiviral agent such as a non-nucleoside reverse transcriptase inhibitor, nucleoside reverse transcriptase inhibitor (e.g. nucleoside analogues), protease inhibitor and/or a nucleotide analogue reverse transcriptase inhibitor.

In some examples, the additional agent administered is an antifungal agent such as an imidazole, triazole, thiazole, allylamine, and/or echinocandin compound.

In some examples, the additional agent administered is an agent to treat diabetes. Such agents include those agents known in the art for treatment of diabetes and or for having anti-hyperglycemic activities, for example, inhibitors of dipeptidyl peptidase 4 (DPP-4) (e.g., Alogliptin, Linagliptin, Saxagliptin, Sitagliptin, Vildagliptin, and Berberine), biguanides (e.g., Metformin, Buformin and Phenformin), peroxisome proliferator-activated receptor (PPAR) modulators such as thiazolidinediones (TZDs) (e.g., Pioglitazone, Rivoglitazone, Rosiglitazone and Troglitazone), dual PPAR agonists (e.g., Aleglitazar, Muraglitazar and Tesaglitazar), sulfonylureas (e.g., Acetohexamide, Carbutamide, Chlorpropamide, Gliclazide, Tolbutamide, Tolazamide, Glibenclamide (Glyburide), Glipizide, Gliquidone, Glyclopyramide, and Glimepiride), meglitinides ("glinides") (e.g., Nateglinide, Repaglinide and Mitiglinide), glucagon-like peptide-1 (GLP-1) and analogs (e.g., Exendin-4, Exenatide, Liraglutide, Albiglutide), insulin and insulin analogs (e.g., Insulin lispro, Insulin aspart, Insluin glulisine, Insulin glargine, Insulin detemir, Exubera and NPH insulin), alpha-glucosidase inhibitors (e.g., Acarbose, Miglitol and Voglibose), amylin analogs (e.g. Pramlintide), Sodium-dependent glucose cotransporter T2 (SGLT T2) inhibitors (e.g., Dapgliflozin, Remogliflozin and Sergliflozin) and others (e.g. Benfluorex and Tolrestat).

Those skilled in the art will appreciate that the compositions according to any aspect, embodiment or example described hereof may be administered as part of a combination therapy approach to the treatment of sepsis, SIRS or IRI or a disease or condition associated with sepsis, SIRS or IRI. In combination therapy, the respective agents may be administered simultaneously, or sequentially in any order. When administered sequentially, it may be preferred that the components be administered by the same route.

In some examples where the two agents are applied separately, one would generally ensure that a significant time period did not expire between the time of each delivery, such that both agents would still be able to exert an advantageously combined effect. In such instances, it is contemplated that one would typically administer both modalities within about 12-24 hours of each other and, more preferably, within about 6-12 hours of each other, with a delay time of only about 12 hours being most preferred, in some situations, it may be desirable to extend the time for treatment significantly, however, where several days (2, 3, 4, 5, 6 or 7) to several weeks (1, 2, 3, 4, 5, 6, 7 or 8) lapse between the respective administrations. It also is conceivable that more than one administration of a drug will be desired.

When compositions of the invention, and a second active agent are administered in different compositions, routes of administration may be different. For example, the composition of the invention is administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration, and the second pharmaceutically active agent is administration by a different route, e.g. a route commonly used in the art for administration of said pharmaceutically active agent. In a non-limiting example, the compositions of the invention can be administered by injection, while the second active agent can be administrated orally.

5. Manufacture of a Medicament

In a sixth aspect of the invention, there is provided a use of a therapeutically or pharmaceutically effective amount of a polyanionic sulfated cellobioside modified with a small uncharged glycosidically linked substituent at its reducing terminus or a pharmaceutically acceptable salt thereof, in the manufacture of a medicament for treating a medical condition, ailment or disease involving extracellular histones. Preferably, the small uncharged glycosidically linked substituent that is present at the reducing terminus of the polyanionic sulfated cellobioside improves the chemical stability of the polyanion relative to the same polyanion that is sulfated at its reducing terminus. More preferably, the modified sulfated cellobioside is mCBS or more particularly is a pharmaceutically acceptable salt thereof such as mCBS.Na.

For example, in an embodiment of the sixth aspect of the invention, there is provided a use of a therapeutically or pharmaceutically effective amount of a polyanionic sulfated cellobioside modified with a small uncharged glycosidically linked substituent at its reducing terminus or a pharmaceutically acceptable salt thereof, in the manufacture of a medicament for the treatment or prevention of sepsis or an IRI or a medical condition or disease associated with sepsis, SIRS or IRI in a subject. Preferably, the modified sulfated cellobioside is mCBS or more particularly is a pharmaceutically acceptable salt thereof such as mCBS.Na.

In one embodiment of such use, the medicament is for the treatment of sepsis or SIRS or of a medical condition or disease associated with sepsis or SIRS in a subject, wherein said treatment ameliorates or inhibits said sepsis or SIRS or said condition or disease associated with said sepsis or SIRS.

In another embodiment of such use, the medicament is for the treatment of an IRI or of a medical condition or disease associated with an IRI in a subject, wherein said treatment ameliorates or inhibits said the IRI or said condition or disease associated with said injury.

In yet another embodiment of such use, the medicament is used to neutralise extracellular histones that (i) are cytotoxic towards the endothelium in a subject, or (ii) contribute to endothelial dysfunction in a subject, or (iii) initiate coagulation by activating platelets in a subject, or (iv) induce red cell fragility and resultant anaemia in a subject.

In yet another embodiment, the manufactured medicament may also include a therapeutic or pharmaceutically effective amount of a second active agent, compound or composition. According to this embodiment, the second active agent, compound or composition provides an adjunct therapy for treating a medical condition, ailment or disease involving extracellular histones. Desirably, the second active agent, compound or composition provides an adjunct therapy for the treatment of sepsis, SIRS or IRI or for a medical condition or disease associated with sepsis, SIRS or IRI. Preferably, the second active agent is selected from: one or more of anti-inflammatory agents, antibiotic agents, anti-viral agents, antifungal agents and/or any other form of therapeutic or pharmaceutical compound that treats one or more conditions that the subject is afflicted with. More preferably, the second active agent, compound or composition comprises one or more of anti-inflammatory agents.

When the modified sulfated cellobioside compound is used in any of the methods of the invention the compound can be administered or formulated for administration to the subject in need thereof, in a single dose of formulation. In certain alternative embodiments, the modified sulfated cellobioside compound is administered, or formulated for administration to the subject in need thereof, as a multi-dose formulation.

Preferably, for administration to a subject, the therapeutic or pharmaceutical composition is provided as a pharmaceutically acceptable composition. When in this form, (1) the composition will be pharmaceutical formulated together with one or more pharmaceutically acceptable carriers (additives) and/or diluents and/or excipients and (2) the modified sulfated cellobioside compound in the composition may be formulated in a neutral or salt form.

EXAMPLES

The present invention is described further in the following non-limiting example which is provided by way of illustration only, and should not be construed as limiting the generality of the disclosure of the description throughout this specification.

Example 1: Method for the Preparation of mCBS•Na

β-O-methyl cellobioside is prepared as described by Jon K Fairweather et al., 2004, *Aust. J. Chem.*, 57: 197-205.

β-O-methyl cellobioside sulfate (mCBS) and sodium β-O-methyl cellobioside sulfate (mCBS.Na) compounds were prepared as described by Katrin C Probst and Hans Peter Wessel, 2001, *J. Carbohydrate Chemistry*, 20 (7 & 8): 549-560, the disclosure of which is hereby incorporated herein by reference in its entirety.

β-O-methyl cellobioside sulfate (mCBS) was prepared according to the following schematic

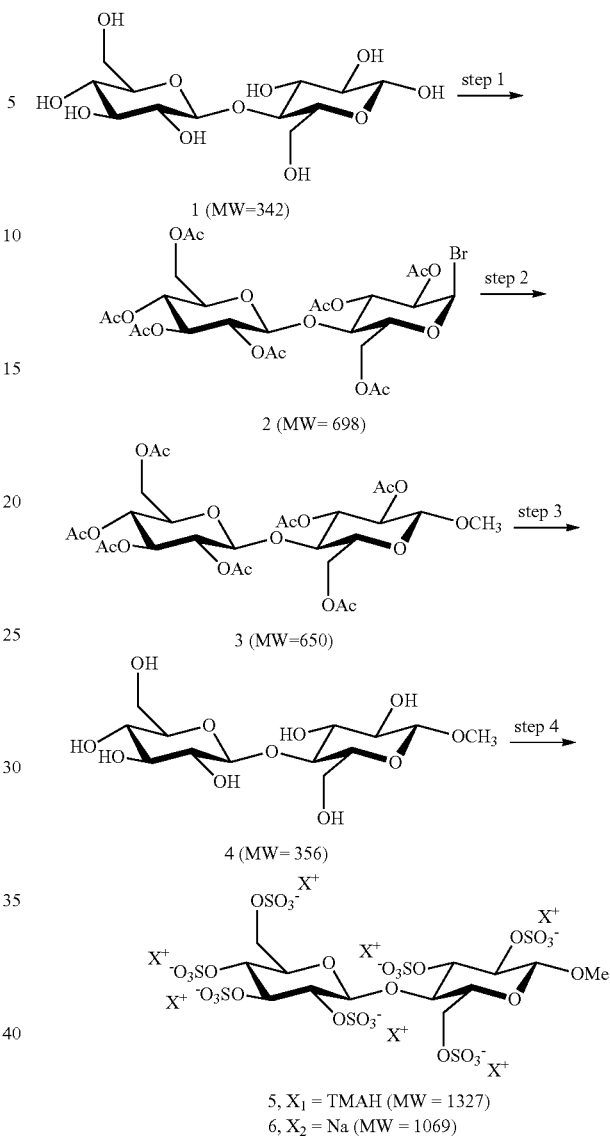

Step 1: To the mixture of α-D-cellobiose 1 (116 g, 338 mmol) and glacial acetic acid (1.6 L) was added acetyl bromide (300 mL, 500.0 g, 4065 mmol, 12.0 equiv) at room temperature. The resulting creamy mixture was heated at 60° C. for 45-55 mins until the reaction mixture turn to be a clear solution which indicate the completion of reaction.

Carefully pour the hot solution into the beaker (10 L) containing the cracked ice (4 kg). Stir the mixture until the white solid precipitated (~10 min). Add another portion of cold water (1 L) and keep on stirring for 10 min.

Filter with sinter funnel and washed the solid with cold water (700 mL×3). The resulting solid in the funnel was dissolved in DCM (1 L) and washed the funnel with DCM (300 mL×2). The combined DCM layer was washed with brine (1.5 L) and back extracted with DCM (0.5 L). The final DCM layer was dried over $Na_2SO_4$, filtered and concentrated under reduce pressure at <35° C. within 2 h to obtain the target bromide 2 (172.5 g, 74.3% yield) which was directly used for the following glycosylation.

Step 2: To the mixture of per-O-acetylated cellobiosyl bromide 2 (171 g, 250 mmol), anhydrous DCM (800 mL), anhydrous MeOH (800 mL), activated 3A molecular sieves (70 g) was added silver carbonate ($Ag_2CO_3$, 75 g, 275 mmol, 1.1 equiv). The resulting mixture was stirred in the absence of light for 16 h. The mixture was purified through a plug of silica and eluted with EtOAc. The collected fractions were concentrated to give the crude product as the brown solid which was directly used for the next step. The $R_f$ of compound 3=0.28 (EtOAc-Hexane, 1:1).

Step 3: To the mixture of the crude product obtained from step 2 and anhydrous MeOH (1 L) was added a small piece of Na (1.72 g, 0.3 equiv, 75 mmol) at room temperature. Shortly afterwards, a white solid began to precipitate from solution. The resulting mixture was stirred overnight in order to ensure the completion of de-acetylation. The final suspension was filtered and washed with MeOH (300 mL×2). The white solid was collected and dried under vacuum for overnight to obtain the final cellobioside 4 (72.5 g, 81.4% over 2 steps).

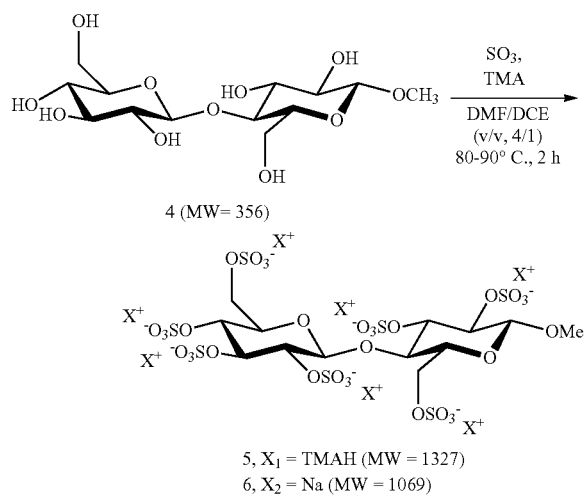

Synthetic and Purification Procedure for Step 4:

Step 4 The mixture of compound 4 (84.0 g, 236 mmol), $SO_3$·TMA (367.4 g, 2.64 mol, 11.2 equiv), anhydrous DMF (3140 mL) and anhydrous DCE (767 mL) was degassed under Ar for three times and heated at 80-90° C. for 2 h. (Reaction monitoring: After heating for 10 min, the creamy mixture turned to be a clear solution. After 30 m, the solution became cloudy again. After 50 min, the aggregated solid was observed on the surface of flask.) Upon cooling, the resulting mixture was moved to the cold room (~5° C.) and settled overnight which allows the solid to completely aggregate from the solvent. The complete conversion from compound 4 into 5 was confirmed with 1H-NMR. Decant the solution into the drain. The crude solid was filtered and washed with DCM for a couple of times. The resulting solid was dissolved in de-ionized water and directly subjected to ion-exchange column [Na form of DOWEX 50Wx8: 3 kg of resin ($H^+$ form) was pre-packed in glass gravity column, regenerated by elution of 1M NaOH (~6 L) and neutralized with de-ionized water (~12 L)]. The collected fractions were concentrated to yield the final sulfated cellobioside 6 (232.1 g, 92.0%) as the glassy solid.

Example 2: mCBS•Na Compound Stability Studies

Figure 1:
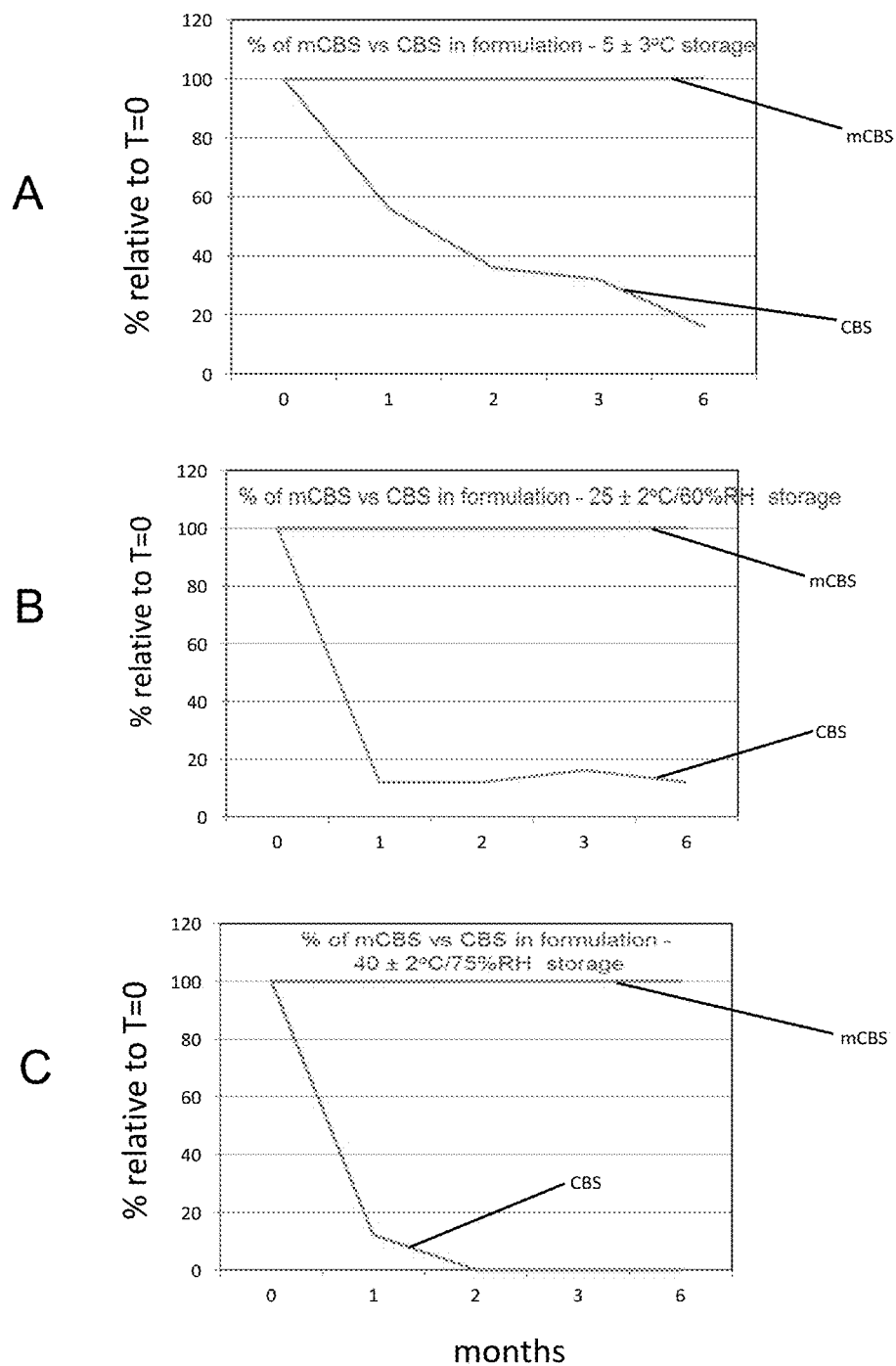
FIG. 1 comparison of stability of CBS against mCBS when stored at 5±3° C.

Stability studies were carried out at 5±3° C., 25±2° C./60% RH and 40±2° C./75% RH ° C. conditions. Levels of both mCBS and cellobiose sulfate (CBS) were tracked in formulated clinical material (i.e. mCBS in phosphate buffer) via HPLC. Graphing the percent (%) change of mCBS and CBS relative to their starting amount (at T=0), revealed that overtime, the level of mCBS was very stable. In contrast, the level of CBS drops very rapidly and is almost gone by around 3 months. The stability profile in fact is similar at accelerated conditions (i.e. 25±2° C./60% RH and 40±2° C./75% RH) and the rate of CBS disappearance appears to be faster. An example of the differences in stability of mCBS vs CBS from 2 lots of formulations are shown in FIG. 1. These data indicate that CBS is highly unstable in aqueous solutions but the addition of a methyl group to the reducing terminus of CBS results in a molecule (mCBS) that is very stable in aqueous solutions.

In addition, various mCBS formulation were tested in stability trials. The data of these experiments revealed the stability of mCBS did not differ with buffers used. Table 1 shows the composition of the various formulation of mCBS with respect to the buffers used.

TABLE 1

Composition of the buffer system

| Buffer System | Ingredients | Quantity | pH | Concentration of mCBS•Na |
|---|---|---|---|---|
| Phosphate Buffer | Disodium Hydrogen Phosphate | 1.35 mg/ml | 7.4-7.6 | 80 mg/ml |
|  | Monobasic sodium Phosphate | 0.33 mg/ml |  |  |
| Citrate Buffer | Sodium Citrate dihydrate | 10 mg/ml |  |  |
|  | 1M Citric acid | q.s for pH adjustment |  |  |
| Acetate Buffer | Sodium acetate | 1.20 mg/ml |  |  |
|  | Acetic acid | q.s for pH adjustment |  |  |

Table 2a shows that the pH varies overtime depending buffering capacity of the various formulation and it shows the pH of formulation with acetate buffer does not stay at around pH 7.5 even at around 5±3° C., but the data itself does indicate differences in mCBS stability during this period.

TABLE 2a pH during stability study

| Buffer | Condition | Day 0 | Day 3 | Day 7 | Day 14 | Day 21 | Day 28 |
|---|---|---|---|---|---|---|---|
| Phosphate buffer | 5 ± 3° C. | 7.58 | 7.28 | 7.19 | 7.14 | 7.13 | 7.14 |
|  | 25° C./60% RH |  | 7.27 | 7.21 | 7.14 | 7.18 | 7.22 |
|  | 40° C./75% RH |  | 7.28 | 7.19 | 7.15 | 7.09 | 7.10 |
| Citrate Buffer | 5 ± 3° C. | 7.60 | 7.27 | 7.24 | 7.15 | 7.15 | 7.17 |
|  | 25° C./60% RH |  | 7.22 | 7.18 | 7.15 | 7.18 | 7.30 |
|  | 40° C./75% RH |  | 7.20 | 7.20 | 7.12 | 7.12 | 7.17 |

TABLE 2a-continued pH during stability study

| Buffer | Condition | Day 0 | Day 3 | Day 7 | Day 14 | Day 21 | Day 28 |
|---|---|---|---|---|---|---|---|
| Acetate | 5 ± 3° C. | 7.5 | 6.97 | 7.02 | 6.94 | 6.93 | 6.92 |
| Buffer | 25° C./60% RH | | 7.00 | 7.02 | 7.10 | 7.15 | 7.38 |
| | 40° C./75% RH | | 6.87 | 6.89 | 6.81 | 6.81 | 6.84 |
| Control | 5 ± 3° C. | 6.82 | 6.81 | 6.81 | 6.84 | 6.79 | 6.89 |
| (i.e. | 25° C./60% RH | | 7.04 | 7.18 | 7.32 | 7.43 | 7.41 |
| unbuffered) | 40° C./75% RH | | 7.03 | 7.16 | 7.10 | 7.20 | 7.29 |

Table 2b compares mCBS vs CBS levels in a representative batch of bulk powder when stored at −20° C. over 24 months. T is for time in months. T=0 or T0 represents analytical results carried out on completion of manufacture. Subsequent analysis indicated are relative to the initial analysis of the drug powder or formulation (e.g. T1=one month from date of manufacture). Analytical method employing CAD (Charged Aerosol Detector) was used to measure the level of mCBS purity and its impurities and expressed as CAD %.

TABLE 2b

| | T0 | T1 | T3 | T6 | T9 | T12 | T18 | T24 |
|---|---|---|---|---|---|---|---|---|
| mCBS | 98.56 CAD % | 98.45 CAD % | 98.28 CAD % | 98.22 CAD % | 97.77 CAD % | 98.00 CAD % | 97.94 CAD % | 98.26 CAD % |
| CBS* | 0.23 CAD % | 0.25 CAD % | 0.28 CAD % | 0.32 CAD % | 0.36 CAD % | 0.36 CAD % | 0.36 CAD % | 0.29 CAD % |

*calculated as the sum of the α and β anomers.

Table 2c compares mCBS vs CBS levels in a representative batch of phosphate buffered pH 7.5 clinical trial material formulation when stored at 2-8° C. for over 18 months.

TABLE 2c

| | T0 | T2 | T3 | T7 | T10 | T13 | T19 |
|---|---|---|---|---|---|---|---|
| mCBS | 98.33 CAD % | 98.39 CAD % | 98.37 CAD % | 98.54 CAD % | 98.47 CAD % | 98.44 CAD % | 98.78 CAD % |
| CBS* | 0.25 CAD % | 0.03 CAD % | 0.07 CAD % | 0.03 CAD % | 0.04 CAD % | 0.04 CAD % | <0.03 CAD %† |

*calculated as the sum of the α and β anomers,
†Below limit of detection

The above tables 2b and 2c show the level mCBS and CBS in either the powder or solution after storage in various conditions for 18-24 months. CBS appears as a low-level impurity in these preparations. The results show CBS appear to be stable in powder when stored at −20° C. as the level does not appear to significantly change over time. However, in aqueous buffered solution, CBS is highly unstable with the level reduced to 0.03 CAD % (i.e. detection limits) within 3-6 month of storage at 2-8° C. In contrast the levels of mCBS did not appear to vary significantly over time and appears to show high stability when stored in powder or solution.

HPLC analysis after 28 days (Table 3) of mCBS in various buffer formulation was also carried out. mCBS appears to vary by only −/+~2% of nominal after 28 days in either phosphate or citrate buffer even at accelerated condition 25±2° C./60% RH and 40±2° C./75% RH indicating good stability.

TABLE 3

HPLC analysis results

| Buffer System and stability condition* | Day | Indicated Conc. Of mCBS•Na (mg/ml) | Amount of sample assayed (μl) | % Detected (n = 3) |
|---|---|---|---|---|
| Phosphate Buffer (40° C.) | 28 | 80 | 50 | 97.53 ± 2.42 |
| Phosphate Buffer (25° C.) | 28 | 80 | 50 | 98.68 ± 3.69 |
| Citrate Buffer (40° C.) | 28 | 80 | 50 | 101.25 ± 3.18 |
| Citrate Buffer (25° C.) | 28 | 80 | 50 | 102.53 ± 3.57 |
| Acetate Buffer (40° C.) | 28 | 80 | 50 | —* |
| Acetate Buffer (25° C.) | 28 | 80 | | |

—*: Not done;. 25° C. and 40° C. denotes 25 ± 2° C./60% RH or and 40 ± 2° C./75% RH (respectively)

Pre-Clinical Animal Studies of Toxicity and Pharmacokinetics Profile of β-O-methyl cellobioside Sulfate Compounds The following working Examples 3 to 10 outline exemplary pre-clinical studies in animals conducted by the inventors of the toxicity and pharmacokinetics (PK) profile of β-O-methyl cellobioside sulfate compounds used in the present invention.

Example 3: mCBS•Na Compound Employed in Animal Studies

This example demonstrates properties of the sodium β-O-methyl cellobioside sulfate (mCBS-Na) compound employed in the subsequently described toxicity and PK studies conducted in animals.

The STX studies described below were carried out inter alia to provide a preliminary understanding of the toxicity and PK profile of β-O-methyl cellobioside sulfate compounds such as mCBS-Na utilised in the present invention. These studies were carried out using the same lot of compound, the properties of which are summarised in the Table 4 below.

TABLE 4

Properties of mCBS•Na compound used in animal toxicity and PK studies

| Name: | Sodium β-O-Methyl Cellobioside Sulfate (mCBS•Na) |
|---|---|
| Molecular weight | 1070.6 daltons |
| Molecular formula | $C_{13}H_{17}Na_7O_{32}S_7$ |
| Purity | >96% |
| Description | 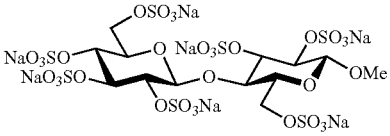 |
| Storage Conditions | 2-8° C. (powder) |
| Solubility in Vehicle | ~250 mg/mL in water/aqueous |
| Stability in Vehicle | Test item formulations were discarded after use. |

Example 4: Dose and Concentrations of β-O-Methyl Cellobioside Sulfate

In general, the sodium salt of mCBS was used in the toxicity and PK animal studies described herein. It should be noted however, that the bioanalytical measurement outlined herein detected and reported the mCBS free base form. Accordingly, for clarity, dose/concentrations have also been reported herein as the free base to make clear the relationship with the bioanalytical results. The mCBS free base doses were derived by correcting for sodium content (based on ratio of MW of free base to salt form) and purity of the Test Item. However, neither dose (i.e. sodium salt or free base) take into account the potency of the compound in the batch.

Example 5: Potency of β-O-Methyl Cellobioside Sulfate

As mentioned above, the reported doses administered to the animals or concentrations of mCBS were not corrected for potency (i.e. water content and other impurities) since potency analysis of the sodium salt of mCBS (i.e., mCBS-Na) in the batch used was not determined during the time the studies were being carried out. Subsequent analysis of the batch used in these studies have since shown that the potency of the sodium salt was ~74.5%. It is very likely that the actual dose used in these working examples were less than what were indicated.

Example 6: Toxicity of mCBS Following Intravenous Administration to Sprague Dawley Rats This example demonstrates an assessment of the acute toxicity of mCBS following intravenous administration of a single bolus dose to Sprague Dawley rats in a one week Dose Range Finding (DRF) study, as well as assessment of the toxicity of mCBS following daily intravenous administration of a bolus dose to Sprague Dawley rats for seven days.

These studies originally examined the dose of mCBS-Na and mCBS as free base. From the potency assessment, it is likely that the Maximum Tolerated Dose (MTD) estimate was ~745 mg/kg of sodium salt of mCBS or ~600 mg/kg of mCBS free base.

Assessment of the Acute Toxicity of β-O-methyl cellobioside sulfate (mCBS) Following Intravenous Administration of a Single Bolus Dose to Sprague Dawley Rats in a One Week Dose Range Finding (DRF) Study.

This study examined acute toxicity from single IV administration of mCBS in rats with doses up to 1000 mg/kg.

The acute toxicity of β-O-methyl cellobioside sulfate (mCBS) was assessed in Sprague Dawley rats following intravenous administration of a single bolus dose. A total of five groups of n=3 adult female rats were treated with 10, 30, 100, 300 and 1000 mg/kg doses of mCBS test item in the form of the sodium salt (mCBS-Na) in this dose range finding study. With correction for purity and sodium content, these dose levels corresponded to approximately 8.2, 24.5, 81.5, 244.5 and 815 mg/kg of the mCBS free base. The rats were then observed for 7 days prior to termination without necropsy. The mCBS test item treatments were well tolerated at all dose levels, up to and including the 1000 mg/kg dose. There were no findings considered to be related to treatment.

Therefore, Maximum Tolerated Dose (MTD) or the acute tolerated dose for mCBS-Na from this study was identified as 1000 mg/kg which corresponds to 815 mg/kg of mCBS free base. No abnormal findings or change in body weights (compared to control animals) was observed.

Assessment of the Toxicity of β-O-methyl cellobioside sulfate (mCBS) Following Daily Intravenous Administration of a Bolus Dose to Sprague Dawley Rats for Seven Days.

This study examined toxicity from repeat IV administration of mCBS in rats over 7 days with doses up to 1000 mg/kg.

The acute tolerability and toxicity of β-O-methyl cellobioside sulfate was assessed in Sprague Dawley rats following daily intravenous dose administration for a period of seven days. A total of four groups of n=3 adult female rats were treated with 0, 100, 300 and 1000 mg/kg doses of mCBS in the form of the sodium salt (mCBS-Na) in this repeated dose study. With correction for purity and sodium content these dose levels correspond to approximately 81.5, 244.5 and 815 mg/kg of the mCBS free base. The rats were then observed for 7 days prior to termination with gross necropsy and terminal haematology and biochemistry analyses. An additional group of n=3 male rats were also treated at the highest dose of 1000 mg/kg according to the same study design.

mCBS was well tolerated at all dose levels, up to and including the 1000 mg/kg dose. There were no adverse findings considered to be related to treatment. Hematology and biochemistry parameters in treated animals were unremarkable. Effects observed in gross necropsy and pathology was not considered to be treatment related.

Therefore, MTD in this study is identified as 1000 mg/kg which corresponds to 815 mg/kg of mCBS free base.

Example 7: Pharmacokinetic of mCBS Following Intravenous Administration to Sprague Dawley Rats This example demonstrates an assessment of the pharmacokinetic (PK) of mCBS administered intravenously to Sprague Dawley rats.

The following studies document the doses of mCBS reported as both the sodium salt and free base of mCBS. The latter is considered important especially when relating the measured plasma levels of mCBS (free base) to the administered dose and to determine the terminal phase PK parameter such as clearance (Cl) and volume of distribution (Vz). The STX-09 study documents the plasma concentration of mCBS over 5 hours of continuous infusion in rats at ~25 and 50 mg/kg/hr.

A Pharmacokinetic Study of β-O-methyl cellobioside sulfate Administered Via the Intravenous Route to Sprague Dawley Rats This study examines bolus IV administration (20 mg/kg) PK profile of mCBS in Sprague Dawley rats, and demonstrate that most of the compound is rapidly excreted with over 90% of administered dose being removed from the central compartment in the first 4 hours and the remaining mCBS administered dose slowly is removed over a longer period of time. The large volume of distribution indicates that the mCBS compound is rapidly moved from the central compart to the tissues.

The pharmacokinetics of β-O-methyl cellobioside sulfate (mCBS) were assessed in Sprague Dawley rats following intravenous administration of a bolus dose of 20 mg/kg as sodium salt of mCBS in the form of the heptasodium salt (mCBS-Na) (or 16.3 mg/kg of the free base after adjusting for sodium content and purity).

Taking potency into account, the dose administered to the rats estimated was likely to be 14.9 mg/kg and 12.65 mg/kg of the sodium salt and free base, respectively. Since corrected mCBS free base dose was approximately 20% lower, this effectively reduced the calculated clearance (Cl) and volume of distribution (Vz) values by a similar proportion.

A total of ten blood samples were collected from three rats at time points ranging from pre-dose to 48 hours post-dose. The resulting blood samples were processed to plasma and subsequently analysed for the concentration of mCBS (free-base) using an LC-MS/MS based method. The plasma concentration versus time data were used for calculation of pharmacokinetic parameters.

The mean (±SEM) value for the mCBS concentration at time zero (C0) was 73400 (±8560) ng/mL. The mean (±SEM) values for the area under the curve from time zero to the last measured time point (AUClast), and to infinity (AUCinf) were 34300 (±2460) ng·h/mL and 35000 (+2940) ng·h/mL, respectively. The mean (±SEM) value for the apparent elimination half-life (T1/2) was 77.5 (±54.5) h, but the mean (±SEM) value for the mean residence time (MRT) was relatively short at 5.58 (±3.99) h. The mean (±SEM) value for the volume of distribution (Vz) was high at 46.9 (±30.7) L/kg, while the mean (±SEM) value for total body clearance (Cl) was low at 0.472 (+0.0377) L/h/kg. The high inter-subject variability for $T_{1/2}$ (122% CV), Vz (113% CV), and MRT (124% CV) most likely resulted from incomplete characterization of the terminal elimination portion of the log linear concentration versus time curve.

A Pharmacokinetic Study of mCBS Administered Via the Intravenous Route to Sprague Dawley Rats This study examined PK of mCBS after bolus IV administration (100 mg/kg) in Sprague Dawley rats.

The pharmacokinetics of mCBS were assessed in Sprague Dawley rats following intravenous administration of a bolus 100 mg/kg dose of mCBS in the form of the sodium salt (or 81.5 mg/kg of the free-base—after correcting for sodium content and purity) to a group of 6 rats.

Taking potency into account, the dose administered to the rats was estimated to be 74.5 mg/kg and 63.25 mg/kg of the sodium salt and free base, respectively. Since corrected mCBS free base dose was approximately 20% lower, this effectively reduced the calculated clearance (Cl) and volume of distribution (Vz) values by a similar proportion.

A total of nine blood samples were collected from each rat at time points ranging from pre-dose to 192 hours post-dose. Urine samples were also collected over the first 48 hours. The resulting blood samples were processed to plasma. The urine and plasma samples were subsequently analysed for the concentration of mCBS (free-base) using LC-MS/MS based methods.

Plasma pharmacokinetic parameter estimates for mCBS were derived from the pooled mean concentration versus time data. The concentration at time zero (C0) was 308,000 ng/mL. The area under the curve from time zero to the time of the last measured concentration (AUClast) and when extrapolated to infinity (AUCinf) were both 135,000 ng·h/mL. The apparent terminal elimination half-life (T1/2) was 56.1 h, in contrast to the mean residence time (MRT) of 1.43 h. The compound showed a relatively high volume of distribution (Vz) of 49.0 L/kg while terminal total body clearance (Cl) was relatively low at 0.605 L/h/kg.

Urinary pharmacokinetic mass balance estimates for mCBS free-base were derived from the urinary amount excreted data. The mean (±SEM) values for percent of total dose of mCBS excreted in the 0-4 h, 0-24 h, and 0-48 h post-dosing collection intervals were 52.0 (±5.0) %, 65.0 (±7.0) %, and 69.2 (±10.8) %, respectively. Urinary excretion is identified as a major route for elimination of the compound in the first 48 hours post-administration.

The study confirmed that mCBS is rapidly cleared from the central compartment immediately after administration and absorbed by the tissues as shown by the large volume of distribution. The distribution half-life of the compound (which is a major determinant of elimination) was estimated to be 0.65 hr. Multiple sampling of the terminal phase improved the characterisation of terminal elimination half-life which was calculated to be ~56 h. A pharmacokinetic study in Sprague Dawley rats with mCBS administered by Intravenous Infusion This Study Examined the Plasma Concentration of mCBS Over 5 Hours of Continuous Infusion in Rats at ~25 and 50 mg/kg/Hr.

The pharmacokinetics (PK) of mCBS were studied following intravenous administration as an infusion over a 5 hours period to male Sprague Dawley rats. In this study the pharmacokinetics of the mCBS compound were investigated following intravenous infusion. The compound was formulated using Hartman's solution and administered to a group of n=3 rats at the rate of 25.3 mg/kg/h (total dose: 126.5 mg/kg; Group 1) and to a second group of n=3 rats at the rate of 50.6 mg/kg/h (total dose: 253 mg/kg; Group 2).

In this study, the nominal dose of mCBS sodium salt used for continuous infusion over 5 hours was 40 and 80 mg/kg/hr (or 34 and 68 mg/kg/hr respectively, as the free base).

A total of six blood PK samples were collected from each rat at time points ranging from pre-dose to 5 hours after the start of the infusion. The resulting blood samples were processed to plasma, and subsequently analysed for the concentration of mCBS using an LC-MS/MS based method. Phoenix 64 WinNonlin® software was used to estimate area under the concentration versus time curve (AUC) values over the 0 to 5 h infusion interval. Values for concentration at steady state (Css) and clearance (Cl) were also estimated.

Concentrations of mCBS were below the lower limit of quantification of the assay in plasma samples collected prior to dose administration and concentrations were quantifiable in all plasma samples collected from 30 min to 5 hours post-dose. Mean (±SEM) AUC values for the 0-5 h infusion interval were 260,000 (±30,200) ng·h/mL and 532,000 (±25,500) ng·h/mL for Groups 1 and Group 2, respectively. Mean (±SEM) values of Css and Cl for Group 1 were 58,400 (±6,920) ng/ml and 0.601 (±0.081) 1/h/kg for Group 1, while mean (±SEM) values of Css and Cl for Group 2 were 120,000 (±5,560) ng/ml and 0.571 (±0.025).

These results demonstrate that mCBS reached steady state plasma level (Css) after 2 hr of infusion. Both Css and AUC in the rats treated with 50 mg/kg/hr are both 2-fold higher compared to rats treated with 25 mh/kg/hr indicating that the systemic exposure are proportional to the dose used in the study. Coagulation tests showed that rats treated with higher dose of mCBS had higher APTT score compared to the reference range indicating the presence of mCBS at this dose increases clotting time.

Example 8: In Vitro Investigation of mCBS Binding to Plasma Proteins and Metabolism in Humans, Dogs and Rats This example demonstrates in vitro studies carried out to look at the metabolism and plasma protein binding of mCBS. Specifically, this study looked at the metabolism of mCBS in human, dog and rat liver microsomes and concluded that no metabolism of mCBS was detected. The study also looked at mCBS binding to human, rat and dog plasma proteins using ultrafiltration technique and concluded that there was about 20% binding to plasma proteins in all the species tested.

In Vitro Metabolism of β-O-Methyl Cellobioside Sulfate in Human, Dog and Rat Liver Microsomes In summary, this study was an in vitro investigaton designed to look at Phase I and Phase II metabolism of mCBS by rat, dog and human liver microsomes. The results indicate that no metabolism of mCBS was detected.

(i) Phase I Metabolism of β-O-methyl cellobioside sulfate in Human, Rat and Dog Liver Microsomes A stock concentration of 25 μM mCBS dissolved in 50% methanol in water was added to the reaction tubes (10 μL). The reaction mixture (final volume of 250 μL) comprised the following: 0.1 M phosphate buffer (pH 7.4), β-Nicotinamide adenine dinucleotide 2'-phosphate (NADPH) (1 mM), and pooled human, rat or dog liver microsomes (0.3 mg/ml). The reaction was started by adding NADPH after a 5 min pre-incubation period and incubated at 37° C. in a shaking water bath prior to stopping with 500 μL of ice cold acetonitrile. Samples were then vortex-mixed and centrifuged for 10 min at 14,000 rpm. Half of the samples (375 μl) were transferred to glass tubes and evaporated under a stream of nitrogen and at 37° C. Samples were then reconstituted in mobile phase A (250 μL). The final concentration of mCBS was 1 μM in the incubation medium.

The reaction mixtures were incubated for 1 hour with sampling in triplicate at 0, 15, 30, 45 and 60 min time points. A negative control (no NADPH) was used in parallel with the study samples. A positive control; midazolam, 25 μM (10 μL) was incubated in the same condition for 1 h. The final concentration of midazolam was 1 μM in the incubation medium

TABLE 5

Summary of microsome reaction incubation conditions

|  | Phase I Metabolic Stability | Phase II Metabolic Stability |
| --- | --- | --- |
| Substrate concentrations | 1 μM | 100 μM |
| Incubation volume | 250 μL | 250 μL |
| Incubation medium | Phosphate buffer 100 mM pH 7.4 | Phosphate buffer 100 mM pH 7.4 |
| Incubation total time | 1 h | 2 h |
| Liver microsome protein concentrations | 0.3 mg/ml | 0.3 mg/ml |
| Cofactor concentrations | 1 mM (NADPH) | 5 mM (UDPGA) |
| Stop reaction | 500 μL acetonitrile | 500 μL cold acetonitrile |

(ii) Bioanalysis: Calibration Curves for mCBS

A mix stock solutions of mCBS (30 μg/ml—as free base) and midazolam (10 μg/ml) in 50% methanol in water were diluted to 25, 20, 12.5, 6.25, 2.5, 1.25, 0.25 and 0.125 μg/ml for mCBS, and 8333, 6667, 4167, 2083, 833, 417, 83.3, 41.7 ng/ml using 50% methanol in water, and aliquots of the working standard solutions (10 μL) were added to plastic tubes. Next, aliquots (190 μL) of phosphate buffer (100 mM, pH 7.4) and microsome solutions in phosphate buffer (100 mM, pH 7.4) (50 μL) were added to the tubes, followed by 500 μL aliquots of acetonitrile. Tubes were vortex-mixed and centrifuged for 10 min at 14,000 rpm. Aliquots of supernatant (375 μL) were evaporated under a stream of nitrogen and reconstituted in mobile phase A (250 μL) and injected directly into the LC-MS/MS system (10 μL).

(iii) Phase II Metabolism of mCBS in Human, Rat and Dog Liver Microsomes

Stock concentrations of 1 mg/ml mCBS dissolved in methanol (50 μL) were evaporated to dryness in the reaction tube and resuspended in the reaction mixture at a final concentration of 100 μM. The mixtures (final volume of 250 μl) comprised the following: 0.1 M phosphate buffer (pH 7.4), MgCl$_2$ (1 mM), uridine 5'-diphosphoglucuronic acid (UDPGA) (5 mM), liver microsomes (0.3 mg/ml), and alamethicin (25 μg/mg protein). The reaction mixtures were started by adding UDPGA after a 5 min pre-incubation period and incubated at 37° C. in a shaking water bath prior to stopping with ice-cold acetonitrile (500 μL). Samples were then vortex-mixed and centrifuged for 5 min at 14,000 rpm.

The reaction mixtures were incubated for 2 hours in liver microsomes (n=3). A negative control (no UDPGA) and positive control (paracetamol 100 μM) were incubated together with the study samples.

(iv) Mass Spectrometry Conditions

The LC-MS/MS parameters used for the analysis of mCBS and midazolam are summarized in Table 6.

TABLE 6

HPLC and mass spectrometry conditions for analytes of interest.

HPLC

| | |
|---|---|
| Autosampler Temperature | 4° C. |
| Column | X-Terra MS C18 5 μm 2.1 × 150 mm |
| Mistral Temperature (Column oven) | 40° C. |
| Mobile phase A | 80% Ammonium acetate 10 mM, pH = 5/20% Acetonitrile/0.1% Hexylamine/ 0.1% Hexafluoro-2-propranolol |
| Mobile phase B | 80% acetonitrile in water |
| Wash solvent 1 (R2) | 0.2% formic acid in water |
| Wash solvent 2 (R0) | 20% acetonitrile in water |

| Gradient | Time (min) | Pump flow | Pump fraction B % |
|---|---|---|---|
| | 1:00 | 0.4 | 0 |
| | 2:00 | 0.4 | 50 |
| | 2:30 | 0.4 | 50 |
| | 2:36 | 0.4 | 0 |
| | 4:00 | 0.4 | 0 |

MS/MS

| Analyte | Q1 Mass | Q3 Mass | Dwell time | DP | CE | CXP |
|---|---|---|---|---|---|---|
| β-O-Methyl Cellobioside Sulfate (free-base) | 709.7 | 256.9 | 150 | −95.00 | −88.00 | −17.00 |
| Midazolam | 325.8 | 291.1 | 150 | 136.0 | 39.00 | 22.00 |

(v) Results

Figure 2:
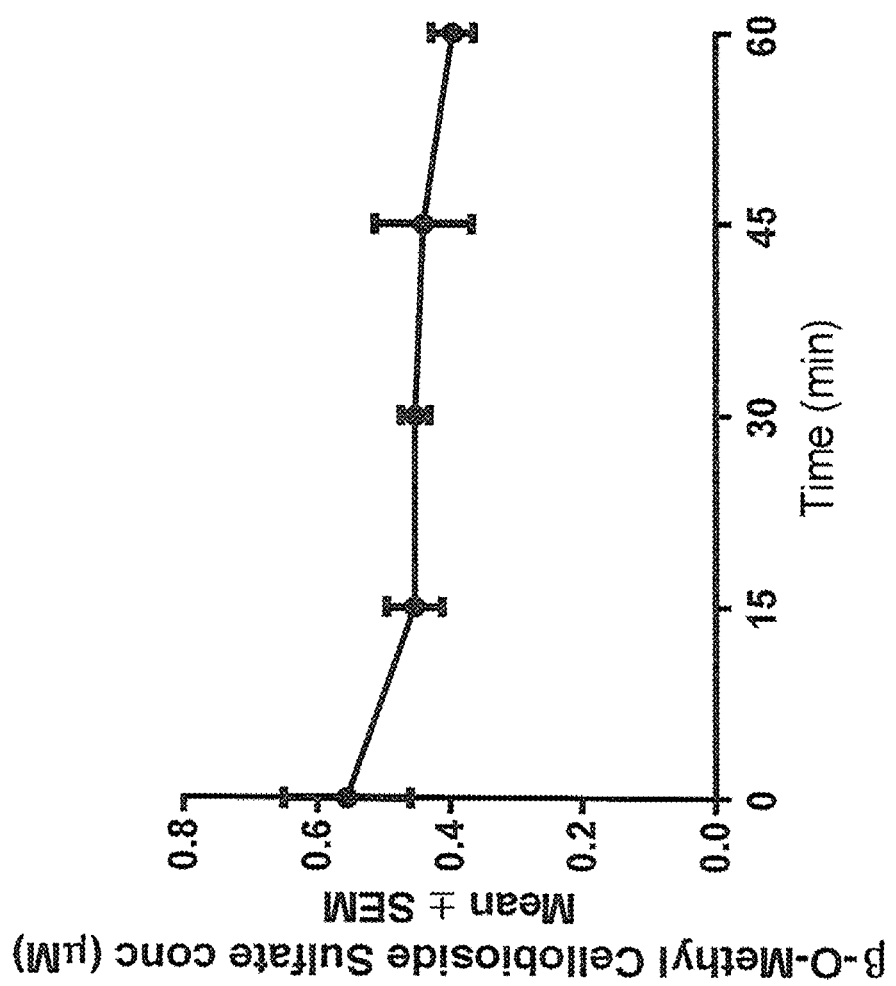
FIG. 2 is a graphical representation demonstrating metabolic stability of mCBS in human liver microsomes as shown by the measure (mean SEM) of the concentration (in μM) of mCBS in the presence of human liver microsomes under conditions permissive of phase I metabolism.
Figure 3:
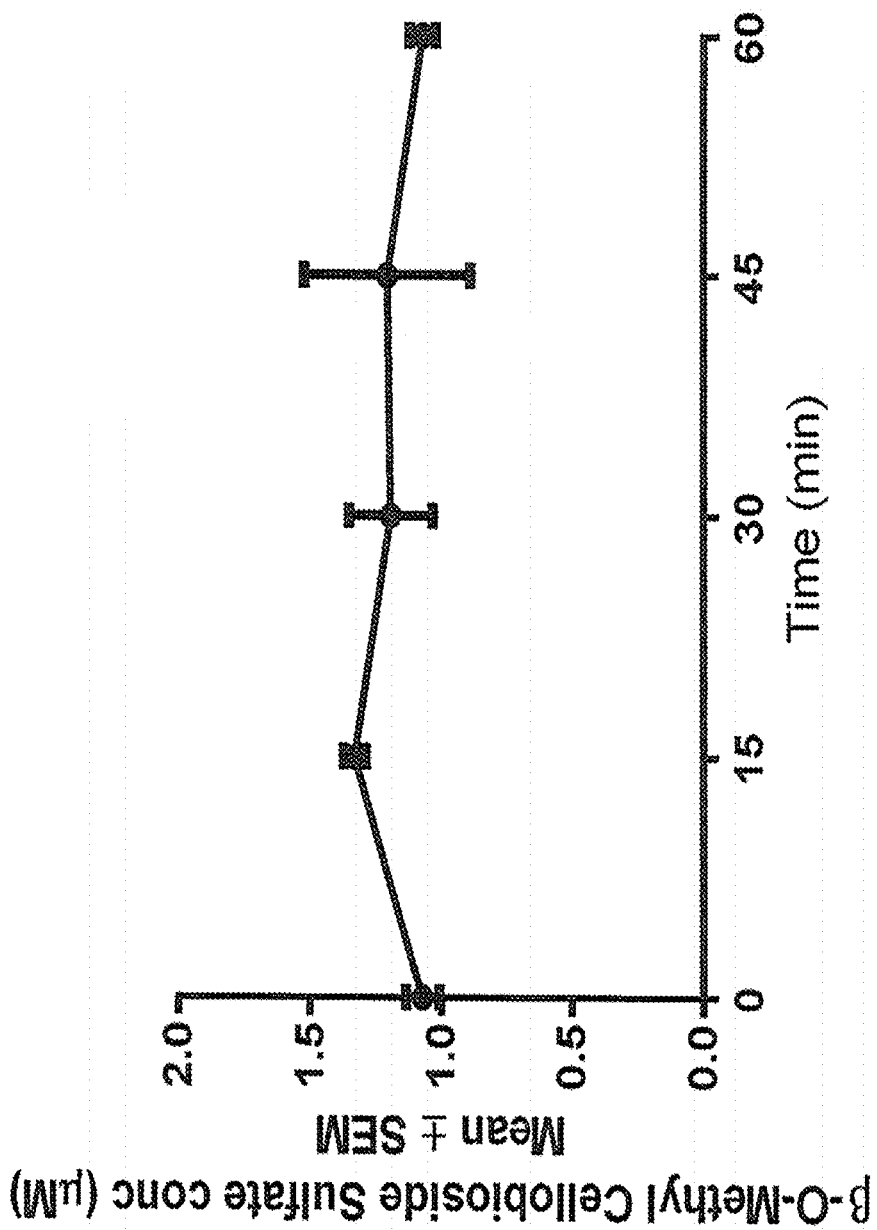
FIG. 3 is a graphical representation demonstrating metabolic stability of mCBS in human rat microsomes as shown by the measure (mean±SEM) of the concentration (in μM) of mCBS in the presence of rat liver microsomes under conditions permissive of phase I metabolism.
Figure 4:
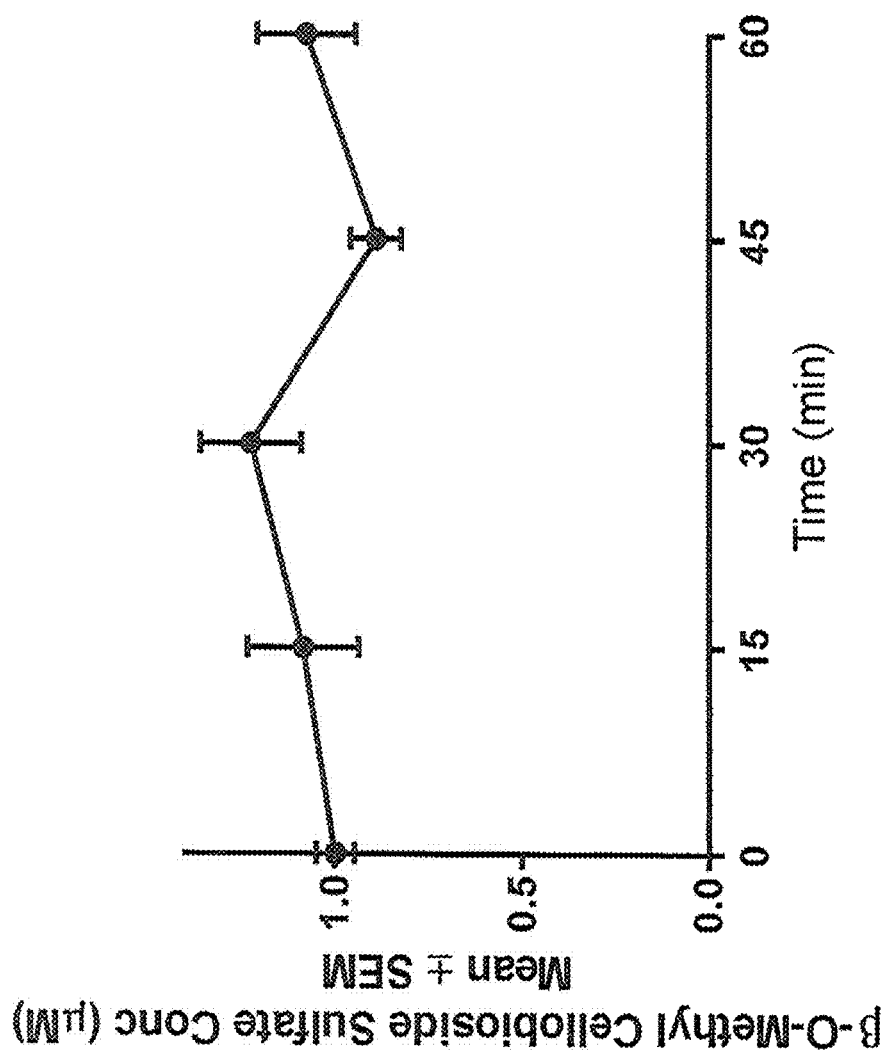
FIG. 4 is a graphical representation demonstrating metabolic stability of mCBS in dog liver microsomes as shown by the measure (mean±SEM) of the concentration (in μM) of mCBS in the presence of dog liver microsomes under conditions permissive of phase I metabolism.

The metabolic stability of mCBS in the presence of human, rat and dog liver microsomes in conditions permissive for phase I metabolism is shown in FIGS. 2-4. The results demonstrate that there was no significant metabolism of the test compound under these conditions. FIG. 2 is a graphical representation demonstrating metabolic stability of mCBS in human liver microsomes as shown by the measure (mean±SEM) of the concentration (in μM) of mCBS in the presence of human liver microsomes under conditions permissive of phase I metabolism. FIG. 3 is a graphical representation demonstrating metabolic stability of mCBS in human rat microsomes as shown by the measure (mean±SEM) of the concentration (in μM) of mCBS in the presence of rat liver microsomes under conditions permissive of phase I metabolism. FIG. 4 is a graphical representation demonstrating metabolic stability of mCBS in dog liver microsomes as shown by the measure (mean±SEM) of the concentration (in μM) of mCBS in the presence of dog liver microsomes under conditions permissive of phase I metabolism.

(vi) Phase II Metabolism

There were no ions matching the glucuronic acid metabolite of mCBS detected in reactions samples after incubation of the compound with human, rat and dog liver microsomes under conditions permissive for phase II metabolism. Paracetamol glucuronide formation in the incubation medium was confirmed by both Neutral loss and MRM scan.

In this in vitro study, the metabolism of mCBS was assessed by measuring the changes of the levels of free base form in the reaction medium.

Under conditions, permissive for phase I metabolism, there was no decrease in mCBS concentration after a 1 h incubation with liver microsomes from the three-species evaluated. Under the same conditions the positive control compound midazolam was almost completely metabolised in the presence of microsomes for three species.

It is noted the concentration of mCBS was less than 0.6 μM at time zero in the reaction with the human liver microsomes (whereas the concentration added was 1 μM). A similar observation was noted in the negative control samples containing liver microsome and no NADPH, but not in the negative control samples containing NADPH and no microsomes. Liver microsomes are complex tissues containing mixtures of proteins, phospholipids and fatty acids. The components of the liver microsomes tissues can affect the mass spectrometer ionisation and suppress the signal. As, the components of the liver microsomes vary among species, the ion suppression may be stronger in human microsomes and result in an apparent decrease in compound concentration which is independent of time and the presence of NADPH.

In summary, no/minimal phase I metabolism of the test item was detected in microsomal reactions with human, rat and dog microsomes. In the second in vitro metabolism study (phase II), glucuronide metabolite was also not detected after 2 hours incubation with liver microsomes from each species in the presence of uridine 5-diphosphoglucuronic acid (UDPGA).

Without being bound by any theory or specific mode of action, the applicants speculated that the lack of extensive in vitro metabolism mCBS may be explained by the presence of seven sulfate (SO3) groups which hinder the access of enzymes to the molecule. However, the results cannot exclude the possibility of in vivo desulfation followed by phase I or II metabolism.

Investigation of mCBS Binding to Human, Rat and Dog Plasma Proteins Using Ultrafiltration Technique In summary, this study was an in vitro study designed to look at binding of mCBS to rat, dog and human plasma proteins. The results obtained indicate that there was about 20% binding to plasma proteins in all the species tested.

In the study described here the existing method was modified to include the use of deuterated mCBS (mCBS-d3) as the internal standard. This bioanalytical method was used to assess the plasma protein binding of mCBS with rat, dog and human plasma.

Protein binding was assessed by an ultrafiltration method using Centrifree® Ultrafiltration Devices with a 30000 dalton molecular weight cut-off point. Briefly, known concentrations of mCBS (as free base) were added to human, rat and dog plasma samples and incubated for 20 min at 37° C. The samples were then subject to ultrafiltration to separate protein bound and unbound drug. The extent of protein binding was then defined as the percentage difference between the total and unbound concentration of the drug (with subtraction of non-specific binding to the ultrafiltration device in the presence of phosphate buffer only).

Reagents used are detailed in Table 7 below. The LC-MS/MS parameters used for the analysis of mCBS and mCBS-d3 are summarized in Table 8.

TABLE 7

Description of reagents used to investigate binding of mCBS to rat, dog and human plasma proteins.

| Item | Description |
|---|---|
| Sodium 0-methly cellobioside sulfate (mCBS•Na) | TQ # 1829, Expiry date: 16 Apr. 2016, Batch no: IG-01-327 (3), Purity: 96% |
| Internal standard: mCBS-d3 | TQ# 1886, Expiry date: 17 Nov. 2020, Lot no: AML-Sra- 016i, Purity: 90.1%, Isotope purity: 99.5% |
| mCBS stock solution (200 µg/mL) | Prepared by dissolving mCBS powder in 50% methanol in water, and further dilution in water to prepare a solution with 200 µg/mL concentration (with adjustment for the sodium content and % purity of the analyte). |
| mCBS-d3 stock solution (1 µg/mL) | Prepared by dissolving mCBS-d3 powder in 50% methanol in water, and further dilution in water to prepare a solution with 1 µg/mL concentration (with adjustment for the % purity of the analyte). |
| Human, rat and dog plasma | Pooled blank human, rat and dog plasma (Li-Hep as the anticoagulant), pH adjusted to 7.40 using $NaH_2PO_4$ |
| Phosphate Buffer | 2.50 mM; pH 7.40 |
| Centrifree ® Ultrafiltration Devices | Millipore Item no. 4104 - 30 000 NMWL |

(i) Analytical Method Parameters

TABLE 8

HPLC and mass spectrometry conditions for analytes of interest.

| Analyte | Q1 Mass | Q3 Mass | Dwell time | DP | CE | CXP |
|---|---|---|---|---|---|---|
| mCBS | 709.7 | 256.9 | 150 | −75.00 | −74.00 | −19.00 |
| mCBS-d3 | 711.2 | 258.5 | 150 | −75.00 | −74.00 | −16.00 |

| HPLC | |
|---|---|
| Autosampler Temperature | 4° C. |
| Column | X-Terra MS C18 5 µm 2.1 × 150 mm |
| Mistral Temperature (Column oven) | 40° C. |
| Mobile phase A | 80% Ammonium acetate 10 mM, pH = 5/20% Acetonitrile/0.1% Hexylamine/0.1% Hexafluoro-2-propranolol |
| Mobile phase B | 80% acetonitrile in water |
| Wash solvent (S1) | 20% acetonitrile in water |

| Parameter Table | mCBS | mCBS-d3 |
|---|---|---|
| CUR | 35.00 | 35.00 |
| CAD | Medium | Medium |
| IS | −2000 | −2000 |
| TEM | 450 | 450 |
| GS1 | 60.00 | 60.00 |
| GS2 | 60.00 | 60.00 |
| EP | −10.0 | −10.0 |
| Wash solvent 1 (S1) | 20% acetonitrile in water | |
| Wash solvent 2 (S2) | 50% acetonitrile in water | |
| Wash solvent 3 (S3) | 0.1% formic acid in 50% methanol | |

| Gradient | Time (min) | Pump flow | Pump fraction B % |
|---|---|---|---|
| | 1:00 | 0.45 | 0 |
| | 2:30 | 0.45 | 50 |
| | 2:50 | 0.45 | 50 |
| | 3:00 | 0.45 | 0 |
| | 4:30 | 0.45 | 0 |

MS/MS Parameters:
Q1 - first mass filler;
Q3 - mass analyser;
Dwell time - amount of time instrument spends at each transition;
DP: declustering potential;
EP: entrance potential;
CE: collision energy;
CXP: collision cell exit potential for product ions (ii) Sample Preparations mCBS stock solutions (10 µL) were spiked into solutions of each test matrix (490 µL) as listed below in Table 9 to have a final concentration of 200 ng/mL & 2000 ng/mL.

TABLE 9 mCBS spiked samples of each test matrix

| Matrix | mCBS concentration in the stock solutions spiked into the matrix (µg/mL) | mCBS final concentration (ng/mL) |
|---|---|---|
| Phosphate Buffer | 10 | 200 |
| Phosphate Buffer | 100 | 2000 |
| Plasma (human, rat, dog) | 10 | 200 |
| Plasma (human, rat, dog) | 100 | 2000 |

Spiked samples were then incubated at 37° C. for 20 minutes in a water bath. Aliquots of the samples from each test group (500 µL) were transferred to the ultrafiltration devices (n=3) and centrifuged for 20 minutes at 1000 g. After centrifugation, aliquots of the ultrafiltrates (50 µL) were transferred to separate test tubes for extraction, alongside duplicate aliquots of the samples prior to ultrafiltration from each test group.

(iii) Calibration Curve Preparation

An mCBS standard solution aliquots at 200 µg/mL were diluted as shown below.

| Standard ID/Conc. | Preparation Details |
|---|---|
| St A 200 µg/ml | |
| St B 100 µg/ml | mix 500 ul of A + 500 µL water |
| St C 75 µg/ml | mix 750 ul of B + 250 µL water |
| St D 50 µg/ml | mix 600 ul of C + 300 µL water |
| St E 25 µg/ml | mix 500 ul of D + 500 µL water |
| St F 10 µg/ml | mix 400 ul of E + 600 µL water |
| St G 5 µg/ml | mix 500 ul of F + 500 µL water |

Aliquots of the resulting standard solutions (10 µL) were then spiked into 490 µL of each of the relevant matrices (human, rat and dog plasma and phosphate buffer 2.5 mM, pH=7.4) and mixed well.

(iv) Extraction

Aliquots of the spiked standards and samples (50 µL) (after incubation and ultrafiltration) were mixed with 50 µL of internal standard solution 1 µg/mL. Pure acetonitrile (150 µL) was added and the samples vortexed immediately. The supernatant solutions were transferred to glass tubes and evaporated at 37° C. under a stream of air. Dried samples then were reconstituted in 150 µL of mobile phase A.

For quantification of samples before ultrafiltration, samples were analysed against a freshly prepared standard curve in plasma. The protein poor samples collected after ultrafiltration were quantified against the freshly prepared calibration curve in phosphate buffer 2.5 mM, pH=7.4. For estimation of non-specific binding, both before and after ultrafiltration samples were quantified against calibration curves in phosphate buffer.

(v) Results: Non-Specific Binding

Non-specific binding to the ultrafiltration devices was estimated at 0.5% and −1.97% at 200 and 2000 ng/mL respectively (Table 10 below). The binding of the compound to the ultrafiltration device was therefore considered to be negligible

TABLE 10

Non-specific Binding of mCBS to Ultrafiltration Device

Matrix: Phosphate Buffer pH 7.4
Concentrations of mCBS

| Replicate | 200 ng/mL Pre-filter | 200 ng/mL Post-filter | 2000 ng/mL Pre-filter | 2000 ng/mL Post-filter |
|---|---|---|---|---|
| 1 | 195 | 207 | 2090 | 1860 |
| 2 | 209 | 194 | 1970 | 2190 |
| 3 | | 202 | | 2160 |
| Mean | 202 | 201 | 2030 | 2070 |

Calculations: Non-specific binding $$\text{Non-specific binding } (NSB\ \%): 100 - \left[\frac{\text{Concentration post-filter}}{\text{Concentration pre-filter}} \times 100\right]$$

200 ng/mL  $\quad 100 - \left[\frac{201}{202} \times 100\right] \quad$ 0.50%

2000 ng/mL  $\quad 100 - \left[\frac{2070}{2030} \times 100\right] \quad$ −1.97%

(vi) Plasma Protein Binding

Plasma protein binding was calculated by comparison of concentration of mCBS spiked into human, rat and dog plasma, before and after filtration. The extent of binding was similar for all three species in the range of 16-23%. (see Tables 11-13 below). Plasma protein binding of mCBS was similar at both concentrations tested.

TABLE 11 mCBS binding to human plasma

Matrix: Human Plasma
Concentrations of mCBS

| Replicate | 200 ng/mL Pre-filter | 200 ng/mL Post-filter | 2000 ng/mL Pre-filter | 2000 ng/mL Post-filter |
|---|---|---|---|---|
| 1 | 213 | 169 | 2070 | 1770 |
| 2 | 217 | 181 | 2190 | 1860 |
| 3 | | 150 | | 1750 |
| Mean | 215 | 167 | 2130 | 1793 |

Calculations: Plasma protein binding $$\text{Plasma protein binding } (\%): 100 - \left[\frac{\text{Concentration post-filter}}{\text{Concentration pre-filter}} \times 100\right]$$

200 ng/mL  $\quad 100 - \left[\frac{167}{215} \times 100\right] \quad$ 22.5%

2000 ng/mL  $\quad 100 - \left[\frac{1793}{2130} \times 100\right] \quad$ 15.8%

TABLE 12 mCBS binding to rat plasma

Matrix: Rat Plasma
Concentrations of mCBS

| Replicate | 200 ng/mL Pre-filter | 200 ng/mL Post-filter | 2000 ng/mL Pre-filter | 2000 ng/mL Post-filter |
|---|---|---|---|---|
| 1 | 205 | 179 | 2090 | 1740 |
| 2 | 217 | 167 | 2180 | 1690 |
| 3 | | 164 | | 1710 |
| Mean | 211 | 170 | 2135 | 1713 |

Calculations: Plasma protein binding $$\text{Plasma protein binding } (\%): 100 - \left[\frac{\text{Concentration post-filter}}{\text{Concentration pre-filter}} \times 100\right]$$

200 ng/mL  $\quad 100 - \left[\frac{170}{211} \times 100\right] \quad$ 19.4%

2000 ng/mL  $\quad 100 - \left[\frac{1713}{2135} \times 100\right] \quad$ 19.8%

TABLE 13 mCBS binding to dog plasma

Matrix: Dog Plasma
Concentrations of mCBS

| Replicate | 200 ng/mL Pre-filter | 200 ng/mL Post-filter | 2000 ng/mL Pre-filter | 2000 ng/mL Post-filter |
|---|---|---|---|---|
| 1 | 225 | 186 | 2330 | 1900 |
| 2 | 230 | 194 | 2490 | 1970 |
| 3 | | 169 | | 1840 |
| Mean | | 183 | 2410 | 1903 |

Calculations: Plasma protein binding $$\text{Plasma protein binding } (\%): 100 - \left[\frac{\text{Concentration post-filter}}{\text{Concentration pre-filter}} \times 100\right]$$

200 ng/mL  $\quad 100 - \left[\frac{183}{228} \times 100\right] \quad$ 19.6%

2000 ng/mL  $\quad 100 - \left[\frac{1903}{2410} \times 100\right] \quad$ 21.0%

In this study mCBS binding to plasma proteins from human, rat and dog was at approximately 20%. The extent of binding was similar at 200 and 2000 ng/mL and non-specific binding to the ultrafiltration device was negligible.

Example 9: In Vivo Investigation of Dosages and Toxicity of mCBS Following Continuous IV Infusion Over Extended Period of Seven Consecutive Days in Rats This example outlines in vivo studies of dose ranges and toxicity investigation of mCBS when administered via IV infusion to Sprague-Dawley rats continuously (24 hours/day) over a period of seven consecutive days. This example demonstrates that, under this intensive administration regime of mCBS in rats, there were no observable adverse effect levels for mCBS at a dosage of 1394 mg/kg/day (free base; after correcting for potency and salt content) when given to the rat.

The objective of these studies was to determine the toxicity of the test item, mCBS, when administered by continuous (24 hours/day) intravenous infusion through a surgically implanted catheter for 7 consecutive days to Sprague-Dawley rats.

The test and control item dose formulations of mCBS (in the form of the heptasodium salt mCBS-Na) were administered to groups of rats by continuous (24 hours/day) intravenous infusion for 7 consecutive days as described in the Table 14 below.

pathological alteration. The microscopic findings in the kidneys correlated with increases in kidney weight.

In the spleen, accumulation of foamy macrophages associated with increased apoptotic cells in the red pulp was observed in animals treated with ≥1394 mg/kg/day mCBS (free base). These splenic changes were occasionally accompanied by stromal cell hyperplasia, increased cellularity/size of white pulp (germinal center), capsular fibrosis and

TABLE 14

Dosage formulations of mCBS (in the form of the heptasodium salt mCBS•Na) administered to Sprague-Dawley rats by continuous intravenous infusion through a surgically implanted catheter for 7 consecutive days.

| Group number | Group Designation | Dose Level (mg/kg/day)** | Dose Conc. (mg/mL)** | Corrected Dose Level (mg/kg/day)*** | Corrected Dose Conc. (mg/mL)*** | Infusion Rate (mL/kg/hr) | Infusion Duration (days) | Number of Animals Males | Females |
|---|---|---|---|---|---|---|---|---|---|
| 1 | Control* | 0 | 0 | 0 | 0 | 2.5 | 7 | 3 | 3 |
| 2 | Low dose | 1920 | 32 | 1394 | 23.2 | 2.5 | 7 | 3 | 3 |
| 3 | Mid dose | 3000 | 50 | 2178 | 36.3 | 2.5 | 7 | 3 | 3 |
| 4 | High dose | 4800 | 80 | 3484 | 58.1 | 2.5 | 7 | 3 | 3 |
| 5 | Control 2* | 0 | 0 | 0 | 0 | 4 | 7 | 3 | 3 |
| 6 | High dose 2 | 7680 | 80 | 5575 | 58.1 | 4 | 7 | 3 | 3 |

*The Control and Control 2 animals received 0.9% NaCl for Injection. USP only.
**Dose levels and concentrations not corrected for potency.
***Dose levels and concentrations are expressed in terms of mCBS (free base) after correcting for potency and salt content with a correction factor of 0.726.

Parameters monitored during this study included mortality, clinical observations, body weights and food consumption. In addition, hematology, coagulation and clinical chemistry parameters were evaluated on Day 9. Blood samples were collected from the animals at timepoints relative to the start of the infusion for analysis of test item concentration in plasma. At termination (Day 9), all animals were euthanized and subjected to a gross necropsy examination. Organ weights were measured on selected organs and a selected list of tissues, including gross lesions, were retained and prepared for microscopic evaluation.

The administration of mCBS-Na by continuous (24 hours/day) intravenous infusion through a surgically-implanted catheter for 7 consecutive days to Sprague-Dawley rats resulted in the death of one female at 5575 mg/kg/day of mCBS (free base) after correcting for potency and salt level.

The plasma concentration versus time data indicates that steady state concentrations of mCBS were maintained over the 5 h to 96 h (or 168 h) infusion interval. The mean (±SEM) values for AUC5-96 h and Css increased linearly with dose.

Decreases in body weight gain, correlating with a decrease in food consumption were noted in the animals of both sexes treated with mCBS (free base) at 5575 mg/kg/day. Increases in white blood cell lines were noted in the animals of both sexes at doses ≥3484 mg/kg/day, while decreases in red blood cell counts, hemoglobin, hematocrit, mean corpuscular volume and mean corpuscular hemoglobin concentration as well as increases in the reticulocytes were noted in the males at 5575 mg/kg/day. Increases in activated partial thromboplastin time were noted in the males at doses ≥2178 mg/kg/day and in the females at doses ≥3484 mg/kg/day. Liver enzymes, alanine aminotransferase and aspartate aminotransferase, as well as cholesterol and triglycerides were increased in males dosed at 5575 mg/kg/day. In addition, there was an increase in urea and decreases in total protein and albumin in the animals of both sexes at 5575 mg/kg/day.

In the kidneys, proximal tubular vacuolation/rarefaction was bilaterally observed in animals treated with ≥2178 mg/kg/day mCBS (free base). This finding (simple tubular vacuolation/rarefaction) was not associated with any other increased hematopoiesis. The microscopic findings in the spleen correlated with increases in splenic weight.

In the liver, accumulation of foamy Kupffer cells often associated with increased sinusoidal lining cells (at ≥1394 mg/kg/day), extramedullary hematopoiesis (at 5575 mg/kg/day) was noted in animals treated with ≥1394 mg/kg/day mCBS (free base). In addition, single cell necrosis was seen in animals treated with ≥2178 mg/kg/day mCBS (free base) and focal or multiple focal necrosis was noted in animals treated with 2178 and 5575 mg/kg/day. In the 5575 mg/kg/day group, hepatic changes were more pronounced and/or frequent in males compared with females, with both male animals adequately exposed to mCBS showing minimal to mild hepatic changes.

In various lymph nodes (bronchial, mandibular, mediastinal, mesenteric, pancreatic hepatic and/or auricular), accumulation of foam macrophages was observed in a number of animals treated with ≥1394 mg/kg/day mCBS (free base).

The findings of accumulation of foamy macrophages (in the spleen and lymph nodes), foamy Kupffer cells (in the liver) and proximal tubular vacuolation/rarefaction (in the kidneys) suggest that test-item, mCBS, and/or its degradation product(s) were most likely captured by the mononuclear phagocyte system (in the spleen, liver and lymph nodes) and taken up by the renal tubular epithelium. Therefore, without being bound by any specific theory or particular mode of action, the applicants reasoned that these findings most likely represent an adaptive change of the mononuclear phagocytic system and kidneys, as a result of the phagocytosis and clearance of the test item and/or its degradation product(s). Additionally, other findings in the spleen [increased apoptotic cells, stromal cell hyperplasia, increased cellularity/size of white pulp (germinal center), increased hematopoiesis, and capsular fibrosis] and liver (increased sinusoidal lining cells and extramedullary hematopoiesis) were also reasoned by the applicants to be an adaptive response to the activated phagocyte system.

However, the single cell necrosis of the liver noted at 2178, 3484 and 5575 mg/kg/day (free base) were considered to be potentially adverse. Additionally, focal or multiple focal necrosis of the liver noted at 2178 and 5575 mg/kg/day. Although focal necrosis was not seen in animals treated with 3484 mg/kg/day and may occur spontaneously, given the fact that this finding was observed in animals treated with mCBS only, the relationship to test item cannot be excluded.

Consequently, the No Observable Adverse Effect Level (NOAEL) for mCBS was determined to be 1394 mg/kg/day (free base) in this study due to the histopathological changes observed in the liver at ≥2178 mg/kg/day (free base).

Example 10: In Vivo Investigation of Dosages and Toxicity of mCBS Following Continuous IV Infusion Over Extended Period of Up to 14 Consecutive Days in Dogs This example outlines in vivo studies of dose ranges and toxicity investigation of mCBS when administered via continuous IV infusion to Beagle dogs over a period of 14 days. This example demonstrates that, under this intensive administration regime of mCBS in dogs, continuous intravenous infusion (24 hours/day for 48 hours) of mCBS at 2788 mg/kg/day for 14 days was well tolerated with no effects on mortality, clinical observations, body weights, food consumption, clinical pathology (hematology, coagulation, and clinical chemistry), organ weight, or macroscopic evaluations.

Continuous Infusion of mCBS in Dogs

In summary, this study examined dose ranges of mCBS in dogs via continuous infusion with the aim to select the max dose of mCBS to use in a 14 days continuous infusion dog study. Similarly, the dose selected was either the MTD or one that results in the mCBS (free base) plasma level of at least 300 ug/ml (i.e. ~3× of the target human plasma level).

This study was also conducted inter alia to determine the maximum tolerated dose (MTD) of the test item, mCBS, when administered by continuous (24 hours/day) intravenous infusion through a surgically-implanted catheter for 48 hours per dose level for up to 4 dose levels to Beagle dogs.

Phase 1: Dose Escalation mCBS dose formulations were administered to Beagle dogs by continuous (24 hours/day) intravenous infusion for 48 hours per dose level for up to 4 dose levels, as described in the Table 15 below.

TABLE 15

Dosage formulations of mCBS (in the form of the heptasodium salt mCBS•Na) administered to Beagle dogs by continuous intravenous infusion through a surgically implanted catheter.

| Group number | Group Designation | Study Days | Dose Level (mg/kg/day)* | Dose Conc. (mg/mL)* | Corrected Dose Level (mg/kg/day)** | Corrected Dose Conc. (mg/mL)** | Infusion Rate (mL/kg/hr) | Infusion Duration (hours) | Number of Animals Male | Number of Animals Female |
|---|---|---|---|---|---|---|---|---|---|---|
| 1 | Low dose | 1 to 3 | 480 | 20 | 348 | 14.5 | 1 | 48 | 1 | 1 |
|  | Mid dose | 3 to 5 | 960 | 40 | 697 | 29.0 | 1 | 48 |  |  |
|  | High dose | 5 to 7 | 1920 | 80 | 1394 | 58.1 | 1 | 48 |  |  |
|  | High dose 2 | 7 to 9 | 3340 | 80 | 2788 | 58.1 | 2 | 48 |  |  |

*Dose levels and concentrations not corrected for potency.
**Dose levels and concentrations are expressed in terms of mCBS (free base) after correcting for potency and salt content with a correction factor of 0.726.

Parameters monitored during this phase of the study included mortality, clinical observations, body weights, and food consumption. Serial blood samples were collected from each animal to confirm mCBS plasma levels at the following time points: 24 and 48 hours post start of infusion of each dose level. Blood samples were also collected from each animal for clinical pathology evaluations (hematology, coagulation, and clinical chemistry) on Day 1, prior to administration of the new dose level on Days 3, 5, and 7, and on Day 9.

No dose-limiting toxicity (adverse clinical sign) was noted following a stepwise administration up to the highest dose level, therefore, the maximum tolerated dose (MTD) was considered to be 2788 mg/kg/day of mCBS administered by continuous (24 hours/day) intravenous infusion for 48 hours. The dose was not further escalated because steady-state plasma concentration (Css) was higher than 300 pig/mL, which is 3 times higher than the target plasma concentration in humans.

Quantifiable levels of mCBS were detected in the plasma samples collected from all animals at each time points, which indicated that the animals were appropriately administered with mCBS. Steady-state plasma mean concentrations (Css) ranged from 53.8 to 358 µg/mL, while mCBS was cleared (Cl) at a rate of 222 to 450 mL/hour/kg.

Continuous Infusion of mCBS in Dogs

In summary, this study examined continuous infusion of mCBS in dogs using the maximum tolerated dose (MTD) that was identified in the STX-102 study above.

Following confirmation of the MTD (2788 mg/kg/day), the dogs were then transferred to Phase 2 of the study, and the dosing administration was resumed at the MTD for 6 additional days of continuous infusion as indicated in Table 16 below.

TABLE 16

Dosage formulation of mCBS (in the form of the heptasodium salt mCBS•Na) identified in the STX-102 study as being the maximum tolerated dose administered by continuous intravenous infusion to Beagle dogs used in STX 102 for 6 additional days.

| Group number | Dose Level (mg/kg)* | Dose Conc. (mg/mL)* | Corrected Dose Level (mg/kg)** | Corrected Dose Conc. (mg/mL)** | Infusion Rate (mL/kg/hr) | Infusion Duration | Number of Animals | |
|---|---|---|---|---|---|---|---|---|
| | | | | | | | Male | Female |
| 1 | 3840 | 80 | 2788 | 58.1 | 2 | 6 days (144 hours) | 1 | 1 |

*Dose levels and concentrations not corrected for potency.
**Dose levels and concentrations are expressed in terms of mCBS (free base) after correcting for potency and salt content with a correction factor of 0.726.

Parameters monitored during this phase of the study included mortality, clinical observations, body weights, food consumption, clinical pathology (hematology, coagulation, and clinical chemistry), and organ weight changes. Serial blood samples for toxicokinetic analysis were collected from each animal at the following time points: 24 and 48 hours post start of infusion, immediately before the end of the infusion, 15, 30 minutes and 1, 1.5, 2, 3, 4, 6, 24 hours post end of infusion.

Following completion of the additional 6 days of continuous infusion and collection of the last toxicokinetic blood samples, all animals were euthanized and subjected to a necropsy examination on Day 8. Histological examination was performed on the liver and kidneys of all animals.

Continuous intravenous infusion (24 hours/day for 48 hours) of mCBS at 2788 mg/kg/day for 6 days (144 hours) was well tolerated with no effects on mortality, clinical observations, body weights, food consumption, clinical pathology (hematology, coagulation, and clinical chemistry), organ weight, or macroscopic evaluations.

Microscopic findings included renal proximal tubular vacuolation/rarefaction of the kidneys and accumulation of foamy Kupffer cells of the liver, however, were considered as non-adverse or adaptive.

Toxicokinetic analysis showed that steady-state plasma concentrations ($C_{ss}$) ranged from 223 to 246 µg/mL, while $AUC_{0-144}$ ($AUC_{0-168}$) ranged from 43800 (44100) to 48300 (48800) hr*g/mL. After end of infusion, the mCBS plasma concentrations declined rapidly at an estimated $t_{1/2}$ value of approximately 1 hour for both animals. The mCBS was cleared (Cl) at a rate of 472 to 522 mL/hour/kg. The volume of distribution (Vz) ranged from 740 to 741 mL/kg, suggesting that mCBS is largely distributed among tissues. There were no noteworthy sex-related differences.

Examples 11 to 22: Comparison of Cellobiose Sulfate and mCBS

In the following studies, cellobiose sulfate (CBS) and mCBS are compared. mCBS is chemically much more stable than CBS and, consequently, represents a better drug candidate. The methodologies used in Examples 11 to 22 are set out below.

Method and Materials for the Following Examples (11-22)

Human subjects. All human-related research was approved by the ANU Health Human Research Ethics Committee. Healthy adult donors were used as a source of erythrocytes and platelets for in vitro studies.

Animals. All animal experiments were approved by the Australian National University Animal Experimentation Ethics Committee. Pathogen free male and female C57BL/6 mice (6-8 weeks of age), female BALB/c mice (5-6 weeks of age) and male Wistar rats (weighing between 250-350 g) were obtained from the Australian Phenomics Facility at the Australian National University.

Cell lines and cell culture conditions. Human microvascular endothelial cells-1 (HMEC-1), carrying the type O blood group and thus not reactive with anti-blood group antibodies in human sera, were supplied by ATCC and were cultured in MCDB 131 medium supplemented with 10% heat-inactivated foetal calf serum (FCS), 2 mM L-glutamine, 100 IU ml$^{-1}$ penicillin and 100 µg ml$^{-1}$ streptomycin. Human umbilical vein endothelial cells (HUVEC) were established from primary cultures as previously described (Jaffe, E. A. Biology of endothelial cells. (Martinus Nijhoff Publishers; Distributors for the United States and Canada, Kluwer Boston, 1984) and cultured in Medium 199 supplemented with 20% FCS, 2 mM L-glutamine, 100 IU ml$^{-1}$ penicillin, 100 µg ml$^{-1}$ streptomycin, 130 µg ml$^{-1}$ of heparin and 1.2 mg ml$^{-1}$ of endothelial cell growth supplement (Sigma-Aldrich). Chinese Hamster Ovary (CHO)—K1 cells and xylotransferase-1-deficient CHO-K1 cells (pgsA-745 cells) that are HS and GAG deficient, were supplied by ATCC and grown in RPMI-1640 medium supplemented with 5% FCS and antibiotics. All cell lines were incubated in 5% $CO_2$ and ambient $O_2$ at 37° C. and were repeatedly tested for mycoplasma using a MycoAlert Assay kit (Lonza).

Histone-mediated cytotoxicity assays. To determine the cytotoxicity of calf thymus histones (Sigma-Aldrich), various concentrations of histones (100-800 µg ml$^{-1}$) were added to suspensions of HMEC-1 or HUVEC (1×10$^6$ ml$^{-1}$) in 96 well plates and incubated for 1 h at 37° C. Cells were then incubated for 5 min at 37° C. with propidium iodide (PI; 2.5 µg ml$^{-1}$) (ThermoFisher Scientific), to detect dead cells, and Calcein-AM (0.04 µM) (ThermoFisher Scientific), to detect viable cells, placed on ice and the percentage of dead and viable cells determined by flow cytometry using the gating strategies depicted in Extended Data FIG. 1. In inhibition assays, HMEC-1 were incubated with histones (400 µg ml$^{-1}$) for 1 h at 37° C. in the presence of different concentrations of compounds (12.5-400 µg ml$^{-1}$) prior to the addition of PI and Calcein-AM. HMEC-1 cytotoxicity at each compound concentration was then determined based on the formula:

$$\text{Cytotoxicity (\%)} = \frac{\text{Dead (compound \& histones)} - \text{Dead (cells alone)} \times 100}{\text{Dead (histones alone)} - \text{Dead (cells alone)}}$$

and the IC50 value for each polyanion then determined based on the line of best fit. In some experiments confluent monolayers of HMEC-1 in 96 well plates were incubated in serum free MCDB 131 medium for 1 h with diluent alone (saline), histones alone (400 µg ml$^{-1}$) or histones in the presence of mCBS (100 µg ml$^{-1}$) and then viable and dead cells detected by Calcein-AM or PI uptake, respectively, using a Leica SP5 confocal microscope. Suspensions of HMEC-1 were also depleted of cell surface HS by digestion with either *Flavobacterium* heparinises (HPNSE) I, II and III (Sigma-Aldrich) or human platelet heparanase (HPSE) (Freeman, C. & Parish, C. R. Human platelet heparanase: purification, characterization and catalytic activity. *Biochem J* 330 (Pt 3), 1341-1350 (1998)) as reported elsewhere (Khanna, M., Ranasinghe, C., Jackson, R. & Parish, C. R. Heparan sulfate as a receptor for poxvirus infections and as a target for antiviral agents. *J Gen Virol*, doi:10.1099/jgv.0.000921 (2017)), and then examined for sensitivity to histone-mediated cytotoxicity as described above for HMEC-1. Similarly, suspensions of wild type CHO-K1 and HS/GAG deficient pgsA-745 CHO-K1 cells were compared for their sensitivity to histone-mediated cytotoxicity.

Lipid bilayer assays. Artificial lipid bilayers, prepared as previously described (Rebbeck, R. T. et al. The beta(1a) subunit of the skeletal DHPR binds to skeletal RyR1 and activates the channel via its 35-residue C-terminal tail. *Biophys J* 100, 922-930, doi:10.1016/j.bpj.2011.01.022 (2011), separated symmetrical 150 mM or 250 mM KCl (pH~5.5) solutions. Histones (1 µM, 15.2 µg ml$^{-1}$) were added to bilayers alone or after 0.5-3 h incubation with 10 µM CBS (3.5 µg ml$^{-1}$) or 10 µM MTS (5.1 µg ml$^{-1}$) at ~20° C. Current was recorded continuously after histone addition until the bilayers broke or the experiment was terminated.

Calcium flux studies in endothelial cells. HMEC-1 ($2\times10^7$ ml$^{-1}$) in RPMI-1640 medium were incubated with Indo-1 AM (5 µM) (ThermoFisher) at 37° C. for 60 min. (Tellam, R. L. & Parish, C. R. The effect of sulfated polysaccharides on the free intracellular calcium ion concentration of lymphocytes. *Biochim Biophys Acta* 930, 55-64 (1987) & Weston, S. A., Tellam, R. L. & Parish, C. R. Dextran sulfate induces changes in the free intracellular calcium ion concentration of a subpopulation of immature thymocytes. *Immunol Cell Biol* 69 (Pt 6), 369-376, doi:10.1038/icb.1991.53 (1991).) After 3 washes with RPMI-1640 medium supplemented with 5% FCS the cells were resuspended at $4\times10^6$ ml$^{-1}$ in ice-chilled HEPES-buffered saline (NaCl 8 g l$^{-1}$, KCl 0.4 g l$^{-1}$, CaCl$_2$ 0.2 g l$^{-1}$, MgCl$_2$·6H$_2$O 0.2 g l$^{-1}$, D-glucose 1.8 g l$^{-1}$, pH 7.4) supplemented with 10 mM HEPES. The cell suspension was kept on ice and used within 3 h. Intracellular Ca$^{2+}$ flux was monitored using flow cytometry. The cells were pre-equilibrated and maintained at 37° C. during analysis using an external sheath connected to a heated water bath. After the exclusion of cellular debris and clumped cells (on the basis of FSC/SSC light scattering) the basal Ca$^{2+}$ level was monitored for 2 min before histone addition in the presence/absence of novel compounds. Ca$^{2+}$ levels were measured at 1, 4 and 10 min post-histone addition with a constant flow rate (~300 events/sec). Ca$^{2+}$ flux was determined as an increase in the ratio of geometric mean fluorescence intensity (GMFI) of Ca$^{2+}$-bound over Ca$^{2+}$-unbound Indo-1.

In vitro erythrocyte microscopy, aggregation, fragility and deformability assays. Histone-mediated aggregation of human erythrocytes and its inhibition by various compounds was detected by flow cytometry, based on either forward and side scatter parameters or erythrocyte auto-fluorescence, as reported by some of the inventors previously (see Kordbacheh, F., O'Meara, C. H., Coupland, L. A., Lelliott, P. M. & Parish, C. R. Extracellular histones induce erythrocyte fragility and anemia. *Blood* 130, 2884-2888, doi:10.1182/blood-2017-06-790519 (2017)) and scanning electron microscopy as described earlier (Yabas, M. et al. Mice deficient in the putative phospholipid flippase ATP11C exhibit altered erythrocyte shape, anemia, and reduced erythrocyte life span. *J Biol Chem* 289, 19531-19537, doi: 10.1074/jbc.C114.570267 (2014)). Similarly, erythrocyte fragility induced by histones, in the presence or absence of inhibitors, was quantified using a sheer stress assay as reported by some of the inventors previously (see Kordbacheh, F., O'Meara, C. H., Coupland, L. A., Lelliott, P. M. & Parish, C. R. Extracellular histones induce erythrocyte fragility and anemia. *Blood* 130, 2884-2888, doi:10.1182/blood-2017-06-790519 (2017)). Finally, the reduced deformability of erythrocytes in the presence of histones and the effect of inhibitors on this process was assessed by measuring the passage of erythrocytes through an artificial human spleen (see Deplaine, G. et al. The sensing of poorly deformable red blood cells by the human spleen can be mimicked in vitro. *Blood* 117, e88-95, doi:10.1182/blood-2010-10-312801 (2011).

In vitro platelet aggregation and degranulation assays. For aggregation studies platelets were isolated from human whole blood collected into Na-citrate vacutainers through 2-step centrifugation at room temperature (200×g for 20 min then the platelet-rich plasma 800×g for 15 min), the platelet pellet resuspended in Hank's balanced salt solution containing calcium and magnesium and histones added and incubated in the presence/absence of compounds at the concentrations of each as indicated. Samples were assessed for degree of platelet aggregation after 15 min exposure to histones by flow cytometry using the characteristic log FSC vs log SSC identification of platelets, with increases in the geometric mean of log FSC indicative of platelet aggregation.

For the platelet activation assay, whole blood collected in Na-citrate vacutainers was monitored for platelet degranulation using the luminescence mode on the Chrono-Log Model 700 with Chrono-Lume reagent (Chrono-Log Corp). Saline (300 µl) was added to pre-warmed blood (420 µl) with a stirrer bar in-situ. Chromo-Lume reagent (100 µl) was then added and incubated for 2 min before histones±compounds diluted in water were added in a total volume of 180 µl at the concentrations indicated. Results expressed as ATP release calculated as a percentage of the histone+saline control.

In-vivo histone toxicity assays. BALB/c female mice (5~6 weeks of age), that are more prone to histone-induced anemia and easier to inject i.v. at this young age than C57BL/6 mice, were injected i.p. with test compounds at concentrations indicated 10 min prior to i.v. injection of histones (50 mg kg$^{-1}$) in phosphate buffered saline. Retro-orbital bleeds were performed at 10 min after histone injection and collected blood added to acid citrate dextrose (ACD), the 10 min blood sample being subjected to hematologic analyses for platelet and erythrocyte content using an ADVIA 2120i Hematology Analyzer. Spleens were also harvested at 10 min post-histone injection and splenic hemoglobin content quantified using a hemoglobin assay kit (Sigma-Aldrich). In the case of 4 h blood samples, male C57/BL/6 mice (6-8 weeks of age) were injected with test compounds and histones as above and plasma isolated and stored frozen for subsequent biochemical testing, with markers for liver (alanine aminotransferase, ALT), kidney (Creatinine, Crea) and general tissue (lactate dehydrogenase, LDH) damage being determined by the Department of Pathology, The Canberra Hospital.

Murine deep vein thrombosis (DVT) model. The procedure used is largely as previously described (see Brill, A. et al. Neutrophil extracellular traps promote deep vein thrombosis in mice. *J Thromb Haemost* 10, 136-144, doi:10.1111/j.1538-7836.2011.04544.x (2012)). Briefly, 8 week old male C57BL/6 mice were anaesthetised, a laparotomy incision made, the intestines exteriorised and then, after gentle separation from the abdominal aorta, the inferior vena cava (IVC) immediately below the renal veins was ligated to ~10% patency and all associated IVC tributaries were ligated. The peritoneum and skin were closed following which all mice received an i.v. injection of histones via the tail vein (10 mg kg$^{-1}$) or an equivalent volume of saline followed 5 min later by an i.v. injection of test compounds (50 mg kg$^{-1}$) or saline. Mice were monitored for 48 h after which they were re-anesthetised, re-opened and any thrombi that had developed distal to the IVC stenosis were removed for analysis. Sham operated control animals received laparotomy and 90% ligation of the IVC, however the ligation was removed immediately after occlusion of the IVC.

Rat caecal ligation and puncture (CLP) assay for sepsis. The CLP assay was performed in male Wistar rats as previously described (see Hubbard, W. J. et al. Cecal ligation and puncture. *Shock* 24 Suppl 1, 52-57 (2005). Test compounds (50 mg kg$^{-1}$) dissolved in saline or an equivalent volume of saline only (Control cohort) were administered i.p. 5 min pre-CLP and 5, 10 and 15 h post-op until cessation of the experiment at 20 h. Sham-CLP rats underwent the same procedure, however, the caecum was not ligated or punctured and these rats received saline at the same times as above. At the conclusion of the experimental time period (20 h) or when morbidity required ethical euthanasia, the rats were anaesthetised and blood was collected via cardiac puncture into EDTA for subsequent analysis of liver (ALT) and kidney (creatinine) function by the Department of Pathology, The Canberra Hospital. The propensity for clots to form within the blood samples of the saline treated control CLP animals (despite the presence of EDTA) prevented successful analysis of plasma samples from all animals.

Rat cardiac IRI model. The method used is based on a combination of previously published procedures (see Takada, Y., Hashimoto, M., Kasahara, J., Aihara, K. & Fukunaga, K. Cytoprotective effect of sodium orthovanadate on ischemia/reperfusion-induced injury in the rat heart involves Akt activation and inhibition of fodrin breakdown and apoptosis. *J Pharmacol Exp Ther* 311, 1249-1255, doi:10.1124/jpet.104.070839 (2004) & Hale, S. L., Dae, M. W. & Kloner, R. A. Hypothermia during reperfusion limits 'no-reflow' injury in a rabbit model of acute myocardial infarction. *Cardiovasc Res* 59, 715-722 (2003)). Male Wistar rats were anaesthetised with isofluorane, intubated via tracheostomy and ventilated with a tidal volume of 1 ml 150 g$^{-1}$ and a respiratory rate of 65 breaths min$^{-1}$. Supplemental oxygen was delivered at a FiO$_2$ of ~30%. A left hemithoracotomy was performed to enable visualisation of the left ventricle. The left coronary arterial plexus (LCA) was occluded using an atraumatic snare for 30 min prior to reperfusion for 30 min. Ischemia was confirmed by myocardial hyperaemia. The test compounds (30 mg kg$^{-1}$) or an equivalent volume (200 µl) of saline were injected into the lumen of the left ventricle (confirmed with aspiration) 5 min prior to the release of the snare for the reperfusion phase.

At the conclusion of reperfusion (30 min), Thioflavin S (1 ml 200 g$^{-1}$ of body weight) was slowly injected into the lumen of the left ventricle, to define the territory of microvascular obstruction (MVO) within the ischemic zone (IZ). The IZ territory was determined by the re-occlusion of the atraumatic snare and infusion of blue microspheres into the left ventricle (Unisperse Blue, BASF), distributed within solutions via ultrasonication using a CD-6800 (Unisonics) sonicator. The heart was then excised from the thorax, rinsed in isotonic saline and 2 mm sections were cut distal to the atraumatic snare at right angles to the interventricular line. This method produced 4 myocardial sections that were weighed and photographed (Sony Handycam, Zeiss 60× optical zoom) under ultraviolet light (territory of MVO) and bright light (IZ territory), before being incubated in tetrazolium chloride (TTC) to determine the region of necrotic myocardium. Planimetry (Image J, Freeware) was used to quantify the areas of the IZ, MVO and necrosis.

Rat ischemia reperfusion tissue flap model. The procedure employed is largely based on a previously described method (Askar, I., Oktay, M. F., Gurlek, A. & Bac, B. Protective effects of some antineoplastic agents on ischemia-reperfusion injury in epigastric island skin flaps. *Microsurgery* 26, 193-199, doi:10.1002/micr.20193 (2006)). Briefly, male Wistar rats were anaesthetised, locally depilated and a 3 cm by 6 cm fasciocutaneous flap was excised leaving the vascular pedicle intact. The inferior epigastric artery was clamped, a fine rubber sheet was placed under the flap preventing oxygen diffusion from the tissues below and the flap was re-sutured back into place. The clamp was removed 10 h post-application permitting returned blood flow to the flap. Test compounds (50 mg kg$^{-1}$) or saline were administered i.p. 5 min prior to clamp application and 5 min following its removal. The rats were monitored for a total experimental period of 72 h during which rats received additional compound or saline i.p. at 24 and 48 h post-op. The 'Control No Clamp' rats had the tissue flap excised and rubber placed underneath prior to re-suturing, however, the vessel was not clamped and they received saline at the same time points as the other rats. At the end of the experimental period the viability of the flaps was determined by the percentage of black necrotic or reddened areas vs pink viable areas. Despite the application of Elizabethan collars and the use of analgesia as a settling agent, a small number of rats had to be prematurely euthanised when they repeatedly auto-cannibalised their flaps.

EAE Model of Multiple Sclerosis. EAE was induced in 8-12 week old C57Bl/6 mice by subcutaneous immunisation with 115 g/mouse myelin oligodendrocyte glycoprotein (MOG35-55 genscript) in Complete Freund's Adjuvant (Sigma) on day 1. 300 ng/mouse Pertussis toxin (List Biological Laboratories) in PBS was injected intra peritoneal (i.p.) on days 0 and 2. 50 mg/kg mCBS in PBS or PBS alone (vehicle) was given i.p. daily for day 0-9. Mice were monitored daily for signs of disease and were scored on a scale of 0-5 based on physical manifestations of disease. Mice were scored as follows: 0, clinically normal; 1, flaccid tail and/or ataxia; 2, hind limb weakness; 3, hind limb paralysis; 4, hind and front limb paralysis; and 5, moribund.

Statistical analysis. Prism software (Graphpad Software) was used to perform statistical tests and to generate graphs, with details of the test used included in Figure legends.

In-Vitro Evidence of the Biological Effects of mCBS

The following Examples 11 to 14 provide in vitro evidence of the biological effect of mCBS in neutralising free extracellular histones.

Example 11: mCBS Protects Endothelial Cells from Histone Toxicity

This example demonstrates that mCBS protects human endothelial cells from histone damage, and that this protective effect of mCBS against histone-induced damage to endothelial cells is concentration dependent. This example also demonstrates that mCBS can reverse damage in a proportion of endothelial cells exposed to histones.

Endothelial cells line the lumen of blood vessels and are essential for the integrity of the vascular system, providing many signals between the underlying tissues to passing blood cells and acting as an anticoagulant surface against which blood flows. Histones damage the cell membranes of endothelial cells inducing their death, thus the integrity of the microvasculature and the anticoagulant properties of the endothelium are lost. This results in widespread clot formation, a compromised delivery of oxygen and nutrient-containing fluid to vital organs and their subsequent damage and failure.

To assess whether mCBS protects human microvascular endothelial cells (HMECs) from histone damage, the health-status of endothelial cells was determined in vitro using 2 fluorescent dyes, calcein-AM and propidium iodide (PI). Healthy viable cells took-up calcein-AM and excluded PI whereas the reverse was true for damaged or dead cells. The uptake/exclusion of these dyes was measured using flow cytometry and visualised using confocal microscopy, as shown in FIG. 5.

Figure 5:
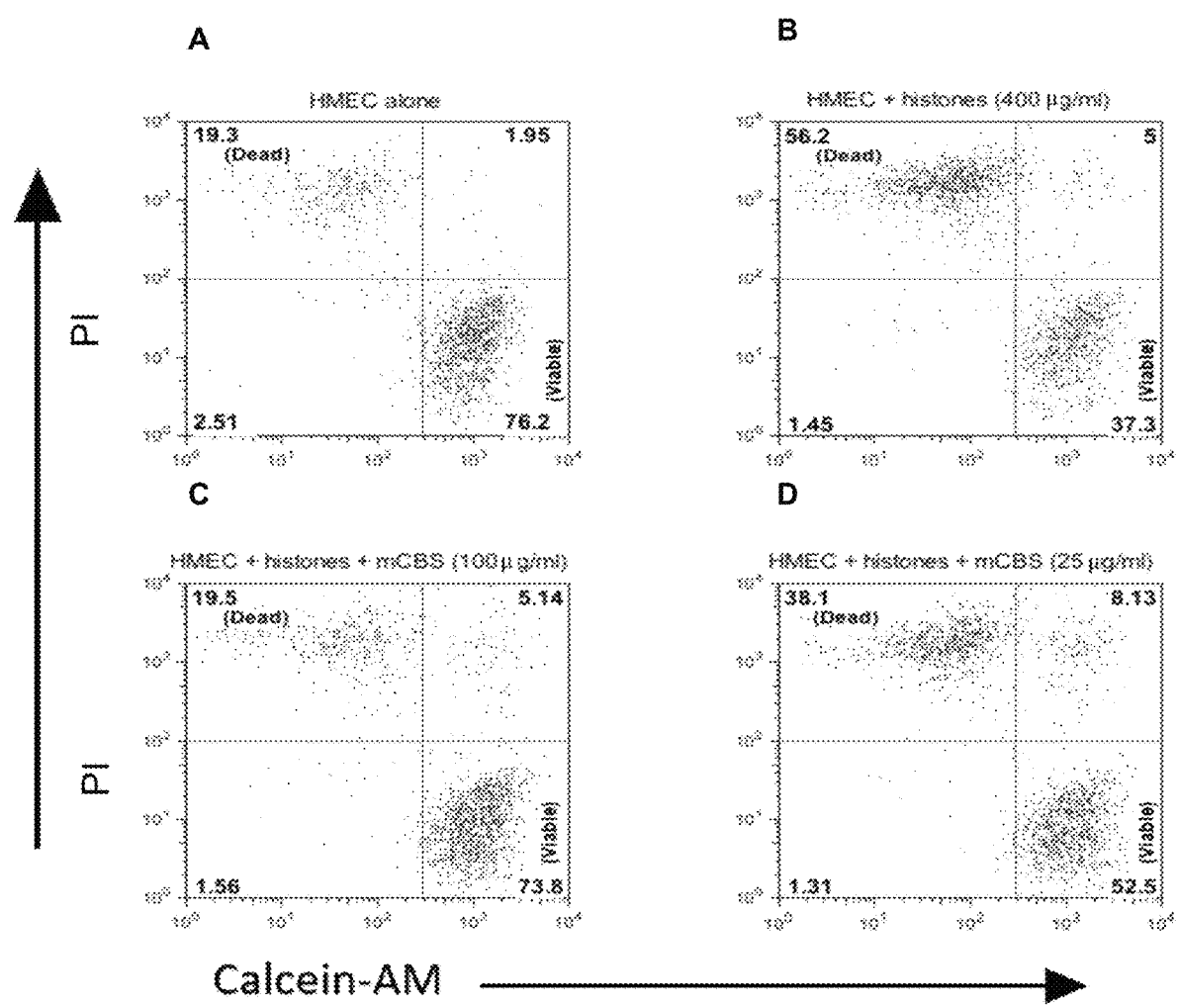
FIG. 5 A-D provide a graphical representation of flow cytometry output and panels E-G provide a pictorial representation of confocal microscopy results demonstrating that mCBS protects human microvascular endothelial cells (HMECs) from histone damage. Cultured HMECs were treated for 60 min with (A & E) water volume equivalent, (B & F) histones 400 μg/mL, (C & G) mCBS 100 μg/mL+ histones 400 μg/mL or (D) mCBS 25 μg/mL+histones 400 μg/mL, then labelled with the dyes calcein-AM and PI and analysed for extent of dye uptake using flow cytometry (A, B, C & D) or confocal microscopy (E, F & G). Numbers in quadrants indicate the percentage of cells present in each quadrant. Viable cells take-up calcein-AM (green) and exclude PI whereas damaged and dead cells take-up PI (red) and are unable to retain calcein-AM. The flow cytometry based assay used suspensions of HMEC (panels A-D), whereas the confocal microscopy experiment used HMEC monolayers (panels E-G), with monolayers of HMEC being more sensitive to histone damage.

With reference to FIG. 5, cultured HMECs were treated for 60 min with water volume equivalent (panels A and E in FIG. 5), histones 400 µg/mL (panels B and F in FIG. 5), mCBS 100 µg/mL and histones 400 µg/mL (panels C and G in FIG. 5) or mCBS 25 µg/mL and histones 400 µg/mL (panel D in FIG. 5), then labelled with the dyes calcein-AM and PI and analysed for extent of dye uptake using flow cytometry (panels A, B, C & D) or confocal microscopy (panels E, F & G). As shown in FIG. 5, cultured, untreated human microvascular endothelial cells (HMECs) were pre-dominantly viable with 76% containing calcein-AM and 19% PI (FIG. 5A). When exposed to histones (400 µg/mL), however, 37% remained viable whereas 56% took up PI (FIG. 5B). When mCBS (100 µg/mL) was added to the HMECs prior to exposure to histones 74% remain viable and 20% are dead based on PI uptake, hence mCBS is able to protect the HMECs from histone-mediated injury (FIG. 5C) This protective effect is concentration dependent with a lower amount of mCBS (25 µg/mL) providing a reduced level of protection (FIG. 5D). The effects of histones and mCBS on HMECs can also be seen using confocal microscopy where healthy untreated (FIG. 5E), and mCBS treated endothelial cells exposed to histones accumulate the green florescent calcein-AM dye (FIG. 5G), whereas untreated histone exposed endothelial cells take up the red fluorescent dye PI (FIG. 5F).

Figure 6:
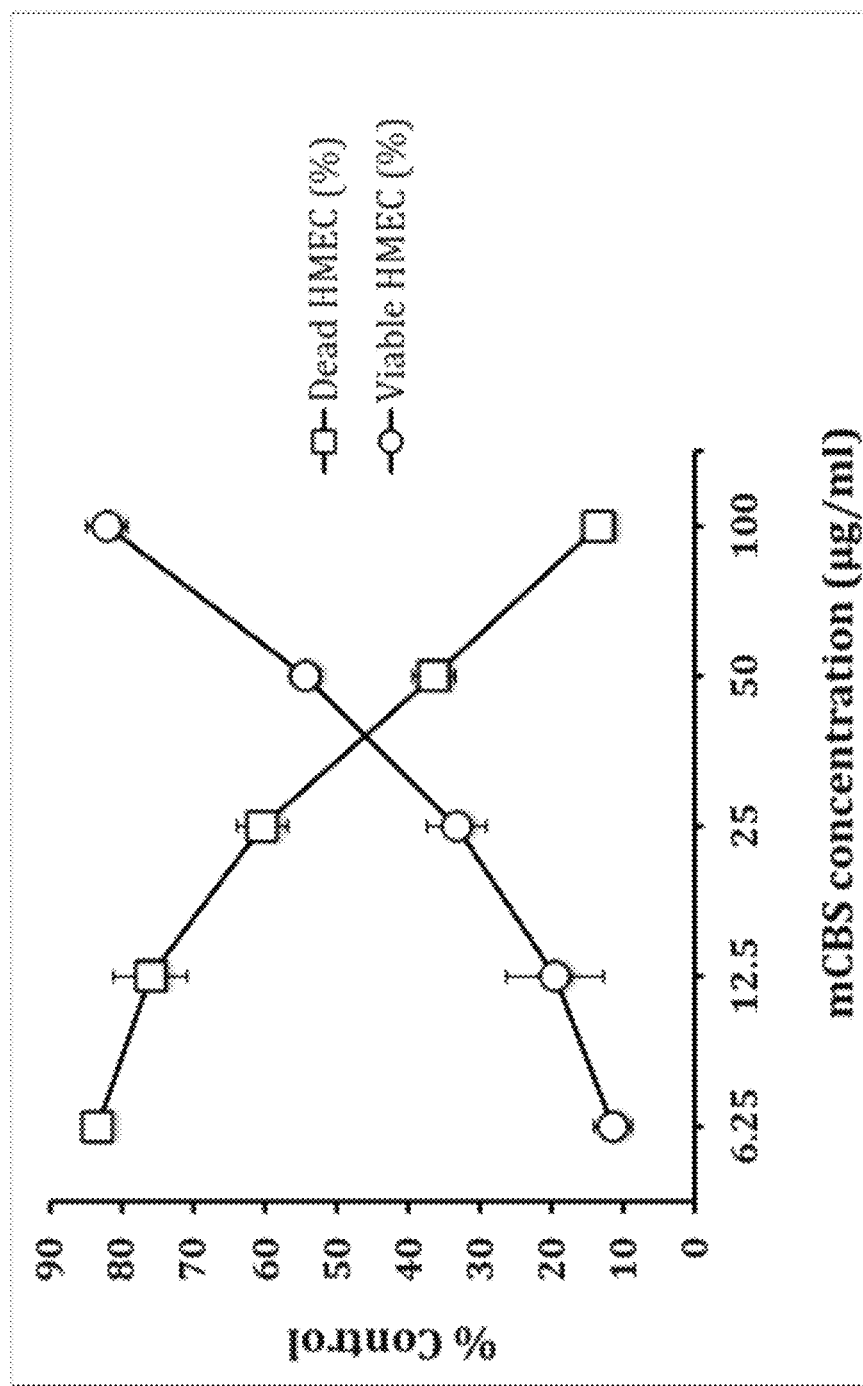
FIG. 6 is a graphical representation demonstrating that the protective effect of mCBS against histone-induced damage to HMECs is concentration dependent. Cultured HMECs were exposed to 400 μg/mL of histones following the addition of increasing concentrations of mCBS then analysed for the uptake of calcein-AM (viable) or PI (dead) using flow cytometry. Dead/viable cells expressed as % of control untreated cells. Error bars represent SEM.

Cultured HMECs were exposed to 400 µg/mL of histones following the addition of increasing concentrations of mCBS then analysed for the uptake of calcein-AM (viable) or PI (dead) using flow cytometry. The dose-dependent protective effect of mCBS against the damaging effects of histones for HMECs are shown in FIG. 6 which demonstrates that an increase in mCBS concentration resulted in an increase in viable cells (Calcein-AM uptake) and a reduction in dead cells (PI uptake). Accordingly, these results demonstrate that the protective effect of mCBS against histone-induced damage to HMECs is concentration dependent.

Figure 7:
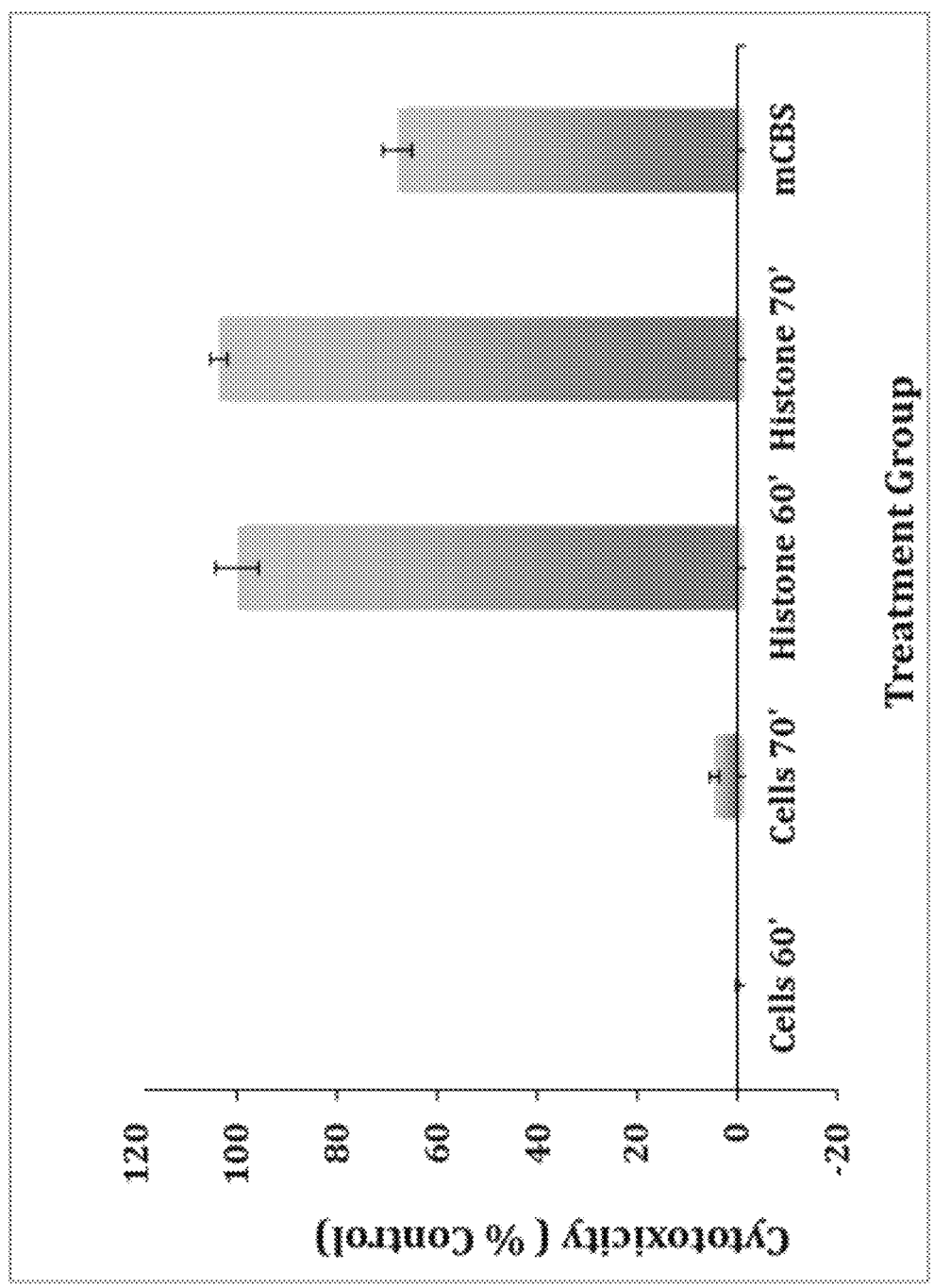
FIG. 7 is a graphical representation demonstrating that mCBS can reverse damage in a proportion of HMECs exposed to histones for 1 hour. Cultured HMECs were exposed to 400 μg/ml of histones for 60 min, treated with mCBS (100 μg/ml) for 10 min and then analysed for PI uptake using flow cytometry. Cytotoxicity expressed as a percentage of PI uptake by cells treated with histones for 60 min (+ve control). Error bars represent SEM.

To assess whether mCBS is able to reverse damage in endothelial cells following exposure to histones, cultured HMECs were exposed to 400 µg/ml of histones for 60 min, then treated with mCBS (100 µg/ml) for 10 min, and then Calcein-AM and PI was added for the last 5 min. The cells were then analysed for PI uptake using flow cytometry, with the results shown in FIG. 7. The results show that importantly, particularly in the clinical context, mCBS was also able to reverse the damaging effects of histones in a sub-population of HMECs. In this situation (where histones were added to cultured HMECs then 60 min later mCBS was added for 10 min, Calcein-AM and PI for the last 5 min), approximately 30% of HMECs reverted from PI uptake to PI exclusion and calcein-AM uptake following treatment with mCBS.

Example 12: mCBS and CBS Prevent, Reduce and Even Reverse Histone Induced Red Blood Cell Aggregation and Lysis This example demonstrates that mCBS prevents histone-induced RBC aggregation, and inhibits histone-induced RBC aggregation in a dose dependent manner. Furthermore, this example demonstrates that mCBS inhibits histone-induced RBC fragility, an effect that is exacerbated by higher shear flow rate and duration of shear exposure. Beyond this, this example demonstrates that mCBS is able to almost completely reverse histone-induced RBC susceptibility to lysis and aggregation.

Red blood cells (RBCs) are responsible for the transport of oxygen to tissues and contribute to clot formation by providing membrane proteins that act as scaffolding for thrombus formation. Their discoid shape and flexible structure permits RBCs to squeeze through narrow capillaries and resist sheer forces experienced within the rapidly flowing bloodstream. As they lack a nucleus, RBCs are unable to respond to damage through repair or apoptosis and instead are cleared by macrophages within the spleen when they become deformed. Damaged RBCs may, however, lose their discoid shape and hence flexibility prior to reaching the spleen thus rendering them susceptible to intravascular lysis due to sheer force exposure. In diseases where histone levels become elevated, such as sepsis, anaemia is frequently observed.

Figure 8:
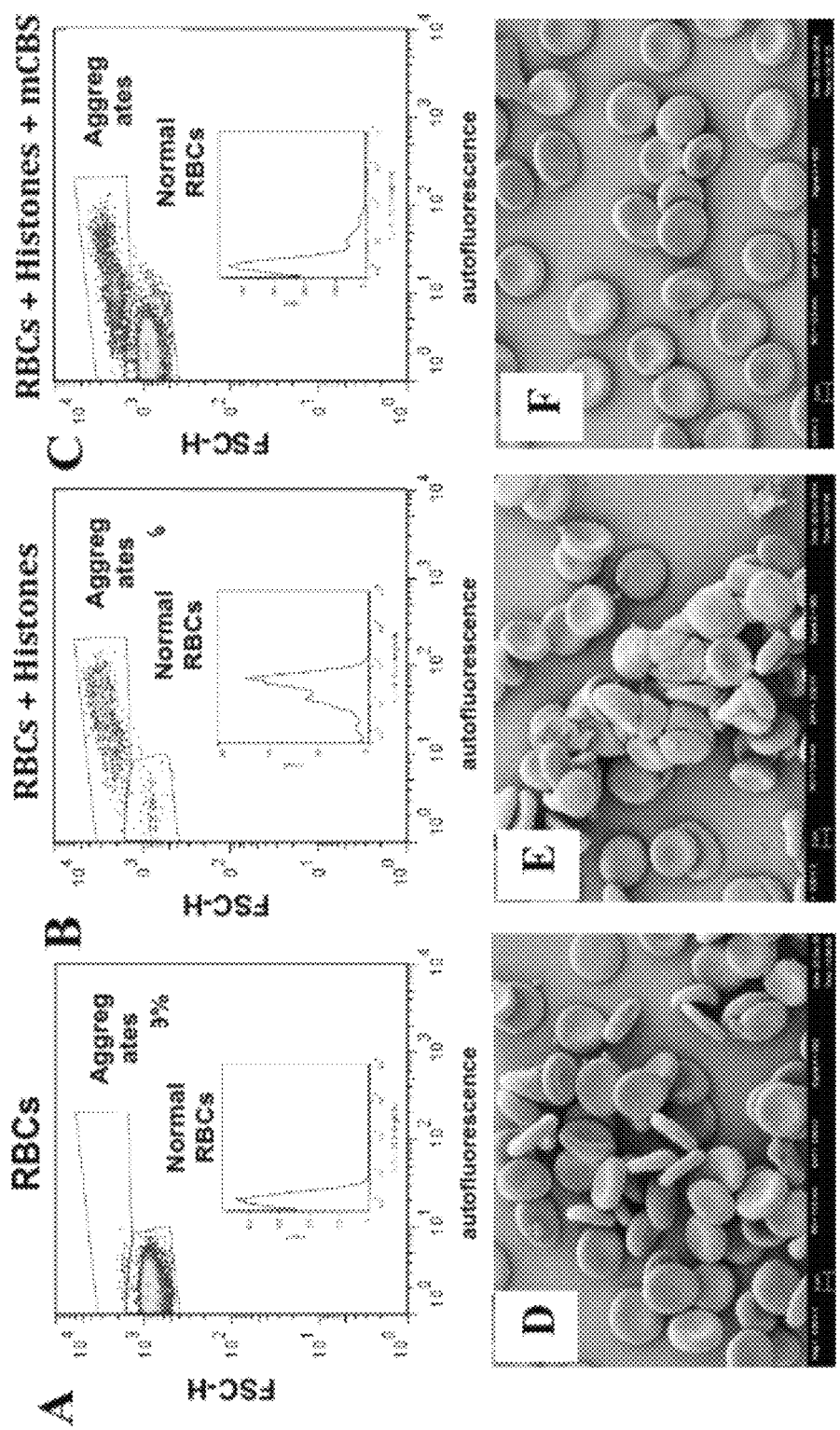
FIG. 8 panels A-C provide a graphical representation of flow cytometry output and panel D-F provide a pictorial representation of scanning electron microscopy results demonstrating that histone-induced RBC aggregation is prevented by mCBS. Isolated human RBCs were analysed by flow cytometry using log FSC vs log autofluorescence (FL-1 channel) parameters or visualised using scanning electron microscopy for extent of aggregation following (A & D) no treatment, (B & E) incubation with histones (400 μg/mL) for 60 min and (C & F) following treatment with histones (400 μg/mL) for 60 min then exposure to mCBS (200 μg/mL) for 10 min.

The damaging effects of histones on RBCs was studied along with the ability of mCBS to abrogate these effects. Initial studies of isolated human RBCs incubated with histones demonstrated significant aggregation using flow cytometry and electron microscopy. As shown in FIG. 8, this RBCs aggregation effect of histones could be prevented by treatment with mCBS (similar data seen with CBS). In this case, isolated human RBCs were analysed using flow cytometry using log FSC vs log autofluorescence (FL-1 channel) parameters (FIG. 8, panels A-C), and visualised using scanning electron microscopy (FIG. 8, panels D-F) for extent of aggregation following no treatment (panels A & D), incubation with histones (400 µg/mL) for 60 min (panels B & E), and immediately following addition of mCBS (200 µg/mL) (panels C & F) then exposure to histones (400

μg/mL) for 60 min. As can be clearly observed from the results in FIG. 8, histone-induced RBC aggregation is prevented by mCBS.

Figure 9A:
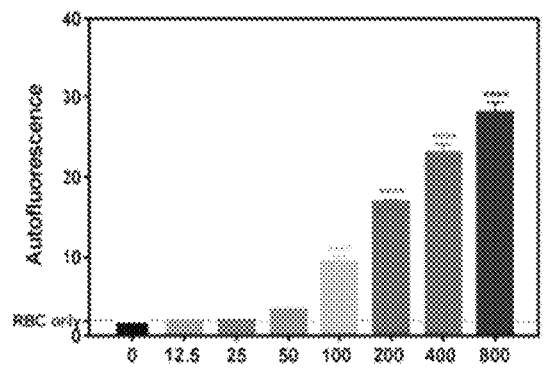
FIG. 9 is a graphical representation demonstrating that mCBS inhibits histone-induced RBC aggregation in a dose dependent manner. Isolated human RBCs were exposed (panel A) to varying concentrations of histones for 60 min and the extent of aggregation measured by the level of autofluorescence (FL-1) as in FIG. 8. (Panel B) as in (A) except that varying concentrations of mCBS are added to RBCs prior to addition of 400 μg/mL of histones. Error bars represent SEM. Asterisks represent significant difference from control (no histones present), P values being <0001 (****).
Figure 9B:
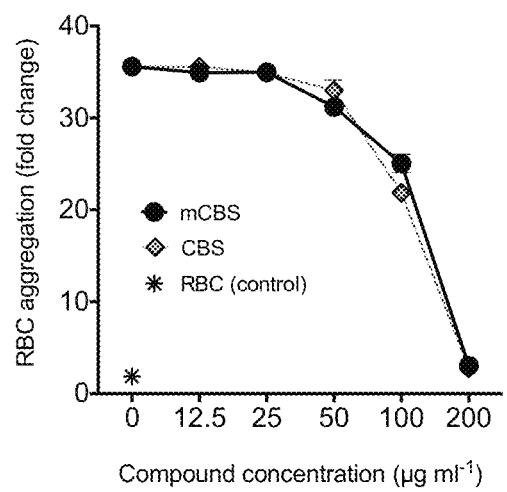

Subsequent experiments were conducted which further confirmed that histones induced aggregation of RBCs in a dose-dependent manner, and furthermore, that mCBS and CBS could significantly reduce this aggregation again in a dose-dependent manner, as shown in FIG. 9. Specifically, in this case, isolated human RBCs were exposed to varying concentrations of histones (0, 1.25, 25, 50, 100, 200, 400 and 800 μg/mL) for 60 min and the extent of RBC aggregation measured by the level of autofluorescence (FL-1) as shown in FIG. 9A. This was then repeated except that varying concentrations of mCBS and CBS (0, 12.5, 25, 50, 100 and 200 μg/mL) were added to the RBCs prior to addition of 400 μg/mL of histones. Again, the extent of RBC aggregation was measured by the level of autofluorescence (FL-1) as shown in FIG. 9B. The results demonstrate that both mCBS and CBS inhibit histone-induced RBC aggregation in a dose dependent manner.

In addition, the susceptibility of RBCs to lysis under increasing shear forces (rate of pipetting) and shear exposure (pipetting repetitions) when incubated for 60 min with increasing concentrations of histones was determined using a robotic pipetting system. The results are shown in FIG. 10. Specifically, isolated human RBCs diluted in a 60% saline solution (normal saline:water ration of 6:4) were incubated with increasing concentrations of histones (0, 1.25, 25, 50, 100, 200, 400 and 800 μg/mL) for 60 min then exposed to increasingly rapid flow rates (mm/s) at 40× repetition (FIG. 10A), and varying repetitions of pipetting at 100 mm/s flow rate (FIG. 10B), or treated with varying concentrations (0, 12.5, 25, 50, 100 and 200 μg/mL) of mCBS (FIG. 10C), then exposed to 400 μg/mL histones for 60 mins and a shear flow rate of 100 mm/s and 40× pipetting repetitions, within a robotic system. The supernatant from each sample was then measured for haemoglobin content at A540 nm as an indication of the extent of RBC lysis.

These experiments were performed in a saline solution of 60% tonicity to induce a baseline stress to the RBCs. Lysis was determined by measuring the haemoglobin level in the supernatant at 540 nm. These results demonstrate that increasing histone concentrations dramatically increase the susceptibility to lysis of RBCs under increasing shear forces and exposure (FIGS. 10A & B). Treatment of RBCs with mCBS (and CBS, not shown) prior to histone exposure can inhibit histone-induced lysis under shear in a dose-dependent manner (FIG. 10C). Accordingly, the results demonstrate that mCBS (and CBS) inhibited histone-induced RBC fragility, even when the histone effect was exacerbated by higher shear flow rates and duration of shear exposure.

Figure 11B:
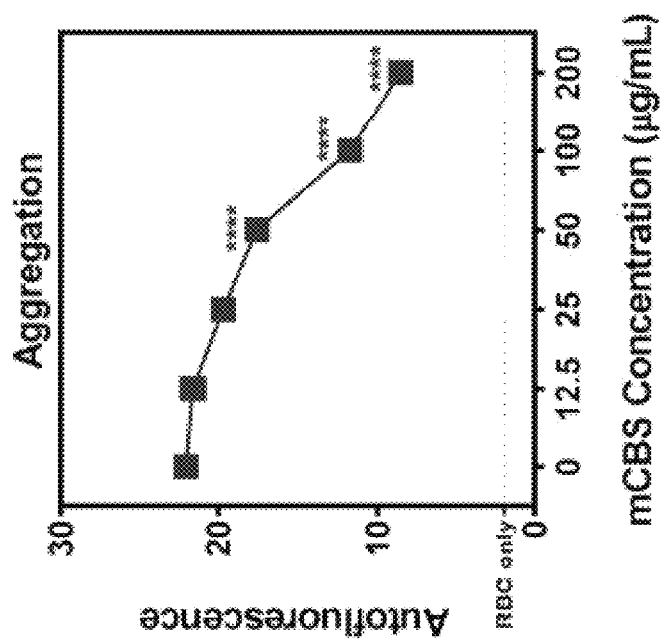
FIG. 11 is a graphical representation demonstrating that mCBS REVERSES histone-induced RBC susceptibility to lysis and aggregation. Isolated human RBCs were exposed to 400 μg/mL of histones for 55 min then varying concentrations of mCBS for 5 min prior to (panel A) the application of shear forces (100 mm/s flow rate and 40× pipetting repetitions) and measurement of haemoglobin in the supernatant via A540 nm, and (panel B) analysis of the extent of RBC aggregation as measured by the level of autofluorescence in FL1 using flow cytometry. Error bars represent SEM. Asterisks represent significant difference from control treatment (histones alone, no mCBS present), all P values being <0001 (****).
Figure 11A:
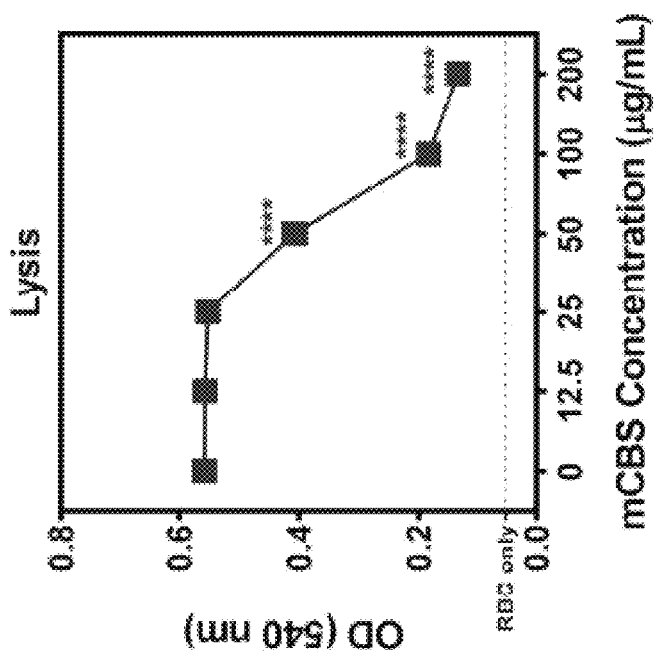

To more closely replicate a clinical scenario, it was demonstrated that treatment of RBCs for 5 min with mCBS subsequent to their exposure to histones for 55 min resulted in the near complete inhibition of susceptibility to lysis under shear forces and to aggregation (FIG. 11). Specifically, isolated human RBCs were exposed to 400 μg/mL of histones for 55 min then varying concentrations of mCBS for 5 min prior to (FIG. 11A) the application of shear forces (100 mm/s flow rate and 40× pipetting repetitions) and measurement of haemoglobin in the supernatant via A540 nm, and (FIG. 11B) analysis of the extent of RBC aggregation as measured by the level of autofluorescence in FL1 using flow cytometry. The results indicate that mCBS was able to reverse histone-induced RBC susceptibility to lysis and aggregation.

Examples 13: Sulfation of mCBS

Figure 12A:
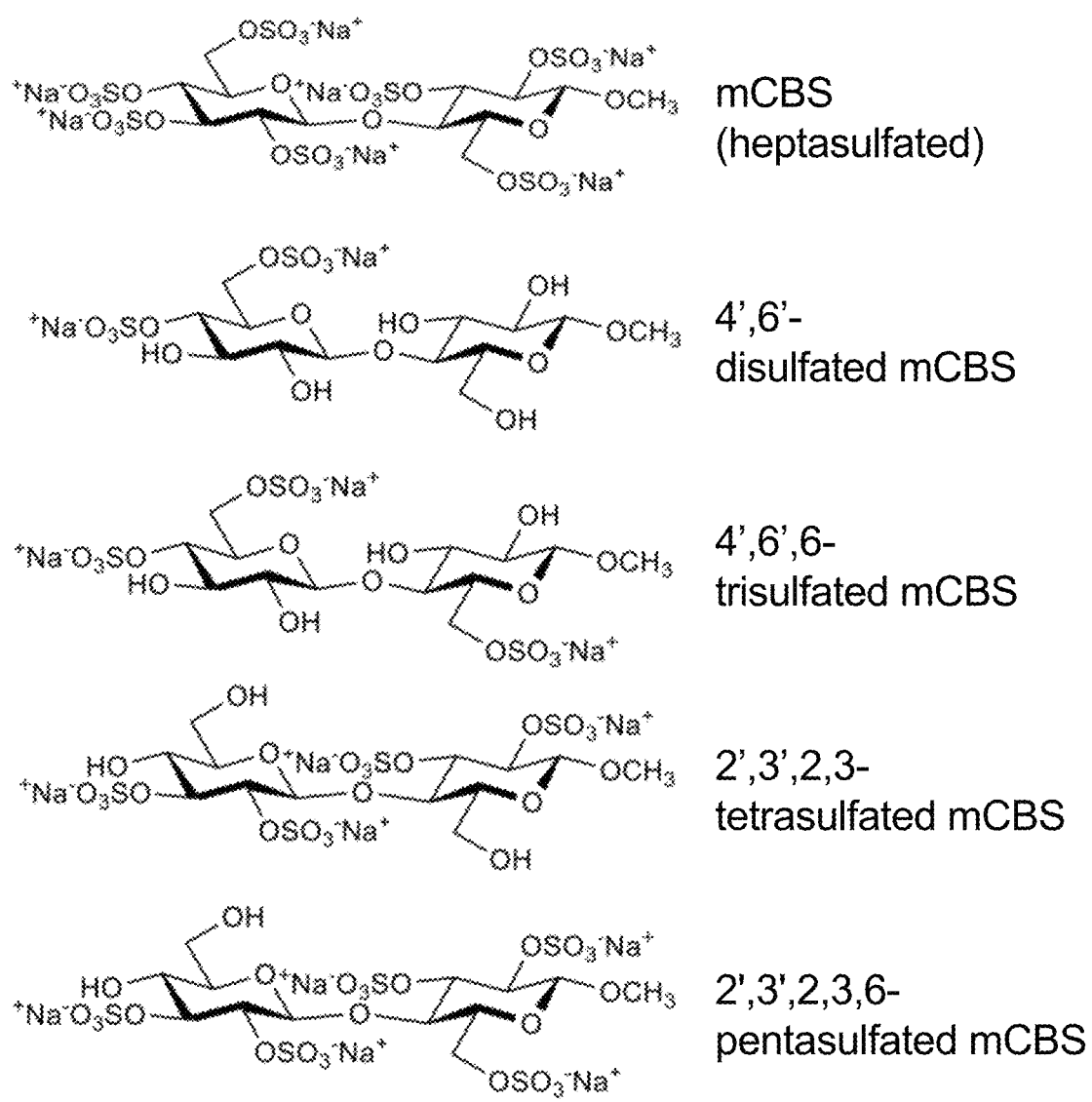
FIG. 12 shows High level sulfation of mCBS is required for it to be an effective inhibitor of histone-mediated pathologies. a, Structures of di-, tri-, tetra-, and pentasulfated mCBS preparations compared to fully sulfated (heptasulfated) mCBS. b, Inhibition curves showing that only the pentasulfated mCBS weakly inhibits histone-mediated cytotoxicity for HMEC-1. c, Similar results obtained when examining inhibition of histone-induced erythrocyte fragility. Data expressed as mean±s.e.m. (n=3).
Figure 12B:
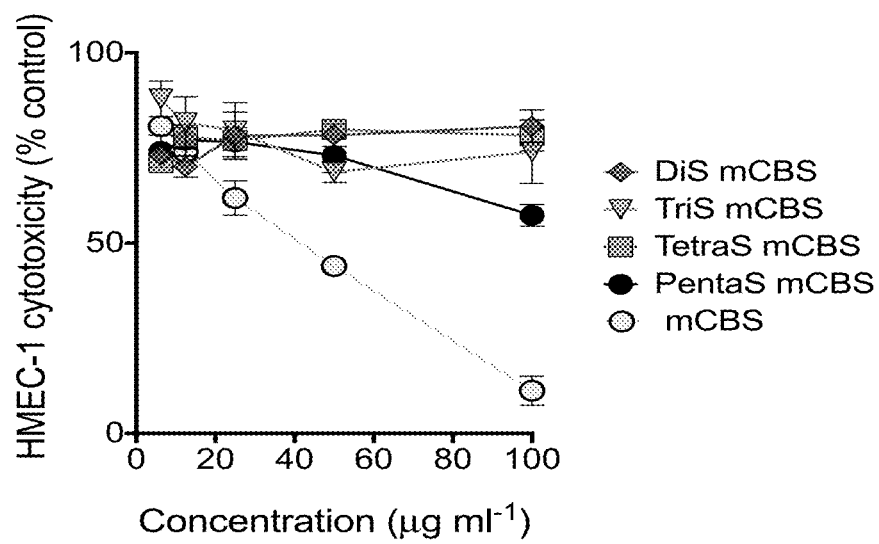
Figure 12C:
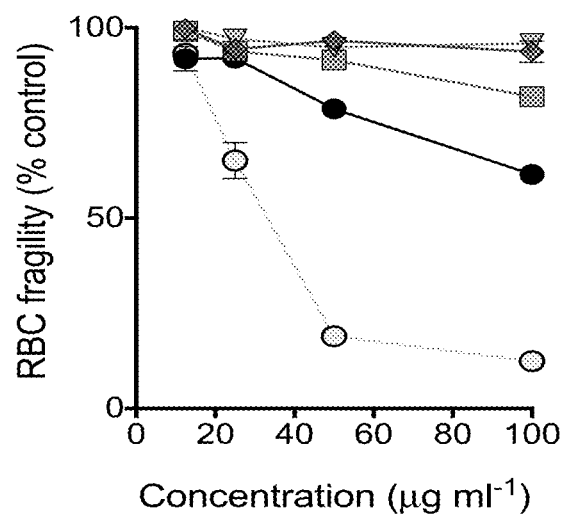

As noted above mCBS is chemically much more stable than CBS and, consequently, represents a better drug candidate. Accordingly, the inventors tested the sulfation required on CBS for activity. When testing these different sulfation states (FIG. 12a) of CBS compounds using HMEC-1 cytotoxicity assays (FIG. 12b) and RBC fragility assays (FIG. 12c) they determined that highly-sulfated CBS was required for anti-histone activity as under-sulfated mCBS had minimal histone-inhibitory activity, even when 5 of 7 O-sulfation sites were occupied.

Example 14: mCBS and CBS Reduce Histone-Induced Platelet Aggregation and Degranulation This example demonstrates that mCBS and CBS inhibit histone-induced platelet aggregation and degranulation.

Platelets play a seminal role in clot formation interacting with plasma coagulation proteins to form an effective plug following vascular injury. Platelets also interact with immune cells assisting in their activation and migration to areas of infection.

Figure 13A:
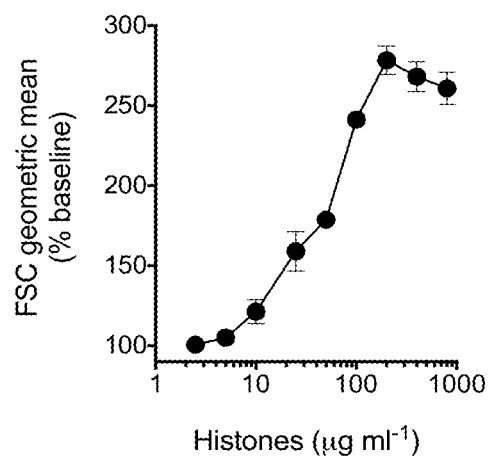
FIG. 13 is a graphical representation demonstrating that histones induce platelet aggregation and degranulation, and these effects can be inhibited by mCBS and CBS. (Panel A) Isolated human platelets were incubated with varying concentrations of histones for 1 hr prior to analysis of aggregation by flow cytometry using FSC and SSC to discriminate between single and aggregated platelets. (Panel B) as in (A), however varying concentrations of mCBS, CBS and the unsulfated CB were added prior to histones (150 µg/mL). (Panel C) Human platelets in whole blood were analysed for degranulation (ATP release) after the addition of increasing concentrations of histones using chemiluminometry with thrombin included as a positive control. (Panel D) as in (C) except that increasing concentrations of mCBS, CBS and the unsulfated CB were added prior to the addition of histones (400 µg/mL). Error bars represent SEM.
Figure 13B:
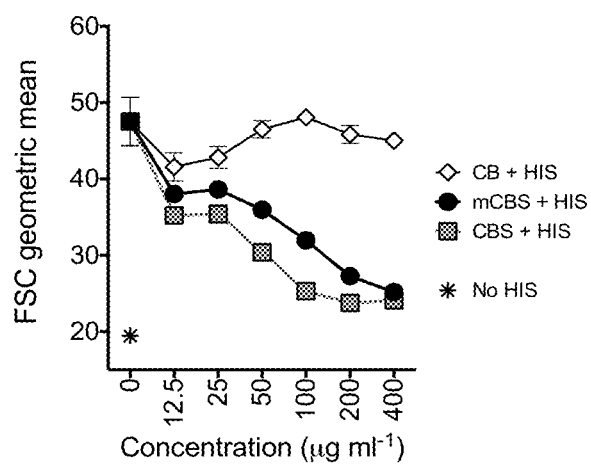
Figure 13C:
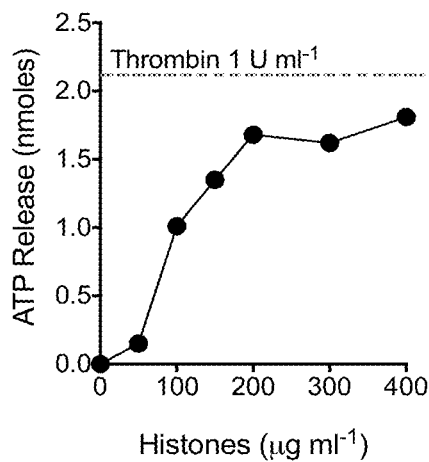
Figure 13D:
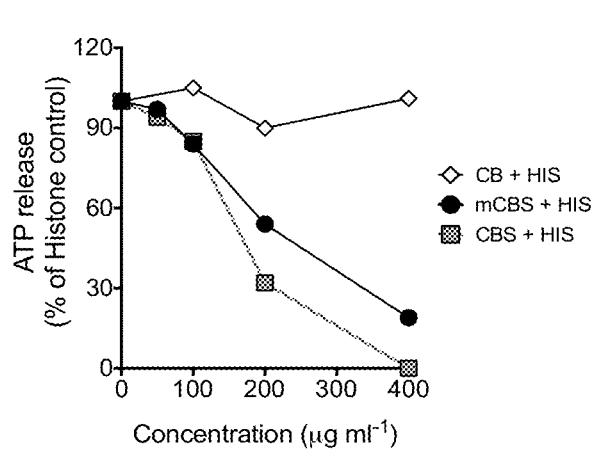

Accordingly, the present inventors studied the effect of histones on platelets and the ability of mCBS and CBS to inhibit these effects. Specifically, isolated and washed human platelets were incubated with varying concentrations of histones (e.g., from 0 to 1000 μg/mL) for 1 hr prior to analysis of aggregation by flow cytometry using FSC and SSC to discriminate between single and aggregated platelets (the results of which are shown in FIG. 13A). This was then repeated with the exception that a range of concentrations of mCBS and CBS were added prior to addition of histones (at a concentration of 150 μg/mL) (FIG. 13B). Human platelets in whole blood were analysed for degranulation after the addition of increasing concentrations of histones using chemiluminometry to detect ATP release, with thrombin included as a positive control (FIG. 13C). This last step was repeated with the exception that increasing concentrations of mCBS and CBS were added prior to the addition of histones (400 μg/mL) (shown in FIG. 13D).

The results provided demonstrate that isolated platelets when exposed to increasing concentrations of histones demonstrated an increased propensity to aggregate, as measured by flow cytometry (FIG. 13A), and to degranulate, as measured using ATP release via platelet luminometry (FIG. 13C). When platelet preparations were pre-treated with mCBS and CBS, however, aggregation (FIG. 13B) and degranulation (FIG. 13D) were significantly reduced. In contrast, unsulfated cellobiose (CB) had no inhibitory activity.

Accordingly, the results confirm that histones induce platelet aggregation and degranulation, and these effects are inhibited by mCBS and CBS.

Example 15: mCBS Prevent Lipid Bilayer Disruption by Histones

The inventors next investigated how histones mediate their cytotoxicity and, consequently, CBS and mCBS protect cells from histone-mediated damage. Since histones bind GAGs, notably HS, which are ubiquitously expressed on cell surfaces, it seemed feasible that histones initiate their cytotoxic effector function by binding to cell surface HS.

To test this idea, HMEC-1 cells were depleted of cell surface HS by incubation with either a mixture of three bacterial heparinases or human platelet heparanase prior to exposure to histones, with HS removal being 86% and 97%, respectively, for the two enzymatic treatments as monitored by flow cytometry.

Figures 14A, 14B:
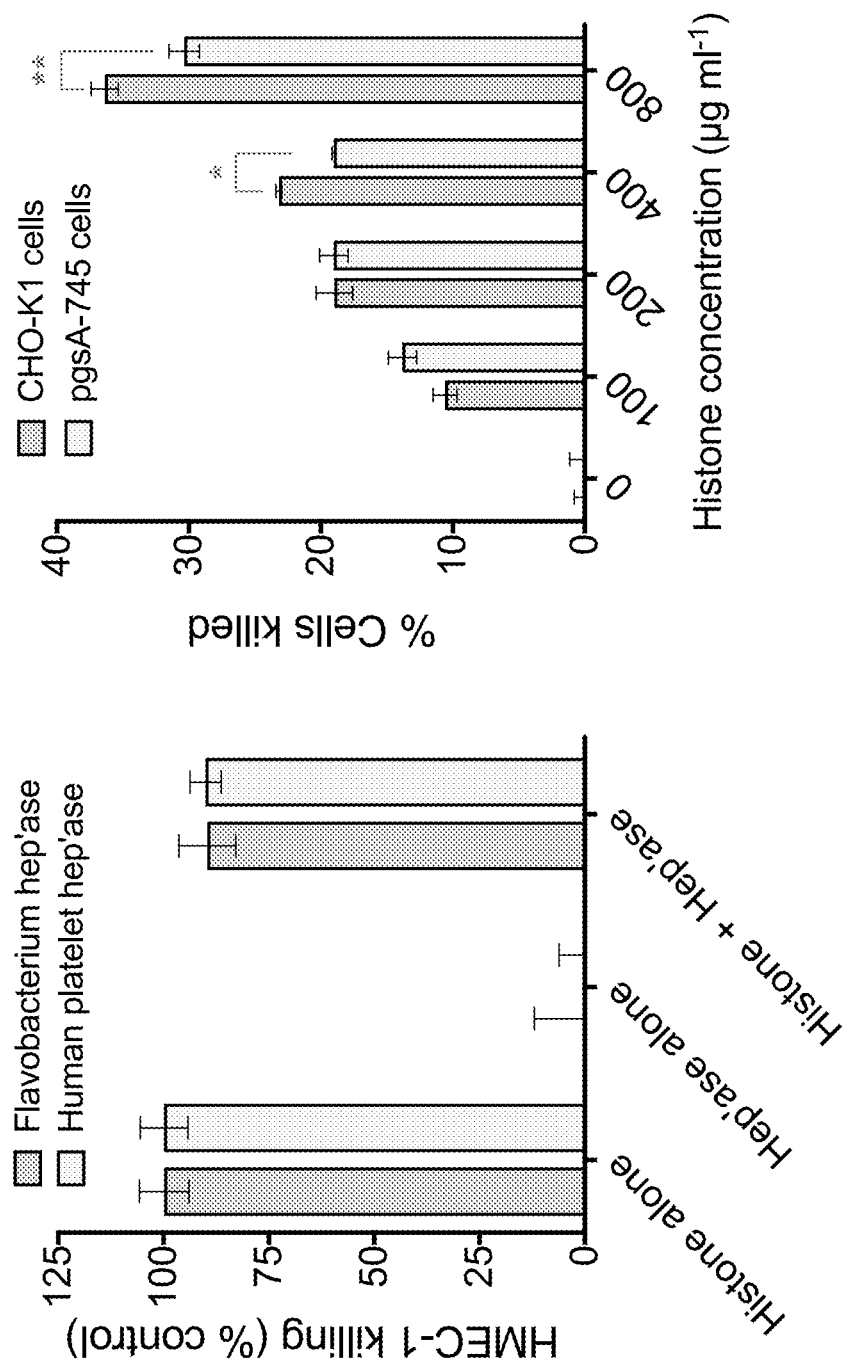
FIG. 14 Histone-mediated cytotoxicity for cells does not require cell surface heparan sulfate. a, HMEC-1 in suspension were treated with either bacterial heparinases 1, 2 and 3 (*Flavobacterium* derived) or human platelet heparanase. The susceptibility of untreated (Histone alone) and heparinise/heparanase treated HMEC-1 to histone-mediated cytotoxicity was then determined. Enzymatic removal of heparan sulfate from HMEC-1 had no effect on the sensitivity of the cells to histone-mediated cytotoxicity nor did the treatment have any effect on HMEC viability (Hep'ase alone). b, Suspensions of wild type CHO-K1 and GAG-deficient pgsA-745 CHO-K1 cells were incubated for 1 h at 37° C. with increasing concentrations of histones and killed cells detected by flow cytometry. Absence of GAGs resulted in only a small, but significant, reduction in the susceptibility of the cells to histone cytotoxicity at high histone concentrations. Data expressed as mean±s.e.m. (n=3). *P≤0.05, **P<0.01 (Two-way ANOVA with Sidak's multiple comparisons test).

The inventors found that pre-treatment of HMEC-1 cells with either bacterial or human HS degrading enzymes had no effect on the sensitivity of the cells to histone-mediated cytotoxicity, the two enzyme pre-treatments also having no effect on HMEC viability (FIG. 14a). To confirm this finding the inventors used a CHO cell line (pgsA-745) that lacks cell surface GAGs due to a mutation in the xylotransferase that initiates GAG chain biosynthesis. Compared to the parent CHO-K1 cell line, loss of cell surface GAGs had little effect on histone cytotoxicity, there being only a small but significant reduction in cytotoxicity at the highest histone concentrations tested (FIG. 14b). Thus, cell surface GAGs are not required for histone-mediated cytotoxicity.

Histones have been previously shown to interact with and damage lipid bilayers and also act as cell penetrating proteins. Thus, the inventors investigated whether histones mediate their cytotoxicity by directly disrupting lipid bilayers.

To examine this possibility artificial lipid bilayers were prepared and their susceptibility to histone rupture detected by changes in current across the bilayers.

Figure 15A:
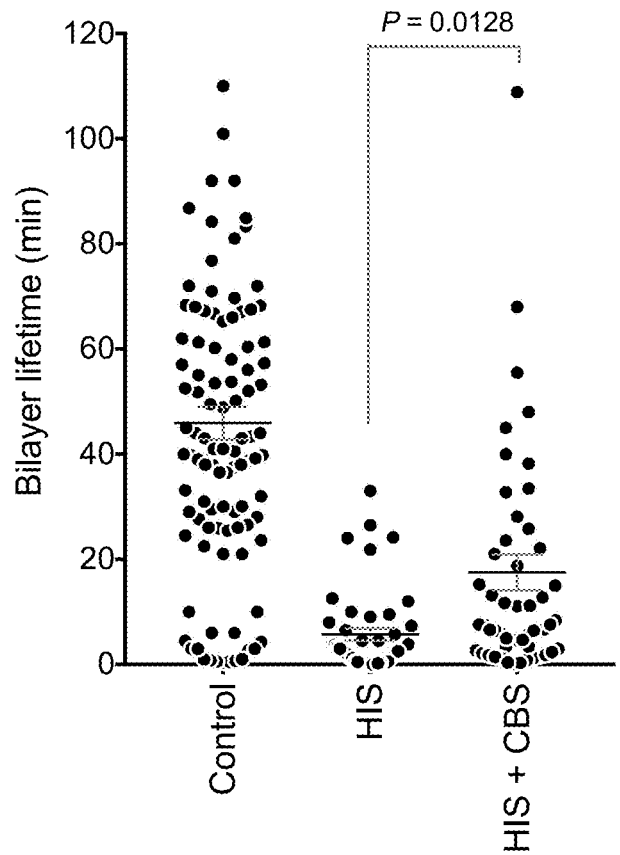
FIG. 15 shows Histones disrupt lipid bilayers and induce a cellular $Ca^{2+}$ flux, processes blocked by mCBS and CBS. a, Lifetime of artificial lipid bilayers exposed to histones (HIS) (1 µm) alone (n=47) or in the presence of CBS (n=52) (10 µM). Control bilayers (n=125) contained the RµR1 ion channel protein. P values calculated using non-parametric Kruskal-Wallis test. b, Representative flow cytometry plots, using $Ca^{2+}$ sensitive dye Indo-1, showing $Ca^{2+}$ fluxing HMEC-1 following histone addition (100 µg ml$^{-1}$). c, Time course of effect of mCBS (100 µg ml$^{-1}$) on histone-induced $Ca^{2+}$ flux by HMEC-1.

Lipid bilayers have a finite lifetime, normally of the order of 30 to 120 min. In the inventors' experiments the control lipid bilayers, containing the ryanodine receptor 1 (RyR1) ion channel protein, had an average lifetime of 46±4 min, addition of histones (1 μM) markedly reducing the lifetime to 5.7±1.2 min (FIG. 15a). In fact, 13 of 47 bilayers (28%) broke within 0.3 to 0.5 min of histone addition whereas only 2 of 125 control bilayers (1.6%) ruptured in the same time period, with higher histone concentrations (≥50 μM) resulting in the rapid rupture of most bilayers (not shown). Bilayers were less prone to rupture by histones when CBS was present, the average bilayer lifetime increasing significantly to 18±4 min and 36±5 min for CBS (FIG. 15a). Compared with histones alone (28%), the incidence of rapid bilayer rupture decreased to 3 of 52 bilayers (5.8%) for CBS.

Earlier studies have also demonstrated that histones can induce in cells non-selective $Ca^{2+}$ channels and plasma membrane depolarisation. These findings further support the concept that histones directly interact with cell surface phospholipids and disrupt membrane integrity.

Figure 15B:
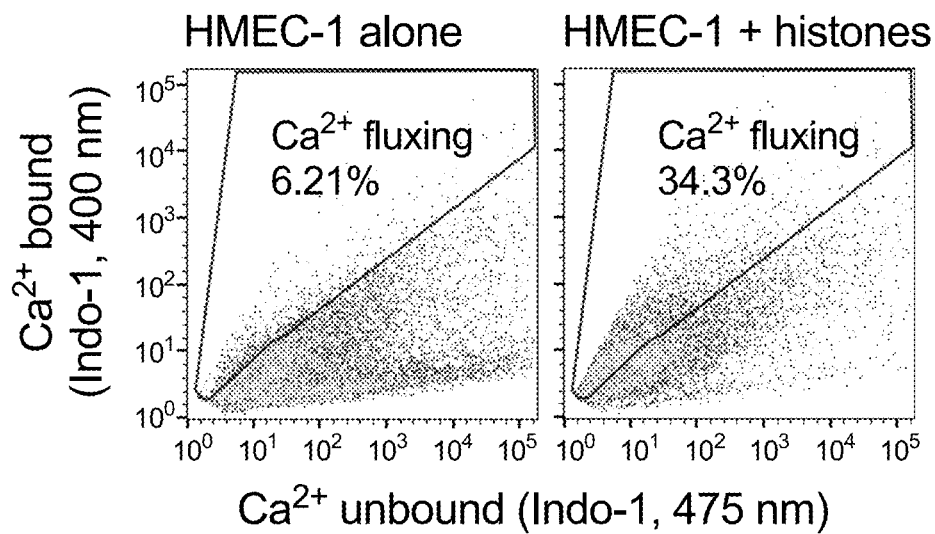
Figure 15C:
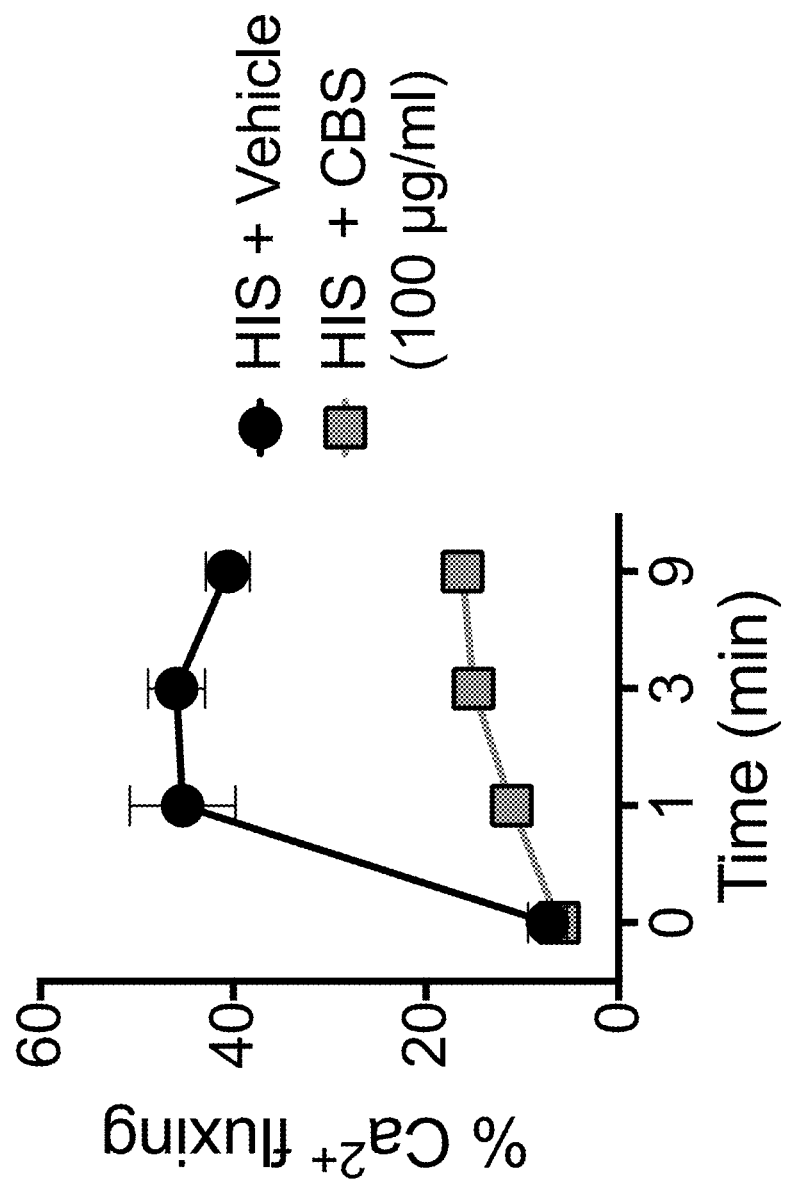

To investigate whether mCBS protect cells against a histone-induced $Ca^{2+}$ flux, HMEC-1 were loaded with the $Ca^{2+}$ sensitive dye, Indo-1, challenged with histones in the presence or absence of mCBS and $Ca^{2+}$ uptake measured by flow cytometry (FIG. 15b). Histones induced an almost 6-fold increase in the population of cells exhibiting high intracellular $Ca^{2+}$ levels, this response plateauing 4-10 min after histone addition. The presence of mCBS substantially inhibited the response (FIG. 15c). The inventors' findings indicate that histones damage cell membranes by directly disrupting the lipid bilayer of cells, with mCBS neutralising this undesirable property of histones.

Example 16: mCBS has Minimal Inherent Anticoagulant Activity and Reduces Histone-Induced Plasma Coagulation Perturbation This example demonstrates that histones reduce blood coagulation, and that mCBS has minimal anticoagulant effects and is able to reduce histone-induced plasma coagulation perturbation.

Despite showing that histones can promote platelet aggregation and degranulation, the present inventors also found that histones reduced the level of whole blood coagulation by inhibiting plasma coagulation specifically through factors involved in the intrinsic pathway.

Figure 16A:
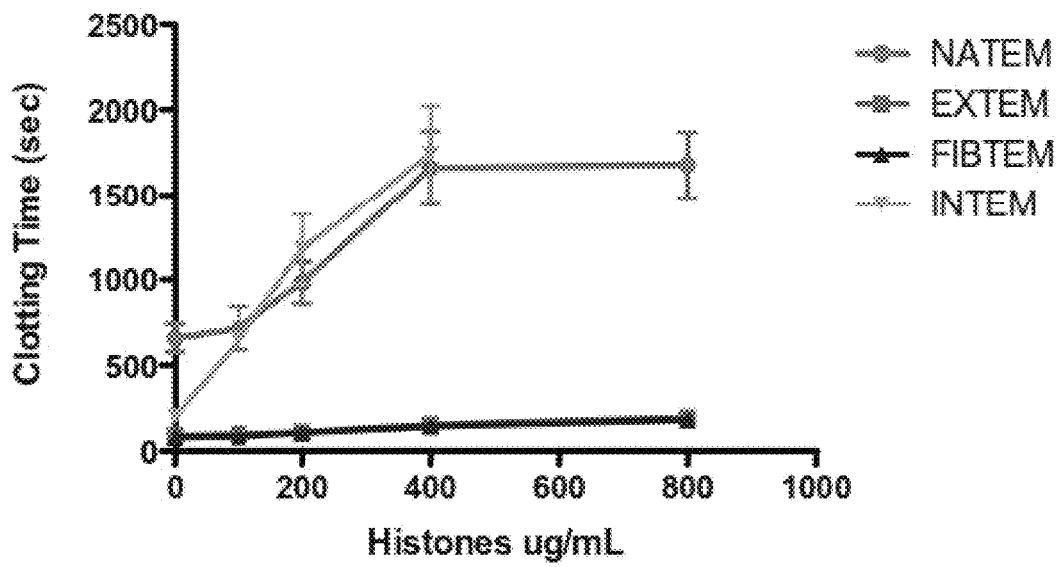
FIG. 16 is a graphical representation demonstrating that histones reduce blood coagulation. Using ROTEM whole blood coagulation analysis (panel A) the addition of increasing histone concentrations to human whole blood resulted in a lengthening of the clotting time in all assays but particularly the NATEM and INTEM assays. (Panel B) The same anticoagulant effect of histones on coagulation was demonstrated using the plasma-based coagulation assay, activated partial thromboplastin time (APTT). Error bars represent SEM.
Figure 16B:
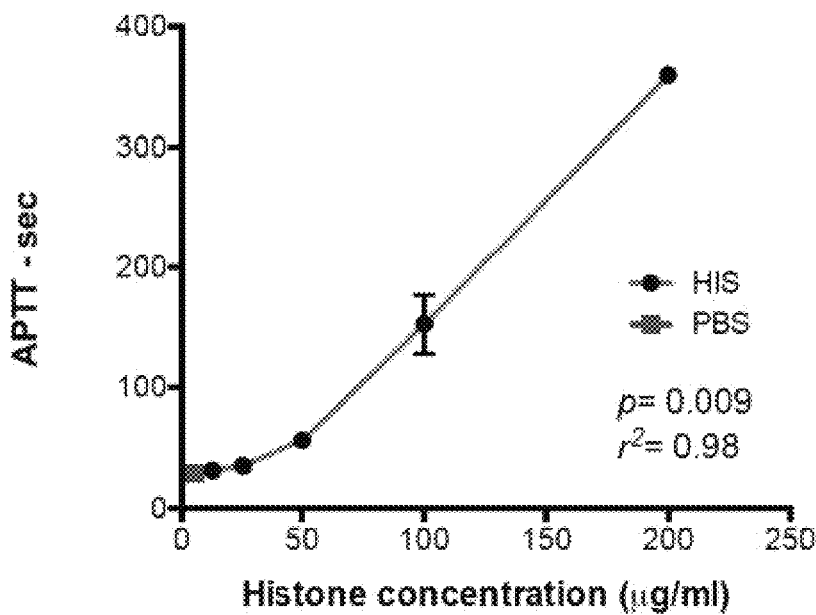

This was demonstrated using rotational thromboelastometry (ROTEM) (FIG. 16A) and the traditional plasma-based activated partial thrombin time (APTT) assay (FIG. 16B).

Specifically, using ROTEM (FIG. 16A) the addition of increasing histone concentrations (0-1000 μg/mL) to whole blood resulted in a lengthening of the clotting time (measured in seconds) in all assays but particularly the NATEM and INTEM assays. The same anticoagulant effect of histones on coagulation was demonstrated using the plasma-based coagulation assay, APTT (FIG. 16B).

Figure 17A:
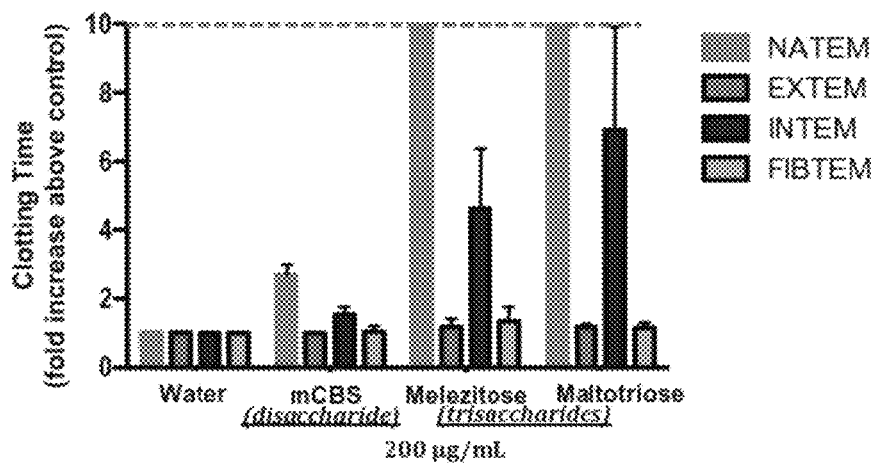
FIG. 17 is a graphical representation demonstrating ROTEM analysis of effects of sulfated saccharides on whole blood coagulation. (Panel A) whole blood was supplemented with mCBS, maltotriose sulfate or melezitose sulfate (200 µg/mL) immediately prior to NATEM (non-activated), EXTEM (extrinsic pathway activation), INTEM (intrinsic pathway activation) and FIBTEM (extrinsic pathway activation with platelets neutralized) assays being undertaken. Data represent clotting time expressed as fold-increase above water control. (Panel B) whole blood, supplemented with varying concentrations of mCBS, melezitose sulfate or maltotriose sulfate, was analysed using the NATEM assay for clotting time. (Panel C) as in (B) except that data represents clot amplitude at 20 min. No clotting was detected with the two trisaccharides at 50 and 100 µg/mL. Error bars represent SEM.
Figure 17B:
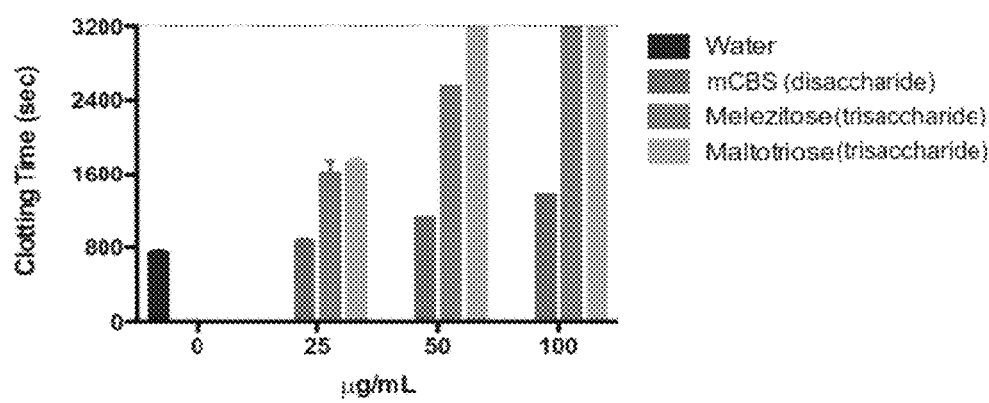
Figure 17C:
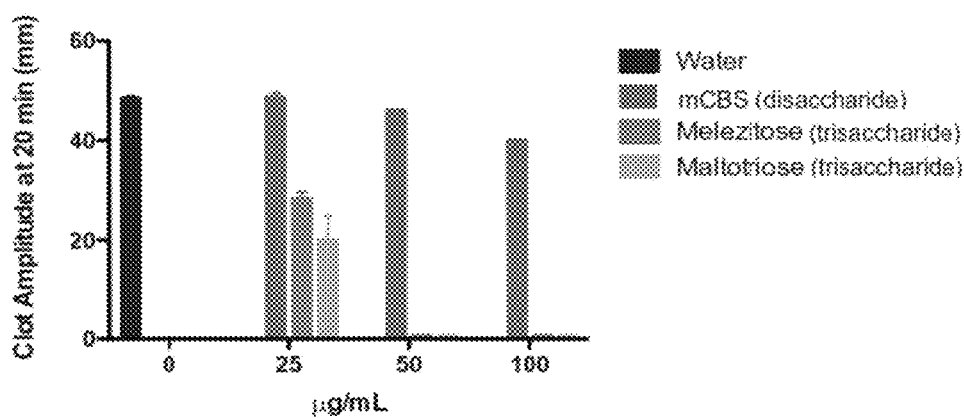

As mCBS is a sulfated disaccharide the inventors reasoned that it could be considered to be a much smaller cousin of the unfractionated- and low-molecular weight anti-coagulant heparin. Accordingly, the coagulation properties of mCBS (200 μg/mL) were studied using ROTEM. Two sulfated trisaccharides, melezitose and maltotriose, were included as comparators (FIG. 17). Specifically, whole blood was supplemented with mCBS, maltotriose or melezitose (200 μg/mL) immediately prior to NATEM (non-activated), EXTEM (extrinsic pathway activation), INTEM (intrinsic pathway activation) and FIBTEM (extrinsic pathway activation with platelets neutralized) assays being undertaken. Data represent clotting time expressed as fold-increase above water control and are shown in FIG. 17A. Whole blood, supplemented with varying concentrations (0 to 100 μg/mL) of mCBS, melezitose or maltotriose, was analysed using the NATEM assay for clotting time, with the results shown in FIG. 17B. The same was then repeated (as in panel B) with the exception that data represents clot amplitude at 20 min. Results of this are shown in FIG. 17C. It was noted that no clot was detected with the two trisaccharides at 50 and 100 μg/mL.

The results shown in FIG. 17 demonstrated that mCBS had minimal to no impact upon whole blood coagulation whereas the 2 sulfated trisaccharide compounds had significant anticoagulant activity detected in the NATEM (non-activated thromboelastometry (TEM)) and the INTEM (Intrisinc pathway activated TEM) assays. As the NATEM assay was the most sensitive to changes induced by these compounds, lower concentrations of the 3 sulfated compounds were added to whole blood to better define their potency as anticoagulants. This analysis demonstrated that the sulfated trisaccharides doubled the control clotting time at 25 μg/mL whereas 100 μg/mL of mCBS was required to achieve the same outcome (FIG. 17B).

Figure 18:
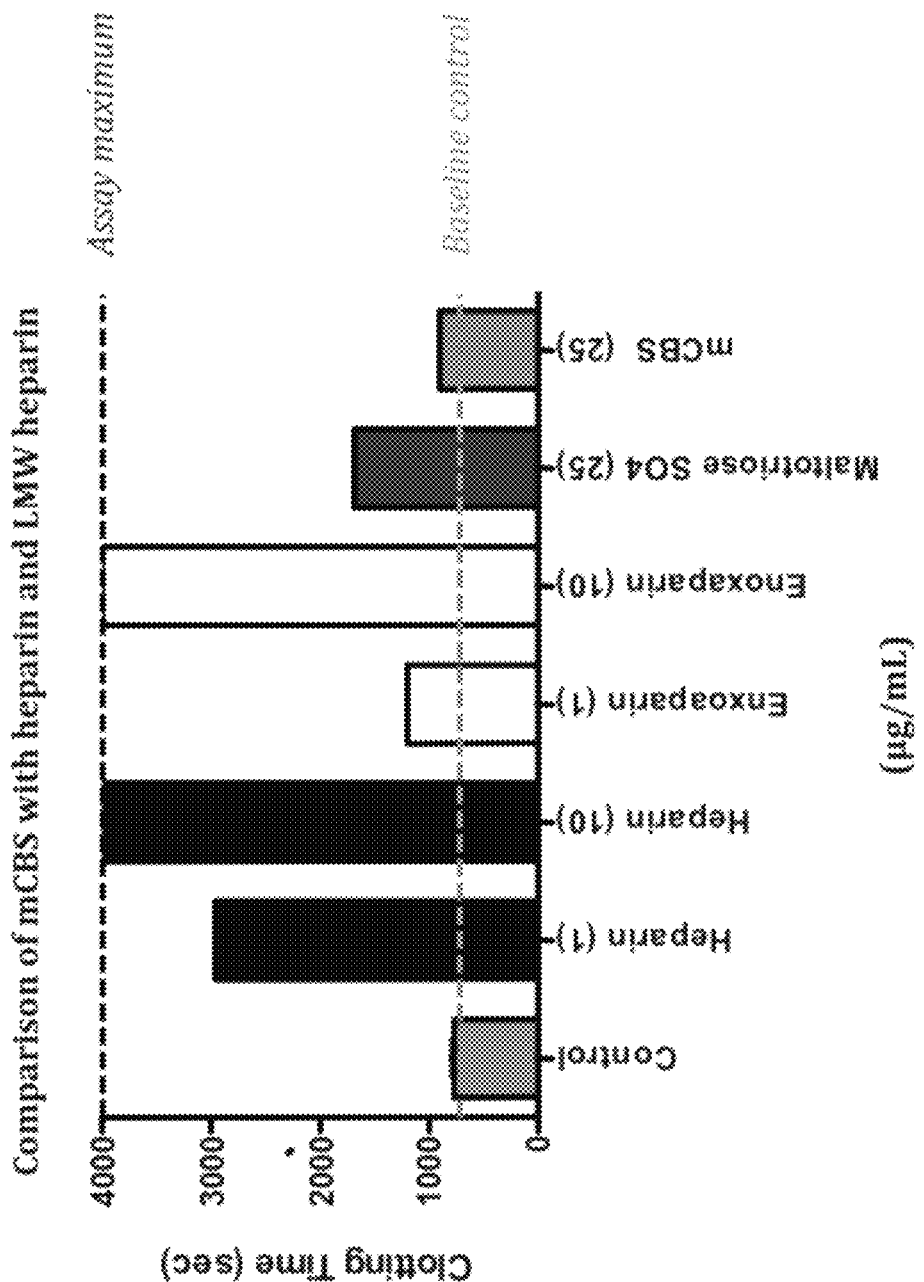
FIG. 18 is a graphical representation demonstrating a comparison of the anticoagulant effect of mCBS with heparin and the low-molecular weight heparin, Enoxaparin. Using the NATEM assay, whole blood coagulation was measured following the addition of heparin, Enoxaparin, the trisaccharide, maltotriose sulfate, and mCBS at the concentrations in g/mL indicated in brackets.

Furthermore, a comparison of the anticoagulant effect of mCBS with heparin and the low-molecular weight heparin, Enoxaparin, was conducted. Specifically, using the NATEM assay, whole blood coagulation was measured following the addition of heparin (at a concentration of 1 □g/mL or 10 □g/mL), enoxaparin (at a concentration of 1 □g/mL or 10 □g/mL), the trisaccharide maltotriose sulfate (at a concentration of 25 □g/mL), or mCBS (at a concentration or 25 □g/mL). Results are shown in FIG. 18. A comparison of mCBS with unfractionated heparin and low-molecular weight heparin (LMWH) demonstrated a 110-fold reduction in the anticoagulant activity of mCBS compared to the LMWH, Enoxaparin, and a >750-fold reduction compared to unfractionated heparin.

Figure 19:
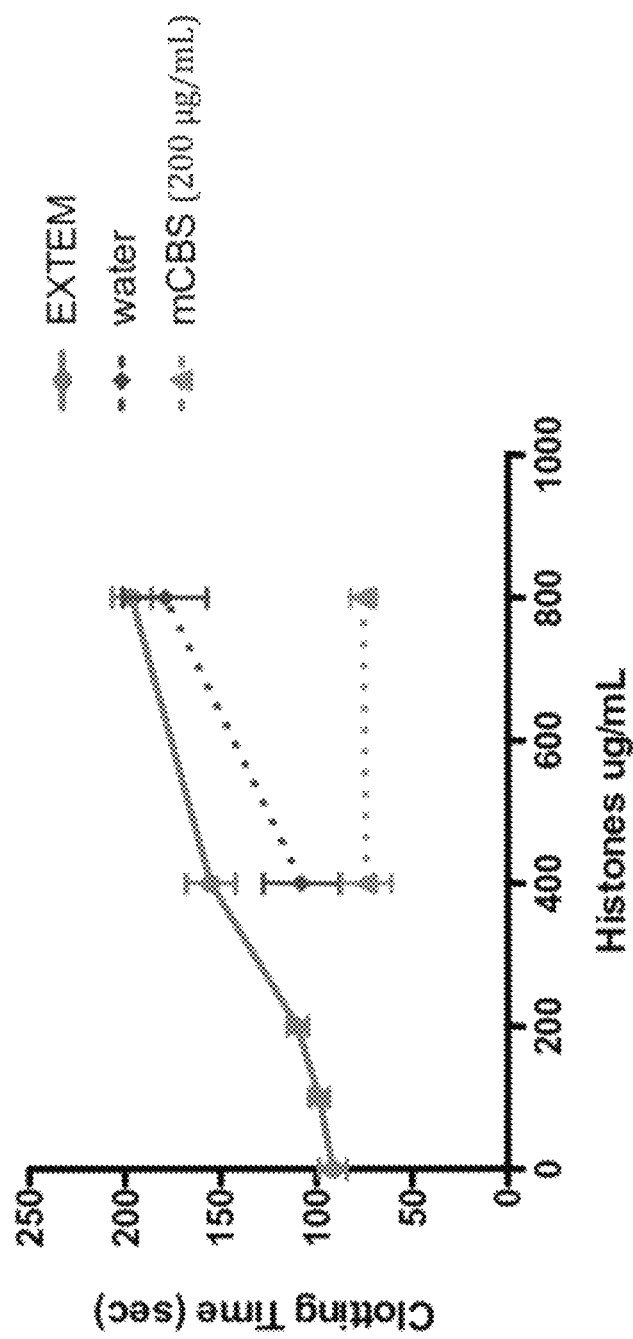
FIG. 19 is a graphical representation demonstrating that mCBS inhibits histone-induced perturbations of whole blood coagulation. Using the EXTEM assay, the prolongation of clotting time induced by 400- and 800 µg/mL of histones could be inhibited by the prior addition of 200 µg/mL of mCBS. The addition of the same volume of water had no inhibitory effect. Error bars represent SEM.

As histones were found to increase clotting time in the EXTEM assay, whereas mCBS had no impact upon the same parameter, the ability of mCBS to inhibit histone-induced perturbation of coagulation was also tested using the NATEM assay. The results of this are shown in FIG. 19. As demonstrated, the addition of 200 µg/mL of mCBS was able to inhibit the anticoagulant effects of both 400 and 800 µg/mL of histones. In comparison, the same volume of water had no effect (FIG. 19). Accordingly, the results demonstrate that mCBS inhibits histone-induced perturbations of whole blood coagulation.

In-Vivo Evidence of the Biological Effects of mCBS and CBS

Example 17: mCBS and CBS Protect Organs from Histone-Mediated Injury

This example demonstrates that mCBS and CBS are able to protect mice from histone-induced organ damage.

Figures 20A, 20B:
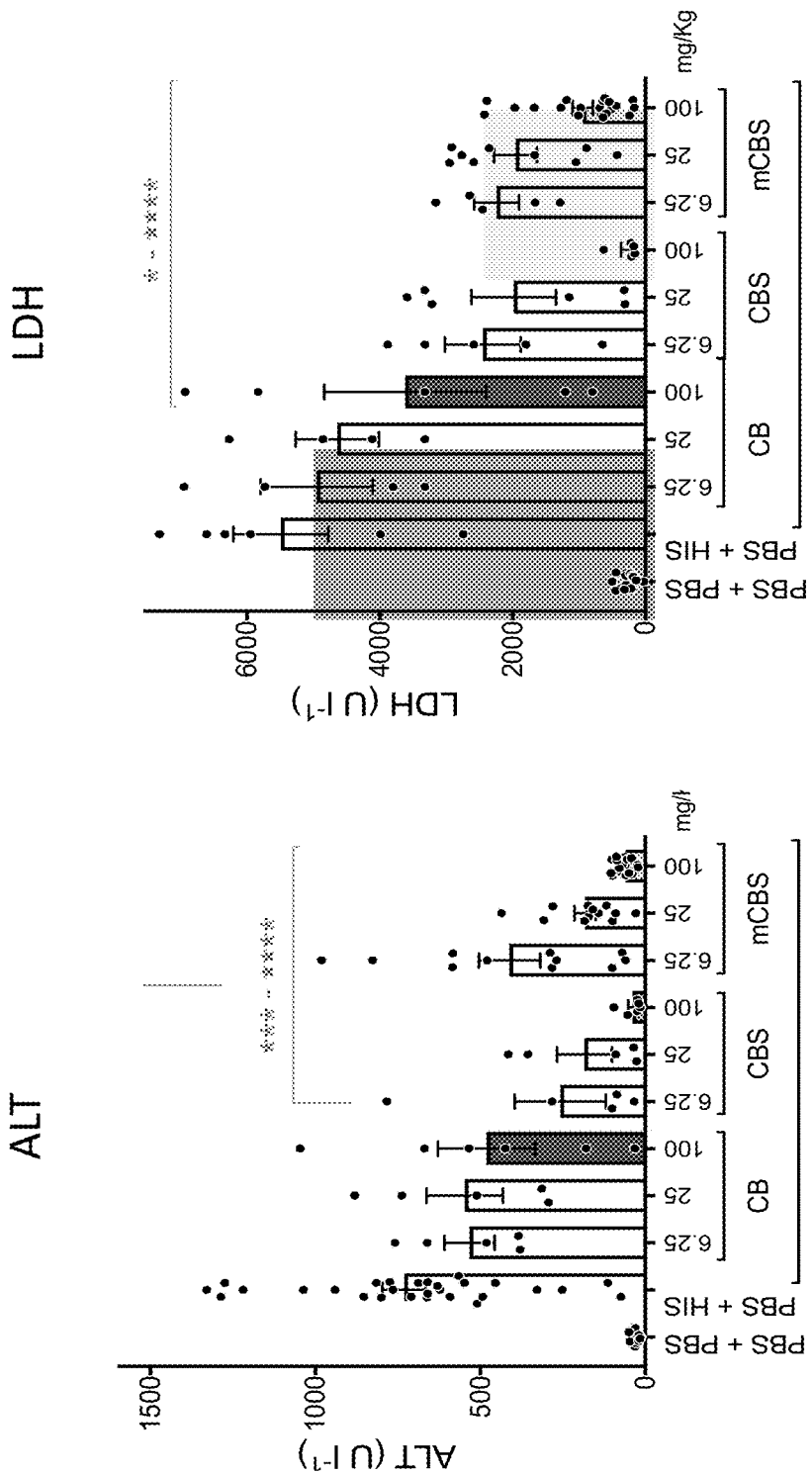
FIG. 20 is a graphical representation demonstrating that mCBS and CBS protect mice from histone-induced organ damage. Mice received an intraperitoneal injection of mCBS, CBS or the unsulfated CB at the concentrations indicated, (or an equivalent volume of PBS) 10 min prior to an intravenous injection of 50 mg/kg of histones (or an equivalent volume of PBS). Blood was collected retro-orbitally 4 hr later for analysis of markers of cell injury (LDH—lactate dehydrogenase), liver dysfunction (ALT—alanine aminotransferase) and kidney dysfunction (Crea—creatinine). Error bars represent SEM. Data mean±s.e.m. *P≤0.05, P<0.01, *P<0.001, ****P<0.0001 (one way ANOVA with Dunnett's multiple comparisons test).
Figure 20C:
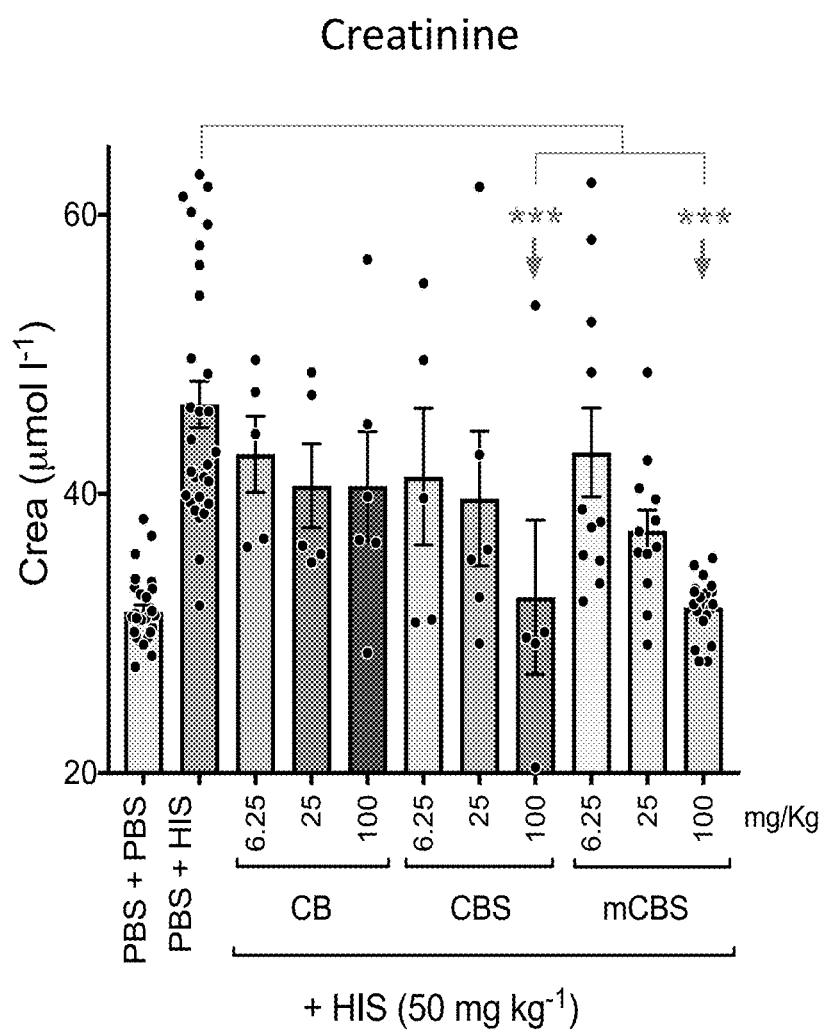

Intravenous injection of mice with histones has been demonstrated to result in microthrombii forming in organs, cell injury and organ dysfunction (Xu et al., Extracellular histones are major mediators of death in sepsis. *Nat Med.* 2009 November; 15(11):1318-21. 2009). Using the same mouse model for sepsis as in Xu et al., 2009, the present inventors investigated whether mCBS and CBS are able to protect mice from histone-induced organ damage. Mice received an intra-peritoneal injection of mCBS or CBS, at concentrations of 6.25, 25 and 100 mg/kg, or an equivalent volume of PBS 10 min prior to an intravenous injection of 50 mg/kg of histones (or an equivalent volume of PBS). Blood was collected retro-orbitally 4 hr later for analysis of markers of cell injury (lactate dehydrogenase, LDH), liver dysfunction (alanine aminotransferase, ALT) and kidney dysfunction (creatinine, Creat) as described earlier. The results are shown in FIG. 20. Specifically, using these results, the inventors were able to show that mCBS and CBS, in a dose-dependent manner, protects animals from histone-mediated injury with significant preservation of liver and kidney function demonstrated (FIG. 20) whereas unsulfated CB was inactive.

Example 18: mCBS Protects Cells within the Bloodstream from Histone-Mediated Injury This example demonstrates that mCBS reduces and/or prevents histone-mediated reductions in circulating leukocytes, platelets and erythrocytes in mice.

Figure 21C:
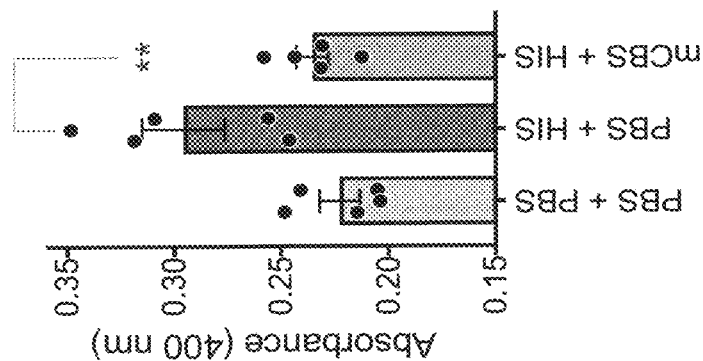
FIG. 21 is a graphical representation demonstrating that mCBS reduces or prevents histone-mediated reductions in circulating leukocytes, platelets and erythrocytes. Mice received an intraperitoneal injection of 100 mg/kg of mCBS (or an equivalent volume of PBS) 10 min prior to an intravenous injection of 50 mg/kg of histones (or equivalent volume of PBS) then 10 min later were bled retro-orbitally. The whole blood was analysed for leukocyte, platelet and erythrocyte numbers and haemoglobin concentration using an ADVIA 2120 haematology system. Error bars represent SEM. Asterisks represent significant difference from PBS+ HIS control, P values being <01 (), <001 (*) (one way ANOVA with Dunnett's multiple comparisons test).
Figure 21B:
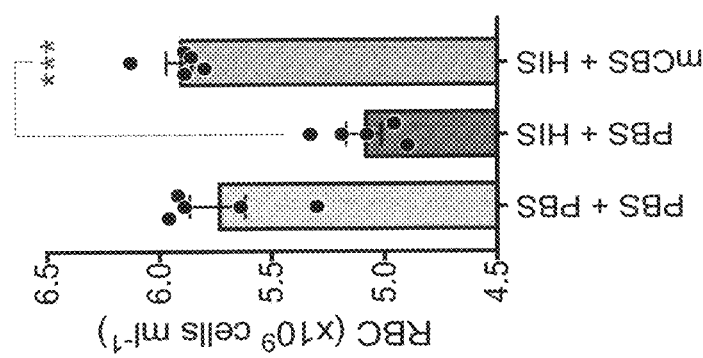
Figure 21A:
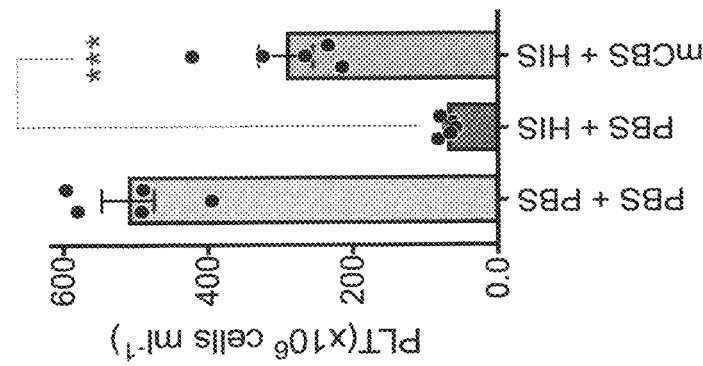

The injection of histones into mice has also been shown to induce severe thrombocytopenia. Accordingly, the inventors in this example investigated the protective effect of mCBS on cells within the blood stream following intravenous injection of histones. Using the same mouse model as in the previous example, mice received an intra-peritoneal injection of 100 mg/kg of mCBS (or an equivalent volume of PBS) 10 min prior to an intravenous injection of 50 mg/kg of histones (or equivalent volume of PBS) then 10 min later were bled retro-orbitally. The whole blood was analysed for leukocyte, platelet and erythrocyte numbers and haemoglobin concentration using an ADVIA 2120 haematology system. Results are shown in FIG. 21. The results demonstrated that not only are circulating platelet numbers significantly reduced within minutes of histone injection but also leukocytes, erythrocytes (red blood cells) and plasma haemoglobin levels. Furthermore, when mCBS was injected prior to histones, these histone-mediated effects were significantly inhibited if not completely abolished (FIG. 21).

Accordingly, these results indicate that mCBS protects cells within the bloodstream from histone-mediated injury.

Example 19: CBS and mCBS Inhibit Sepsis

Figure 22A:
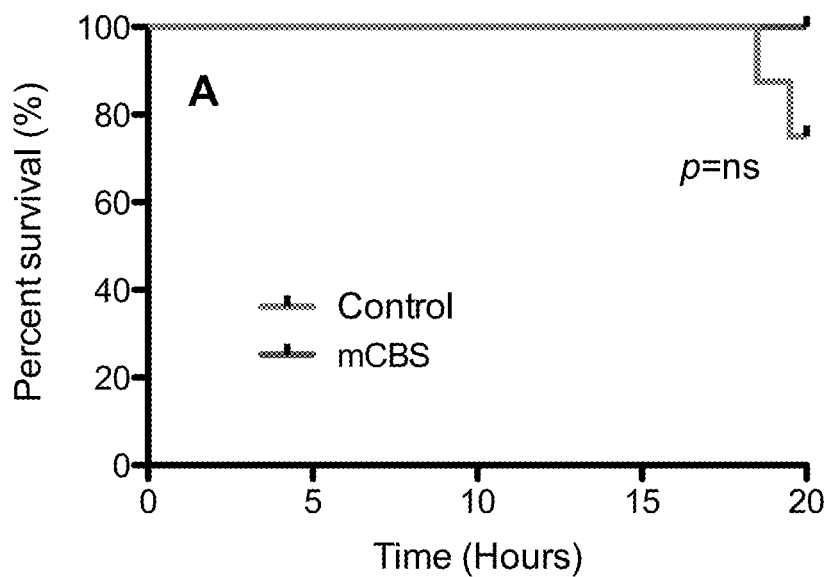
FIG. 22 shows that mCBS protect rats from moderate sepsis-induced cell damage. A graphical representation demonstrating survival rate of mCBS treated (mCBS) and not treated (Control) rats in a rat model of moderate sepsis (panel A), and demonstrating that mCBS reduces cell damage (lactate dehydrogenase (LDH)) in an animal model of moderate sepsis (panel B). Male Wistar rats (n=8/group) underwent laparotomy, caecal ligation and puncture (CLP)
Figure 22B:
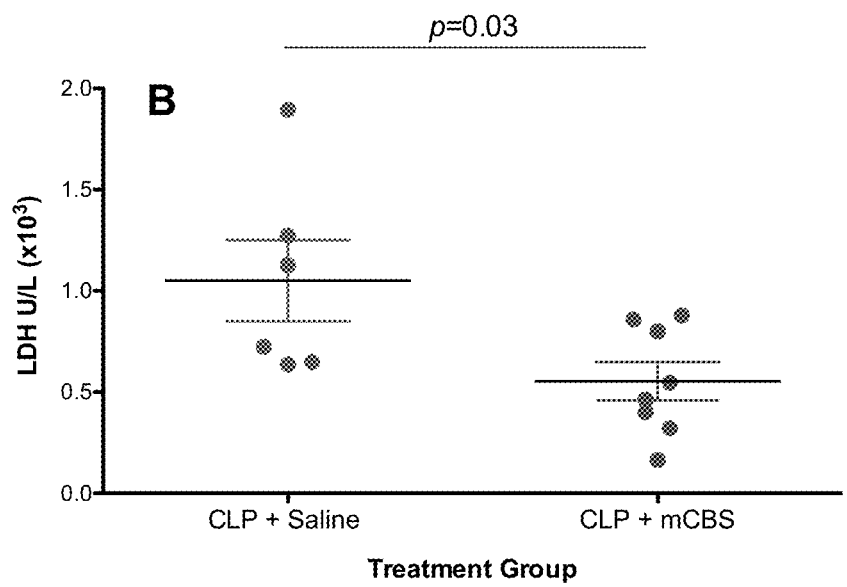

The Inventors next examined the efficacy of mCBS and CBS in rat caecal ligation puncture (CLP) models of moderate and severe sepsis. In the moderate sepsis example where few deaths occurred (FIG. 22A) but a SIRS response is elicited, it was demonstrated that mCBS, treatment significantly reduced circulating LDH levels compared to the Control CLP group (0.6±0.1 and 1.1±0.2 U/L×10$^3$, p=0.03; FIG. 22B). No differences were found in ALT or creatinine levels between the groups confirming the induction of a milder form of sepsis (data not shown).

Figure 23A:
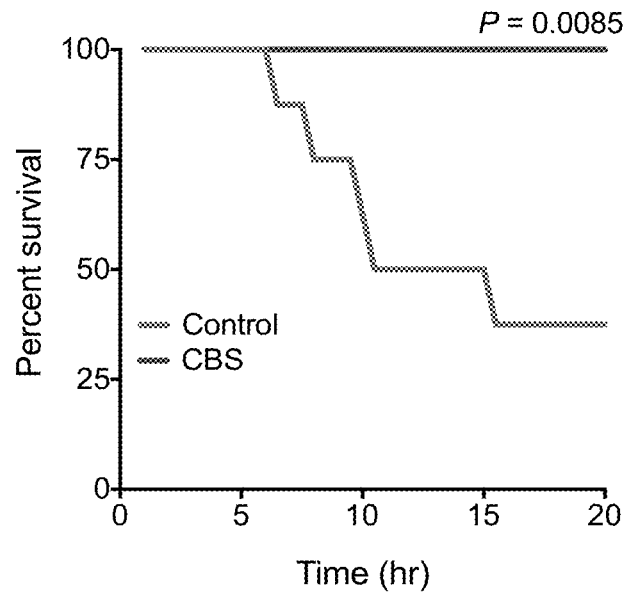
Figure 23B:
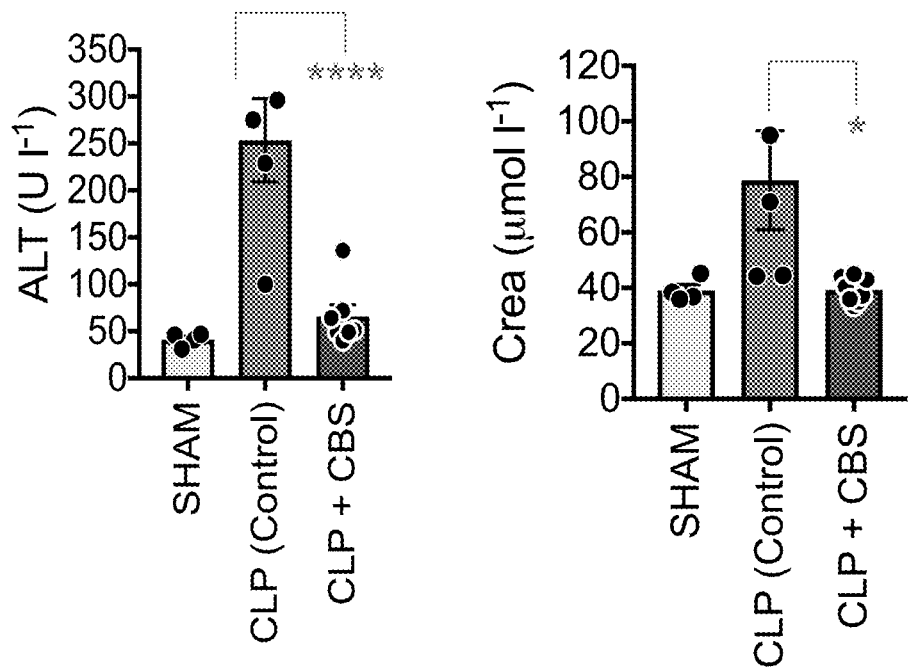

In the severe sepsis example where morbidity was much more pronounced, rodent mortality was significantly less in animals receiving CBS compared with PBS controls, in fact there were no mortalities in the CBS treatment group (FIG. 23A). Importantly, the high ALT and creatinine levels detected in the untreated group, indicative of extensive liver and kidney damage, were not seen in the CBS treated animals (FIG. 23B).

Collectively these results indicate that CBS and the more stable mCBS, can limit the histone-mediated effects of sepsis and SIRS hence limiting tissue damage and preserving end-organ function.

Example 20: CBS and mCBS Inhibit IRI

To investigate the capacity of CBS and mCBS to inhibit IRI, a rat cardiac IRI (cIRI) model was employed. The ischemic zone was equal between groups (FIG. 24A). CBS treatment significantly reduced the area of microvascular obstruction (FIG. 24B) and myocardial necrosis in the ischemic zone by 50% (FIG. 24C). Furthermore, in a rat skin flap IRI model mCBS consistently and significantly increased the viable area of the skin flap (FIG. 25).

Example 21: CBS Inhibits Venous Thrombosis

To examine whether CBS controls the localised vascular effects of histones, a histone-mediated model of deep vein thrombosis (DVT) was established and shown to be almost totally inhibited by CBS (FIG. 26).

These data are consistent with both systemic and localised vascular pathologies mediated by free histones being amenable to inhibition by CBS/mCBS.

Example 22: mCBS Inhibits Autoimmunity

The Inventors next assessed the ability of mCBS to inhibit an animal model of autoimmunity called experimental autoimmune encephalomyelitis (EAE) which resembles multiple sclerosis in humans. The data are shown in FIG. 27 and revealed that mCBS, when administered daily, resulted in substantial protection of the mice from EAE development over a 35 day window.

In the above examples, the inventors describe the development of small polyanionic molecules as very effective in vitro inhibitors of a number of pathological processes mediated by free histones, such as cytotoxicity, erythrocyte fragility/deformability and platelet activation.

These data also provide proof-of-principal data that CBS/mCBS are able to inhibit histone-mediated ailments, including sepsis, IRI, thrombosis and autoimmunity.

In humans and animals, mCBS is highly stable and well tolerated at high doses, the only dose-limiting feature being anticoagulant activity, however, this activity is 110-fold lower than LMW-heparin and 750-fold lower than unfractionated-heparin. Thus mCBS represents a new class of therapeutic with considerable clinical potential.

The invention claimed is:

1. A pharmaceutical composition comprising:
   a compound; and
   a buffer system,
      wherein the compound is a polyanionic sulfated cellobioside modified with a small uncharged glycosidically linked substituent at its reducing terminus or a pharmaceutically acceptable salt thereof, having the general structure of:

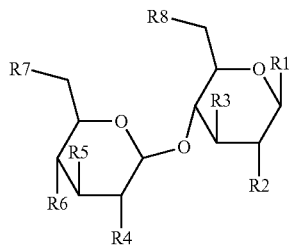

wherein:
   R1 is a small uncharged glycosidically linked substituent selected from the group consisting of O—($C_{1-6}$)alkyl and S—($C_{1-6}$)alkyl,
   R2 to R8 are each a sulfate group selected from the group consisting of O-sulfate, and a pharmaceutically acceptable salt thereof,
   wherein the buffer system is selected from the group consisting of a phosphate buffer system, and citrate buffer system, and
   wherein the pharmaceutical composition is buffered at a pH ranging from pH 7.1 to pH 7.6.

2. The pharmaceutical composition of claim 1, wherein R1 is a methoxy or an ethoxy group.

3. The pharmaceutical composition of claim 1, wherein the compound is sulfated β-O-methyl cellobioside disaccharide or a pharmaceutically acceptable salt thereof.

4. The pharmaceutical composition of claim 1, wherein the compound is sodium β-O-methyl cellobioside sulfate.

5. The pharmaceutical composition of claim 1, further comprising a pharmaceutically acceptable carrier, or a pharmaceutically acceptable excipient, or a pharmaceutically acceptable diluent, or a pharmaceutically acceptable adjuvant.

6. The pharmaceutical composition of claim 1, wherein the buffer system is selected from the group consisting of disodium hydrogen phosphate-monobasic sodium phosphate, and sodium citrate dihydrate-citric acid.

7. The pharmaceutical composition of claim 1, wherein the pharmaceutical composition is buffered at a pH of 7.5.

8. The pharmaceutical composition of claim 1, wherein the pharmaceutical composition is formulated for single dose or multi-dose administration to a subject in need thereof.

9. The pharmaceutical composition of claim 1, wherein the pharmaceutical composition is formulated for administration to the subject in need thereof by continuous infusion.

10. The pharmaceutical composition of claim 1, wherein the pharmaceutical composition is formulated for administration to the subject in need thereof at the same time as, or concomitantly with, a second active agent.

11. The pharmaceutical composition of claim 1, comprising a second active agent selected from the group consisting of an anti-inflammatory agent, an antibiotic agent, an antiviral agent, an antifungal agent, and an adjunct treatment for the medical condition or disease being treated.

12. The pharmaceutical composition of claim 1, wherein the pharmaceutical composition is formulated for administration orally, intravenously, intramuscularly, subcutaneously, transdermally, or transmucosally.

* * * * *